United States Patent
Li et al.

(10) Patent No.: US 12,391,758 B2
(45) Date of Patent: Aug. 19, 2025

(54) ANTI-PD-L1 CANCER IMMUNOTHERAPY ANTIBODIES

(71) Applicants: 1GLOBE BIOMEDICAL CO., LTD., Beijing (CN); 1GLOBE HEALTH INSTITUTE LLC, Norwood, MA (US)

(72) Inventors: Chiang J. Li, Cambridge, MA (US); Shyam Unniraman, Newton, MA (US); Hannah Bader, Waltham, MA (US); Mithilesh Jha, Sharon, MA (US)

(73) Assignees: 1GLOBE BIOMEDICAL CO., LTD., Beijing (CN); 1GLOBE HEALTH INSTITUTE LLC, Norwood, MA (US)

( * ) Notice: Subject to any disclaimer, the term of this patent is extended or adjusted under 35 U.S.C. 154(b) by 884 days.

(21) Appl. No.: 17/270,034

(22) PCT Filed: Aug. 20, 2019

(86) PCT No.: PCT/CN2019/101659
§ 371 (c)(1),
(2) Date: Feb. 21, 2021

(87) PCT Pub. No.: WO2020/038379
PCT Pub. Date: Feb. 27, 2020

(65) Prior Publication Data
US 2021/0332138 A1 Oct. 28, 2021

Related U.S. Application Data

(60) Provisional application No. 62/720,015, filed on Aug. 20, 2018.

(51) Int. Cl.
*C07K 16/28* (2006.01)
*A61K 45/06* (2006.01)

(52) U.S. Cl.
CPC .......... *C07K 16/2827* (2013.01); *A61K 45/06* (2013.01); *C07K 2317/21* (2013.01); *C07K 2317/52* (2013.01); *C07K 2317/56* (2013.01); *C07K 2317/732* (2013.01); *C07K 2317/734* (2013.01); *C07K 2317/76* (2013.01); *C07K 2317/92* (2013.01)

(58) Field of Classification Search
CPC ................ C07K 16/2827; C07K 2317/56
See application file for complete search history.

(56) References Cited

U.S. PATENT DOCUMENTS

| | | |
|---|---|---|
| 8,383,796 B2 | 2/2013 | Korman et al. |
| 10,011,656 B2 | 7/2018 | Freeman et al. |
| 2010/0068135 A1 | 3/2010 | Rock |
| 2013/0323249 A1 | 12/2013 | Zhou et al. |
| 2015/0355184 A1 | 12/2015 | Pierce et al. |
| 2016/0326264 A1 | 11/2016 | Gros et al. |
| 2017/0022273 A1 | 1/2017 | Zhou et al. |
| 2017/0182161 A1 | 6/2017 | Zhou et al. |
| 2017/0218066 A1 | 8/2017 | Zhou |
| 2018/0346574 A1 | 12/2018 | Fang et al. |
| 2020/0140554 A1* | 5/2020 | Zheng ............... A61P 31/12 |
| 2021/0388049 A1* | 12/2021 | Li ..................... C07K 16/2827 |

FOREIGN PATENT DOCUMENTS

| | | |
|---|---|---|
| CN | 106432501 A | 2/2017 |
| WO | WO2010/077634 A1 | 7/2010 |
| WO | WO2011/066389 A1 | 6/2011 |
| WO | WO2013/079174 A1 | 6/2013 |

OTHER PUBLICATIONS

Dermani et al. J Cell Physiol 234:1313-15 (Year: 2019).*
Lieping Chen et al. "Antisndash;PD-1/PD-L1 therapy of human cancer: past, present, and future", The Journal of Clinical Investigation, 125(9): 3384-3391 (2015).
K. Adachi et al. "Immune checkpoint blockade opens an avenue of cancer immunotherapy with a potent clinical efficacy," Cancer Sci 106(2015): 945-950.
ISA(CN), Internatioal Search Report in parent application PCT/CN2019/101659, issued Nov. 19, 2019.
CNIPA, search report in corresponding Chinses applictaion No. 201980054723.0, mailed Mar. 10, 2022.
EPO, extended European search report in corresponding EP Application No. 19853152.7, mailed Jul. 2022.
JPO, first official action in corresponding Japanese Patent Application No. 2021-509199, including reference list, mailed Aug. 2023.
IP Australia, Examination report No. 1 in corresponding Australian Patent Application No. 2019324388, mailed Dec. 21, 2023.
Canadian IP Office, first official action in corresponding Canadian Patent Application No. 3,110,138, mailed Jan. 30, 2024.
Rospatent, first official action in corresponding Russian Patent Application No. 2021104301, mailed Mar. 17, 2023, in English.
Taiwan IP Bureau, first official action in corresponding Taiwan Patent application No. 108129705, mailed May 23, 2023.

* cited by examiner

*Primary Examiner* — Karen A. Canella
(74) *Attorney, Agent, or Firm* — Milstein Zhang & Wu LLC; Duan Wu, Esq.

(57) ABSTRACT

Provided are compositions and methods relating to or derived from anti-PD-L1 antibodies with ADCC and/or CDC activities. More specifically, provided are fully human antibodies that bind PD-L1, PD-L1-binding antibody fragments, derivatives of such antibodies, and PD-L1-binding polypeptides comprising such fragments.

14 Claims, 26 Drawing Sheets
Specification includes a Sequence Listing.

| Code | Indirect ELISA (hPDL1-Fc) | Indirect ELISA (Fc Protein) | Ratio |
|---|---|---|---|
| | 1:10 dilution | 1:10 dilution | hPDL1-Fc/Fc protein |
| 3-1D2 | 0.4806 | 0.1678 | 2.9 |
| 3-1G2 | 1.5331 | 0.1756 | 8.7 |
| 3-1H2 | 2.6763 | 0.0907 | 29.5 |
| 3-1E3 | 1.8786 | 0.0572 | 32.8 |
| 3-1F4 | 1.2902 | 0.1539 | 8.4 |
| 3-1F4 | 2.356 | 0.0856 | 27.5 |
| 3-1H4 | 0.322 | 0.053 | 6.1 |
| 3-1G6 | 0.9759 | 0.0639 | 15.3 |
| 3-1A8 | 2.6098 | 0.1629 | 16.0 |
| 3-1D9 | 2.4438 | 0.0657 | 37.2 |
| 3-1B11 | 1.9688 | 0.0977 | 20.2 |
| 4-1A2 | 2.6675 | 0.0615 | 43.4 |
| 4-1B3 | 1.6244 | 0.0944 | 17.2 |
| 4-1F3 | 2.131 | 0.1901 | 11.2 |
| 4-1H3 | 1.7804 | 0.0588 | 30.3 |
| 4-1C4 | 1.164 | 0.0618 | 18.8 |
| 4-1G5 | 1.2259 | 0.2658 | 4.6 |
| 4-1H6 | 1.3997 | 0.0723 | 19.4 |
| 4-1G7 | 2.0743 | 0.0952 | 21.8 |
| 4-1E8 | 2.6675 | 0.0663 | 40.2 |
| 4-1B9 | 2.5715 | 0.0998 | 25.8 |
| 4-1C9 | 1.3074 | 0.0834 | 15.7 |
| 4-1H10 | 2.4456 | 0.0895 | 27.3 |
| 4-1A11 | 0.8698 | 0.0876 | 9.9 |
| 4-1A12 | 2.6959 | 0.0664 | 40.6 |
| 4-1B12 | 2.6846 | 0.0894 | 30.0 |
| NC | 0.0503 | 0.0534 | |

FIG. 3

| Code | MFI | | Ratio |
|---|---|---|---|
| | hPDL1/293T | 293T | hPDL1/293T vs. 293T |
| 3-1D2 | 89 | 28 | 3.2 |
| 3-1G2 | 52 | 33 | 1.6 |
| 3-1H2 | 120 | 32 | 3.8 |
| 3-1E3 | 157 | 35 | 4.5 |
| 3-1E4 | 91 | 28 | 3.3 |
| 3-1F4 | 161 | 35 | 4.6 |
| 3-1H4 | 95 | 47 | 2.0 |
| 3-1G6 | 49 | 29 | 1.7 |
| 3-1A8 | 386 | 26 | 14.8 |
| 3-1D9 | 86 | 28 | 3.1 |
| 3-1B11 | 178 | 39 | 4.6 |
| 4-1A2 | 733 | 39 | 18.8 |
| 4-1B3 | 185 | 40 | 4.6 |
| 4-1F3 | 89 | 36 | 2.5 |
| 4-1H3 | 74 | 35 | 2.1 |
| 4-1C4 | 101 | 31 | 3.3 |
| 4-1G5 | 100 | 43 | 2.3 |
| 4-1H6 | 149 | 40 | 3.7 |
| 4-1G7 | 193 | 35 | 5.5 |
| 4-1E8 | 849 | 39 | 21.8 |
| 4-1B9 | 111 | 39 | 2.8 |
| 4-1C9 | 151 | 26 | 5.8 |
| 4-1H10 | 102 | 31 | 3.3 |
| 4-1A11 | 43 | 28 | 1.5 |
| 4-1A12 | 683 | 47 | 14.5 |
| 4-1B12 | 280 | 29 | 9.7 |
| PC | 12315 | | |
| NC | 35 | | |

FIG. 4

| Code | 1:2 dilution | inhibition rate(%) |
|---|---|---|
| 4-1E8 | 0.1355 | 94.3 |
| 4-1A12 | 0.1453 | 93.9 |
| 4-1G7 | 0.166 | 93.0 |
| 4-1A2 | 0.2382 | 90.0 |
| 4-1B9 | 0.5471 | 76.9 |
| 4-1B12 | 0.6111 | 74.3 |
| 4-1H10 | 0.6749 | 71.6 |
| 3-1B11 | 0.9586 | 59.6 |
| 3-1E4 | 1.3562 | 42.9 |
| 3-1A8 | 1.4935 | 37.1 |
| 3-1H2 | 1.7556 | 26.0 |
| 4-1G5 | 1.9666 | 17.1 |
| 3-1F4 | 2.0946 | 11.1 |
| 4-1A11 | 2.2841 | 3.9 |
| 4-1C9 | 2.3193 | 2.3 |
| 3-1E3 | 2.3195 | 2.3 |
| 4-1H6 | 2.3718 | 0.1 |
| 4-1B3 | 2.386 | -0.5 |
| 4-1F3 | 2.3923 | -0.8 |
| 3-1D9 | 2.4153 | -1.8 |
| 4-1C4 | 2.5006 | -5.4 |
| 4-1H3 | 2.6041 | -9.7 |
| 3-1G6 | 2.7208 | -14.6 |
| 3-1D2 | 2.7965 | -17.8 |
| 3-1G2 | 2.8253 | -19.0 |
| 3-1H4 | 2.8979 | -22.1 |
| PC | 2.3733 | |
| NC | 0.0589 | |

FIG. 5

| Code | 1:2 dilution | Inhibition rate(%) |
|---|---|---|
| 4-1A12 | 0.099 | 95.3 |
| 4-1G7 | 0.1223 | 94.2 |
| 4-1E8 | 0.1795 | 91.5 |
| 4-1H10 | 0.2274 | 89.3 |
| 4-1B9 | 0.2373 | 88.8 |
| 4-1A2 | 0.2495 | 88.2 |
| 4-1B12 | 0.3233 | 84.8 |
| 3-1B11 | 0.3494 | 83.5 |
| 3-1E4 | 0.5115 | 75.9 |
| 3-1H2 | 0.5519 | 74.0 |
| 4-1G5 | 0.7667 | 63.9 |
| 3-1A8 | 0.8139 | 61.6 |
| 4-1F3 | 0.9102 | 57.1 |
| 4-1C9 | 0.9241 | 56.4 |
| 3-1F4 | 1.1417 | 46.2 |
| 4-1B3 | 1.1561 | 45.5 |
| 4-1H6 | 1.3543 | 36.2 |
| 3-1G6 | 1.3567 | 36.1 |
| 4-1C4 | 1.4423 | 32.0 |
| 3-1D2 | 1.544 | 27.2 |
| 3-1D9 | 1.585 | 25.3 |
| 3-1E3 | 1.7194 | 19.0 |
| 3-1H4 | 1.8486 | 12.9 |
| 4-1A11 | 1.9063 | 10.2 |
| 3-1G2 | 2.0271 | 4.5 |
| 4-1H3 | -- | -- |
| PC | 2.1217 | |
| NC | 0.04995 | |

FIG. 6

M: Marker

5: 4-1E8 (1ug)

| Antibody Code | RBA(IC50, nM) PD1 coated | RBA(IC50, nM) PDL1 coated | ELISA (EC50, nM) | FACS (EC50, nM) |
|---|---|---|---|---|
| 4-1B8 | 1.257 | 1.531 | 0.0391 | 0.3558 |
| 3-1B11 | 1.389 | 0.7955 | 0.018 | 0.1318 |
| 4-1G7 | 2.672 | 2.948 | 0.04471 | 0.791 |
| 21-A1 | 2.714 | 2.943 | 0.0398 | 0.6253 |
| 4-1A2 | 3.305 | 5.91 | 0.0203 | 0.5009 |
| 11-A4 | 3.82 | 3.988 | 0.0183 | 0.436 |
| 4-1G5 | 7.372 | 8.564 | 0.0147 | 0.8547 |
| 4-1A12 | 9.488 | 5.921 | 0.105 | 0.5497 |
| 4-1B3 | 17.46 | 9.866 | 0.0284 | 0.4173 |
| 14-G10 | 26.79 | 11.88 | 0.3345 | 6.17 |
| 3-1H2 | 29.96 | 5.828 | 0.0539 | 0.8214 |
| 4-1B12 | 43.91 | 337.6 | 0.1531 | 1.195 |
| 7-D12 | 52.36 | 12.2 | 0.0744 | 0.9859 |
| 10-A6 | 57.14 | 25.11 | 0.323 | 7.06 |
| 4-1C9 | 59.97 | 19.67 | 0.0777 | 2.312 |
| 21-G1 | 70.45 | 10.33 | 0.0642 | 4.488 |
| 3-1E4 | 91.74 | 16.57 | 0.3997 | 3.145 |
| 4-1B9 | 98.78 | 112.4 | 0.0809 | 4.702 |
| 3-1A8 | 100.7 | 82.29 | 0.6715 | 8.168 |
| 21-H12 | 145.4 | 23.71 | 0.056 | 0.7875 |
| 4-1F3 | 196.7 | 36.13 | 0.5627 | 8.469 |
| 4-1H10 | 212 | 20.91 | 0.0828 | 0.3229 |
| 35-B1 | - | - | 4.671 | 10.93 |
| 12-A4 | - | 344.2 | 0.2394 | 5.516 |
| 22-A6 | - | - | 0.4816 | 8.95 |
| 9-E8 | - | - | - | - |
| 3-1F4 | ~974967 | ~511744 | 0.0635 | 1.178 |

FIG. 15

| Antibody Code | ka (1/Ms) | kd (1/s) | KD (M) |
|---|---|---|---|
| 4-1E8 | 5.56E+05 | 2.48E-03 | 4.46E-09 |
| 4-1G7 | 8.26E+04 | 3.63E-03 | 4.39E-08 |
| 4-1A2 | 5.24E+05 | 2.55E-03 | 4.88E-09 |
| 21-A1 | 5.02E+05 | 2.19E-03 | 4.36E-09 |
| 7-D12 | 1.28E+06 | 1.00E-02 | 7.82E-09 |
| 11-A4 | 4.03E+05 | 2.89E-03 | 7.16E-09 |
| 4-1G5 | 5.01E+04 | 6.63E-03 | 1.32E-07 |
| 4-1B3 | 4.20E+05 | 4.47E-03 | 1.06E-08 |
| 3-1B11 | 4.11E+05 | 9.54E-04 | 2.32E-09 |
| 3-1H2 | 5.45E+05 | 5.97E-03 | 1.10E-08 |

Percent Inhibition of Binding

| Competitive Ab | Coating Ab | | | | | | | | | |
|---|---|---|---|---|---|---|---|---|---|---|
| | 4-1E8 | 4-1A2 | 3-1B11 | 11-A4 | 21-A1 | 4-1G7 | 4-1G5 | 4-1B3 | 7-D12 | 3-1H2 |
| 4-1E8 | 94% | 94% | 94% | 95% | 94% | 93% | 96% | 96% | 96% | 96% |
| 4-1A2 | 77% | 74% | 67% | 88% | 89% | 85% | 91% | 92% | 93% | 92% |
| 3-1B11 | 89% | 89% | 88% | 94% | 93% | 93% | 95% | 95% | 95% | 95% |
| 11-A4 | 80% | 78% | 79% | 93% | 91% | 90% | 95% | 93% | 95% | 94% |
| 21-A1 | 91% | 88% | 91% | 94% | 95% | 94% | 95% | 95% | 96% | 95% |
| 4-1G7 | 88% | 85% | 87% | 93% | 94% | 93% | 95% | 94% | 96% | 94% |
| 4-1G5 | 71% | 66% | 65% | 82% | 87% | 79% | 88% | 89% | 91% | 90% |
| 4-1B3 | 52% | 49% | 45% | 76% | 83% | 76% | 87% | 87% | 90% | 89% |
| 7-D12 | 47% | 38% | 45% | 70% | 78% | 74% | 86% | 80% | 87% | 85% |
| 3-1H2 | 55% | 44% | 38% | 63% | 67% | 70% | 80% | 71% | 77% | 88% |

FIG. 18A Unstained   FIG. 18B 4-1E8   FIG. 18C 3-1E4   FIG. 18D 3-1B11

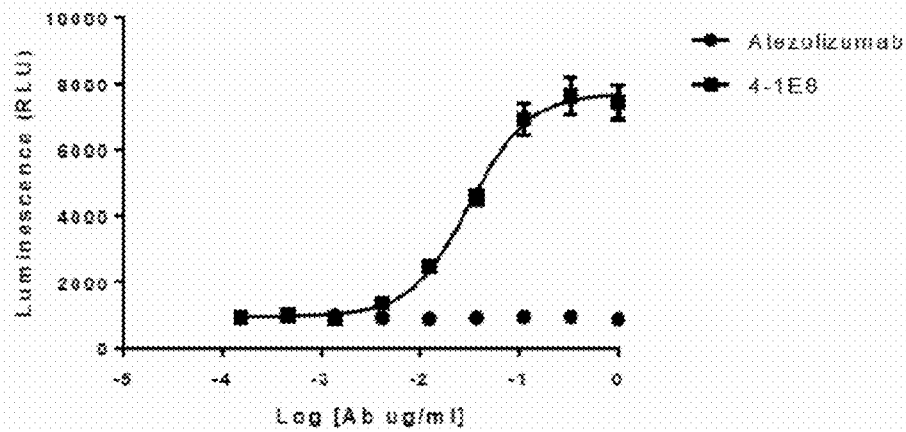
FIG. 21
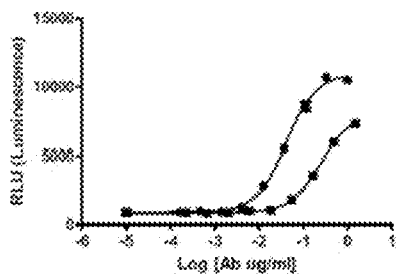
FIG. 22A
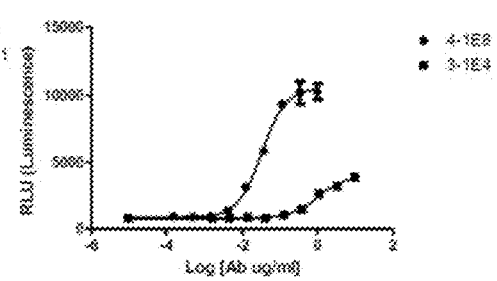
FIG. 22B
| Antibody | EC50 (ug/mL) | SD | Replicates |
|---|---|---|---|
| 4-1E8 | 0.034 | 0.005 | 7 |
| 3-1B11 | 0.210 | 0.048 | 2 |
| 3-1E4 | 0.801 | 0.325 | 2 |
FIG. 22C

ANTI-PD-L1 CANCER IMMUNOTHERAPY ANTIBODIES

CROSS REFERENCE TO RELATED APPLICATIONS

This application is a national phase application under 35 U.S.C. 371 of international application PCT/CN2019/101659, filed Aug. 20, 2019 which claims priority to and the benefit of U.S. Provisional Patent Application Ser. No. 62/720,015 filed Aug. 20, 2018, the entire content of which is incorporated herein by reference in its entirety.

REFERENCE TO SEQUENCE LISTING

Sequence listings and related materials in the ASCII text file named "Seq-007PCT.txt" and created on Feb. 16, 2021 with a size of about 91 kilobytes, is hereby incorporated by reference.

FIELD OF THE INVENTION

The present invention relates to antigen-binding polypeptides that bind human PD-L1, pharmaceutical compositions and uses thereof. Aspects of the invention also relate to expression system producing such antigen-binding polypeptides or antibodies. The described antigen-binding polypeptides or pharmaceutical compositions of the invention are useful for treating a subject in need thereof for a pathological condition, such as a mammalian cancer, an infection, and so on.

BACKGROUND OF INVENTION

Immune cells have costimulatory and inhibitory receptors on their cell surfaces that interact with membrane-bound and soluble ligands. These receptors serve to regulate the potency, duration, and type of the immune response by altering thresholds and the durations of immune cell activation or inhibition. These are often referred collectively to as immune checkpoints. Many of these checkpoint molecules are members of either the B7 superfamily or tumor necrosis factor (TNF) superfamily of molecules.

The B7 family includes both inhibitory and stimulatory co-receptors. For example, on the one hand, ligation of Programmed (Cell) Death Protein 1 (PD-1) and Cytotoxic T-Lymphocyte-Associated Protein 4 (CTLA-4) with their respective ligands (PD-L1, PD-L2 and B7-1, B7-2, respectively) leads to suppression of the activation or generation of regulatory T cells, anergy, exhaustion and apoptosis. On the other hand, ligation of Cluster of Differentiation (CD28) and Inducible T-cell COStimulator (ICOS) receptors with their respective ligands results in increased proliferation and production of cytokine. In contrast, the TNF family of costimulatory receptors includes only stimulatory molecules such as OX40, 4-1BB, CD40, CD27 and their ligands that favor proliferation and effector function differentiation. In addition, there are other co-receptors that do belong to either of these families e.g., Tim-3, LAG-3, Ceacam-1, etc.

For the past couple of decades, it has become clear that many types of cancer generate an immunosuppressive environment within the tumor through a variety of mechanisms. A recurrent theme is the ectopic expression of an inhibitory immune checkpoint ligand (especially PDL1) that suppresses intratumoral T cells. There is also increasing evidence that blocking this tumor mediated immunity suppression can de-repress intratumoral T cells and allow them to kill the tumor (Adachi K, Tamada K. *Cancer Sci.* 2015; 106(8):945-50; Rafiq S, et al., *Nat Biotechnol.* 2018 Aug. 13; Hargadon K M, et al., *Int Immunopharmacol.* 2018; 62:29-39). Blocking can be done through an antibody or a variety of other methods. This is different from traditional anticancer antibody therapy where the antibody binds to the cancer cell and recruits complement dependent cytotoxicity (CDC) as well as antibody-dependent cellular cytotoxicity (ADCC) to directly kill the tumor cells.

CTLA-4 antibodies were the first of a class of immunotherapeutics based on immune checkpoint blockade to win FDA approval. Other blockade targets, such as PD1 and its associated molecules, offer more and different opportunities for enhancing the antitumor immunity in a clinical setting.

BRIEF SUMMARY OF THE INVENTION

The present invention provides antigen-binding polypeptides that bind PD-L1 (or, interchangeably, "anti-PD-L1 polypeptide(s)," "PD-L1-binding polypeptides"), preferably, the human PD-L1; the polypeptide has one or both of the following features: (a) binds to PD-L1 and inhibits its ability to interact with PD1; and (b) has an isotype or constant region that can trigger ADCC and/or CDC. The resulting antibody can kill tumor cells through two synergistic pathways—T cell de-repression and direct cytotoxicity. The polypeptides of the present invention can be used to treat tumors by itself or in combination with (a) antibodies targeting other immunosuppressive pathways; (b) chemotherapy or radiation therapy; (c) other mechanisms of blocking immunosuppressive pathways, e.g., aptamers or RNAi; or (d) other immunotherapy agents, e.g. cytokines, targeted therapeutics, etc.

In one aspect, the present invention provides an antigen-binding polypeptide, e.g., an antibody, fragment, derivative or analog thereof, that is of the IgG1 isotype and binds to a PD-L1 epitope, preferably with a binding affinity of at least $10^{-6}$M, and having a heavy chain variable domain sequence "consisting essentially of," meaning herein, that is at least 80%, or, more preferably, 85%, 90%, 95%, or even 100%, identical to the amino acid sequences selected from the group consisting of SEQ ID NO:2, SEQ ID NO:6, SEQ ID NO:10, SEQ ID NO:14, SEQ ID NO:18, SEQ ID NO:22, SEQ ID NO:26, SEQ ID NO:30, SEQ ID NO:34, SEQ ID NO:38, SEQ ID NO:42, SEQ ID NO:46, SEQ ID NO:50, SEQ ID NO:54, SEQ ID NO:58, SEQ ID NO:62, SEQ ID NO:66, SEQ ID NO:70, SEQ ID NO:74, SEQ ID NO:78, SEQ ID NO:82, SEQ ID NO:86, SEQ ID NO:90, SEQ ID NO:94, SEQ ID NO:98, SEQ ID NO:102, SEQ ID NO:106, and combinations thereof, and that having a light chain variable domain sequence consisting essentially of, meaning, that is at least 80%, or, more preferably, 85%, 90%, 95%, or even 100%, identical to the amino acid sequences selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO: 76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, and combinations thereof.

In preferred embodiments, an antigen-binding polypeptide or antibody of the invention includes a pair of heavy chain variable region and light chain variable region where their respective sequences consist essentially of the following pairing: (a) SEQ ID NO:18 and SEQ ID NO:20; (b) SEQ ID NO:42 and SEQ ID NO:44; or (c) SEQ ID NO:34 and SEQ ID NO:36.

In other preferred embodiments, an antigen-binding polypeptide or antibody of the invention includes a pair of heavy chain variable region and light chain variable region where their respective sequences consist essentially of the following pairing: (a) SEQ ID NO:22 and SEQ ID NO:24; (b) SEQ ID NO:2 and SEQ ID NO:4; (c) SEQ ID NO:62 and SEQ ID NO:64; or (d) SEQ ID NO:82 and SEQ ID NO:84.

In other preferred embodiments, an antigen-binding polypeptide or antibody of the invention includes a pair of heavy chain variable region and light chain variable region where their respective sequences consist essentially of the following pairing: (a) SEQ ID NO:70 and SEQ ID NO:72; (b) SEQ ID NO:50 and SEQ ID NO:52; (c) SEQ ID NO:102 and SEQ ID NO:104; or (d) SEQ ID NO:30 and SEQ ID NO:32.

In other preferred embodiments, an antigen-binding polypeptide or antibody of the invention includes a pair of heavy chain variable region and light chain variable region where their respective variable region sequences consist essentially of the following pairing: (a) SEQ ID NO:6 and SEQ ID NO:8; (b) SEQ ID NO:10 and SEQ ID NO:12; (c) SEQ ID NO:14 and SEQ ID NO:16; (d) SEQ ID NO:26 and SEQ ID NO:28; (e) SEQ ID NO:38 and SEQ ID NO:40; (f) SEQ ID NO:46 and SEQ ID NO:48; (g) SEQ ID NO:54 and SEQ ID NO:56; or (h) SEQ ID NO:58 and SEQ ID NO:60.

In other preferred embodiments, an antigen-binding polypeptide or antibody of the invention includes a pair of heavy chain variable region and light chain variable region where their respective variable region sequences consist essentially of the following pairing: (a) SEQ ID NO:66 and SEQ ID NO:68; (b) SEQ ID NO:74 and SEQ ID NO:76; (c) SEQ ID NO:78 and SEQ ID NO:80; (d) SEQ ID NO:86 and SEQ ID NO:88; (e) SEQ ID NO:90 and SEQ ID NO:92; (f) SEQ ID NO:94 and SEQ ID NO:96; (g) SEQ ID NO:98 and SEQ ID NO:100; or (h) SEQ ID NO:106 and SEQ ID NO:108.

Preferably, the antigen-binding polypeptide is fully human or otherwise humanized. In a preferred embodiment, the antigen-binding polypeptide further comprising a human constant region. In one feature, the human constant region is IgG1. In some embodiments, the antibody of the invention further includes a second pair of heavy and light chain variable regions that are, e.g., substantially identical to the first pair.

In a preferred version, the binding of the anti-PD-L1 polypeptide to PD-L1 blocks PD-L1's interaction with PD1. This could be either because the epitope for the binding on PD-L1 is at or near the PD1 interaction interface or because there is an allosteric change in the conformation of the PD1 interaction interface.

In another aspect, the present invention provides nucleic acid molecules that encode the above mentioned polypeptides. The nucleic acid molecule can be a DNA molecule or RNA molecule. In a preferred embodiments, the nucleic acid molecule is a DNA molecule that encodes a heavy chain variable region and a light chain variable region of an antigen-binding polypeptide or antibody of the invention, wherein the DNA sequences respectively consist essentially of the following pairing: (a) SEQ ID NO:17 and SEQ ID NO:19; (b) SEQ ID NO:33 and SEQ ID NO:35; (c) SEQ ID NO:41 and SEQ ID NO:43.

In other preferred embodiments, the nucleic acid molecule is a DNA molecule that encodes a heavy chain variable region and a light chain variable region of an antigen-binding polypeptide or antibody of the invention, wherein the DNA sequences respectively consist essentially of the following pairing: (a) SEQ ID NO:21 and SEQ ID NO:23; (b) SEQ ID NO:1 and SEQ ID NO:3; (c) SEQ ID NO:61 and SEQ ID NO:63; or (d) SEQ ID NO:81 and SEQ ID NO:83.

In other preferred embodiments, the nucleic acid molecule is a DNA molecule that encodes a heavy chain variable region and a light chain variable region of an antigen-binding polypeptide or antibody of the invention, wherein the DNA sequences respectively consist essentially of the following pairing: (a) SEQ ID NO:69 and SEQ ID NO:71; (b) SEQ ID NO:49 and SEQ ID NO:51; (c) SEQ ID NO:101 and SEQ ID NO:103; or (d) SEQ ID NO:29 and SEQ ID NO:31.

In other preferred embodiments, the nucleic acid molecule is a DNA molecule that encodes a heavy chain variable region and a light chain variable region of an antigen-binding polypeptide or antibody of the invention, wherein the DNA sequences respectively consist essentially of the following pairing: (a) SEQ ID NO:5 and SEQ ID NO:7; (b) SEQ ID NO:9 and SEQ ID NO:11; (c) SEQ ID NO:13 and SEQ ID NO:15; (d) SEQ ID NO:25 and SEQ ID NO:27; (e) SEQ ID NO:37 and SEQ ID NO:39; (f) SEQ ID NO:45 and SEQ ID NO:47; (g) SEQ ID NO:53 and SEQ ID NO:55; or (h) SEQ ID NO:57 and SEQ ID NO:59.

In other preferred embodiments, the nucleic acid molecule is a DNA molecule that encodes a heavy chain variable region and a light chain variable region of an antigen-binding polypeptide or antibody of the invention, wherein the DNA sequences respectively consist essentially of the following pairing: (a) SEQ ID NO:65 and SEQ ID NO:67; (b) SEQ ID NO:73 and SEQ ID NO:75; (c) SEQ ID NO:77 and SEQ ID NO:79; (d) SEQ ID NO:85 and SEQ ID NO:87; (e) SEQ ID NO:89 and SEQ ID NO:91; (f) SEQ ID NO:93 and SEQ ID NO:95; (g) SEQ ID NO:97 and SEQ ID NO:99; or (h) SEQ ID NO:105 and SEQ ID NO:107.

In another aspect, the present invention provides a pharmaceutical composition that includes an antigen-binding polypeptide, e.g., the anti-PD-L1 antibody, fragment, derivative or analog, as disclosed herein. The pharmaceutical composition further includes a pharmaceutically acceptable excipient, carrier, or diluent.

In a related aspect, the present invention provides a method of treating a subject in need thereof for a pathological condition therapeutically, said method comprising administering to said subject a therapeutically effective amount of the anti-PD-L1 polypeptide or antibody disclosed herein. The method may further include a step of administering a second and different therapeutic antibody against at least one cell-surface antigen indicative of said condition. The condition being treated may be a mammalian cancer, an infection, and so on. In various embodiments, the anti-PD-L1 polypeptide may be an antibody, an antibody fragment, an antibody derivative or an antibody analog.

Preferably, the spectrum of mammalian cancers to be treated is selected from the group consisting of ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, mast cell derived tumors, melanoma, bladder cancer, gastric cancer, liver cancer, urothelial carcinoma, cutaneum carcinoma, renal cancer, head and neck cancer, pancreatic cancer, and combinations thereof. More broadly, any cancer where at least a significant fraction of the tumor cells express detectable amount of PD-L1 is contemplated as targets to be treated by the composition of the present invention.

In yet another aspect, the invention provides a method of treating a subject in need thereof for similar conditions prophylactically, said method comprising administering to said subject a prophylactically effective amount of the pharmaceutical composition of the invention. The method may further include a step of administering a vaccine against said condition. In one embodiment, the condition is a cancer.

In a further aspect, the invention provides a mammalian expression system that produces the antigen-binding polypeptide, e.g., an antibody, fragment, derivative or analog thereof, that binds to a PD-L1 epitope described herein.

BRIEF DESCRIPTION OF FIGURES

FIG. 3 is a chart listing data that characterize the ability to bind hPDL1 of representative single chain variable fragments (scfv) obtained through an embodiment of present invention in indirect ELISA binding assay. "NC" represents negative control.

FIG. 4 is a chart listing data that characterize the ability to bind hPDL1 of representative single chain variable fragments (scfv) obtained through an embodiment of present invention in FACS binding assay. "PC" represents positive control using hPDL1/293T cells stained with anti-hPDL1-APC (10 µg/ml). "NC" represents negative control with unstained hPDL1/293T cells.

FIG. 5 is a chart listing data that characterize the ability to block the interaction between hPD1 and hPDL1 of various single chain variable fragments (scfv) obtained through an embodiment of present invention in receptor blocking assay (plates coated by hPDL1). "PC" represents positive control with added biotin-hPD1-Fc. "NC" represents negative control where only buffer was added.

FIG. 6 is a chart listing data that characterize the ability to block the interaction between hPD1 and hPDL1 of various single chain variable fragments (scfv) obtained through an embodiment of present invention in receptor blocking assay (plates coated by hPD1). "PC" represents positive control with added biotin-hPDL1-Fc. "NC" represents negative control where only buffer was added.

FIG. 15 is a chart listing data that characterizes various full-length antibodies obtained through an embodiment of the present invention.

FIG. 16A schematically depicts the BIAcore format utilized according to an example of the present invention; FIG. 16B lists results from testing lead antibody candidates≤ affinity to PD-L1 using BIAcore; FIG. 16C depicts the response curve of antibody coded 4-1E8 of BIAcore affinity testing; and FIG. 16D depicts the response curve of antibody coded 3-1B11 of BIAcore affinity testing.

FIGS. 18A-18D show binding abilities of: controls (FIG. 18A), antibodies of the invention coded "4-1E8" (FIG. 18B), "3-1E4" (FIG. 18C), and "3-1B11" (FIG. 18D) to Rhesus PDL1-GFP expressing construct transfected 293T cell (top) and parental 293T (bottom) cells through FACS assays.

FIGS. 19A-19D show binding abilities of: controls (FIG. 19A), antibodies of the invention coded "4-1E8" (FIG. 19B), "3-1E4" (FIG. 19C), and "3-1B11" (FIG. 19D) to Rhesus PDL1 expressing construct transfected 293T cell (top) and parental 293T (bottom) cells through FACS assays.

FIG. 21 shows ADCC activity of the polypeptide embodiment coded "4-1E8" in comparison to commercially available anti-PDL1 antibody Atezolizumab.

FIGS. 22A-22C show ADCC activity of the polypeptide embodiment coded "4-1E8" in comparison to embodiments coded "3-1B11" (FIG. 22A) and "3-1E4" (FIG. 22B), with key data points summarized in a chart (FIG. 22C).

DETAILED DESCRIPTION OF INVENTION

Figure 1:
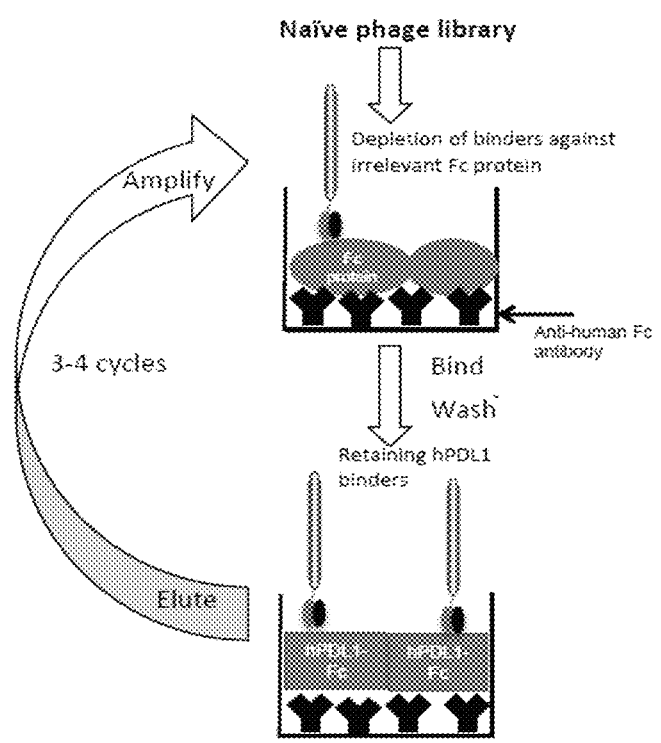
FIG. 1 schematically depicts screening for antigen-binding polypeptides with solid phase phage panning technologies, specifically, using indirect coating of test proteins to the immunotubes, according to an embodiment of the present invention.

Unless otherwise noted, technical terms are used according to conventional usage.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5 to 10% of the recited value) that one of ordinary skill in the art would consider equivalent to the recited value (e.g., having the same function or result). In some instances, the term "about" may include numerical values that are rounded to the nearest significant figure. Unless indicated otherwise, "about" is +/−10% of the recited value(s).

An "antigen-binding polypeptide" is a polypeptide comprising a portion that binds to an antigen. Examples of antigen-binding polypeptides include antibodies, antibody fragments (e.g., an antigen binding portion of an antibody), antibody derivatives, and antibody analogs.

An antigen binding polypeptide or protein can have, for example, the structure of a naturally occurring antibody (also known as "immunoglobulin"). Each naturally occurring antibody is composed of two identical pairs of polypeptide chains, each pair having one "light" (about 25 kDa) and one "heavy" chain (about 50-70 kDa). The variable regions of each light/heavy chain pair form the antibody-binding site such that an intact antibody has two binding sites.

The variable regions of naturally occurring antibody chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest, 5th* Ed., US Dept. of Health and Human Services, PHS, NIH, NIH Publication no. 91-3242, 1991. Other numbering systems for the amino acids in immunoglobulin chains include IMGT (international ImMunoGeneTics information system; Lefranc et al., *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

The term "antibody" or "Ab" (and their plural forms), as used herein, broadly refers to any immunoglobulin (Ig) molecule comprised of four polypeptide chains, two heavy (H) chains and two light (L) chains, or any functional fragment(s), mutant(s), variant(s), derivative(s) or analog(s) thereof, which retains the essential and specific epitope-binding features of an Ig molecule. Such fragment, mutant, variant, derivative or analog antibody formats are known in the art, and include, inter alia, Fab, F(ab'), F(ab')$_2$, Fv, single-chain antibodies (scFv), single-domain antibodies (sdAbs), complementarity determining region (CDR) fragments, chimeric antibodies, diabodies, triabodies, tetrabodies, and polypeptides that contain at least a portion of an immunoglobulin that is sufficient to confer specific antigen binding to the polypeptide. Antibody fragments, derivatives and analogs may be produced by recombinant DNA techniques or by enzymatic or chemical cleavage of intact antibodies.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (see, e.g., U.S. Pat. Nos. 6,846,634; 6,696,245, US App. Pub. 20/0202512; 2004/0202995; 2004/0038291; 2004/0009507; 2003/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, where each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen-binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding polypeptide may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding polypeptide may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" or "humanized antibody" as used herein includes all antibodies that have one or more variable and constant regions derived from human immunoglobulin sequences. In one embodiment, all of the variable and constant domains are derived from human immunoglobulin sequences (a fully human or humanized antibody). These antibodies may be prepared in a variety of ways, including through the immunization with an antigen of interest of a mouse that is genetically modified to express antibodies derived from human heavy and/or light chain-encoding genes. A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" as used herein refers to an antibody that contains one or more regions from one antibody and one or more regions from at least another antibody. In an embodiment, the CDRs from more than one human anti-PD-L1 antibodies are mixed and matched in a chimeric antibody.

Activated T cells express PD1 on their cell surface. Binding of PD-L1 to PD1 activates PD1 and suppresses the $PD1^+$ T cells. A "neutralizing antibody" or an "inhibitory antibody" as used herein refers to an antibody that blocks the activation of PD1 when an excess of the anti-PD-L1 antibody reduces the amount of said activation by at least about 20% using an assay such as those described herein in the Examples. In various embodiments, the antigen binding protein reduces the amount of activation of PD1 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, Science 253:164.

As used herein, an antigen-binding polypeptide "specifically binds" to an antigen (e.g., human PD-L1) if it binds to the antigen with a dissociation constant of 100 nanomolar or less.

An "antigen binding domain," "antigen binding region," or "antigen binding site," as used herein, is a portion of an antigen binding protein that contains amino acid residues (or other moieties) that interact with an antigen and contribute to the antigen binding protein's specificity and affinity for the antigen. For an antibody to specifically bind to its antigen, it will include at least part of at least one of its CDR domains.

An "epitope" as used herein is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

As used herein, the terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutant, or variant thereof.

A "vector" as used herein is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

As used herein, a nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

Preferably, the broad spectrum of mammalian cancers to be treated by compositions of the present invention is selected from the group consisting of ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, mast cell derived tumors, melanoma, bladder cancer, gastric cancer, liver cancer, urothelial carcinoma, cutaneum carcinoma, renal cancer, head and neck cancer, pancreatic cancer, and combinations thereof. More broadly, any cancer where at least a fraction of the tumor cells express detectable amount of PD-L1 can potentially be treated by the composition of the invention.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for E. coli and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA of the present invention can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct of the present invention is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

PD-L1-binding polypeptides can also be produced by chemical synthesis (e.g., by the methods described in *Solid Phase Peptide Synthesis*, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 90% or 95% pure, and most preferably at least 98% pure. Regardless of the exact numerical value of the purity, the polypeptide is sufficiently purified for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76. Effects of such non-amino acid elements on the functionality of a polypeptide may be tested for its antagonizing role in PD-L1 or PD-1 function, e.g., its inhibitory effect on angiogenesis or on tumor growth.

In one embodiment, modified forms of the subject polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

In one feature, the pegylated embodiments of binding polypeptides of the invention preferably retain at least 25%, 50%, 60%, 70%, 80%, 90%, 95% or 100% of the biological activity associated with the unmodified protein. In one embodiment, biological activity refers to its ability to bind to PD-L1, as assessed by KD, $k_{on}$ or $k_{off}$ rates. In one specific embodiment, the pegylated binding polypeptide protein shows an increase in binding to human PD-L1 relative to the unpegylated counterpart. In another embodiment, the biological activity refers to blockage of PD-L1/PD1 interaction.

Therapeutics, Vaccines & Administration

The present disclosure further features methods for treating conditions or preventing pre-conditions which respond to inhibition of an PD-L1 biological activity. Preferred examples are conditions that are characterized by cellular hyperproliferation and sustained infection. Techniques and dosages for administration vary depending on the type of specific polypeptide and the specific condition being treated. Because regulatory agencies require that a protein reagent to be used as a therapeutic be formulated with acceptably low levels of pyrogens, therapeutic formulations of the present invention can be distinguished from other formulations for being substantially pyrogen free, or at least contain no more than acceptable levels of pyrogen as determined by the appropriate regulatory agency (e.g., U.S. FDA).

Pharmaceutical formulations of the present invention may include at least one pharmaceutically acceptable diluent, carrier, or excipient. Excipients included in the formulations will have different purposes depending, for example, on the kind of gene construct or effector cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

In another embodiment of the invention, a pharmaceutical formulation of the invention is administered into the patient. Exemplary administration modes include, but are not limited to, intravenous injection. Other modes include, without limitation, intratumoral, intradermal, subcutaneous (s.c., s.q., sub-Q, Hypo), intramuscular (i.m.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of the formulations can be used to effect such administration. As used herein, the terms "treat", "treating", and "treatment" have their ordinary and customary meanings, and include one or more of: blocking, ameliorating, or decreasing in severity and/or frequency a symptom of a disease (e.g., cancer) in a subject, and/or inhibiting the growth, division, spread, or proliferation of cancer cells, or progression of cancer (e.g., emergence of new tumors) in a subject. Treatment means blocking, ameliorating, decreasing, or inhibiting by about 5% to about 100% versus a subject in which the methods of the present invention have not been practiced. Preferably, the blocking, ameliorating, decreasing, or inhibiting is about 100%, 99%, 95%, 90%, 80%, 70%, 60%, 50%, 40%, 30%, 20%, 10%, or 5% versus a subject in which the methods of the present invention have not been practiced.

The invention also provides a kit comprising one or more containers filled with quantities of gene constructs encoding the polypeptides of the invention, with pharmaceutically acceptable excipients. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

EXAMPLES

Screening of Antigen-Binding Polypeptide Employing Phage Display Techniques:

Indirect coating: Referring to FIG. 1, PDL1-binding single chain variable fragments (scFv) were identified by standard phage display technique. Human naïve scFv libraries were generated through PCR-based reconstruction from B cells from 50 healthy donors. Solid phase immunotube-based panning was performed using hPDL1-Fc fusion protein and irrelevant Fc fusion protein indirectly immobilized onto immunotube coated with anti-human IgG Fc antibody. To pan for strong binders, Fc-binding scFvs were first depleted using the irrelevant Fc fusion proteins and then the unbound phages were selected for binding with the hPDL1-Fc fusion protein. Eluted phages were amplified in bacteria. These rounds were repeated 3-4 times and the phage titers and complexity was determined after the second round onwards. Once, convergence in sequence was seen (rounds 3 and 4), individual phage clones were tested for their ability to bind hPDL1 in ELISA assays.

Figure 2:
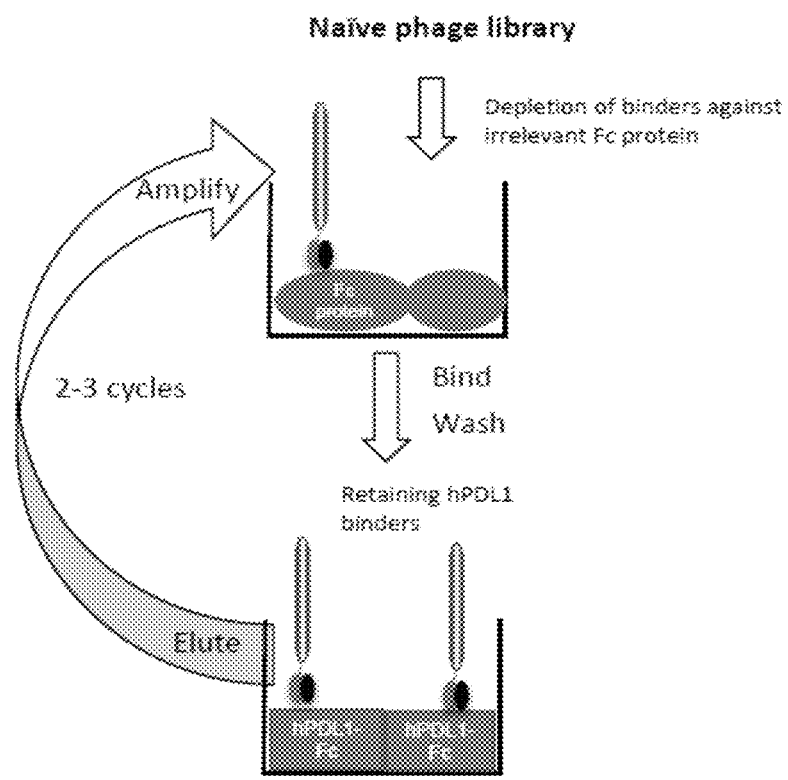
FIG. 2 schematically depicts screening for antigen-binding polypeptides with solid phase phage panning technologies, specifically, using direct coating of test proteins to the immunotubes, according to an embodiment of the present invention.

Direct coating: This was conducted by directly coating the Fc proteins onto the immunotube without the use of the anti-human Fc antibody (FIG. 2).

Figure 7:
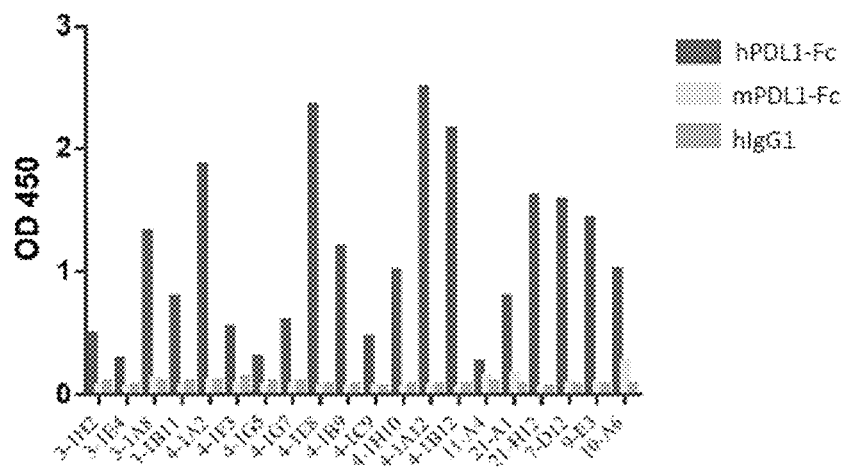
FIG. 7 depicts ability to bind hPDL1-Fc, mPDL1-Fc (mouse PDL1) and hIgG1 of the single chain variable fragments (scfv) obtained through embodiments of the present invention in direct ELISA assays.
Figure 8A:
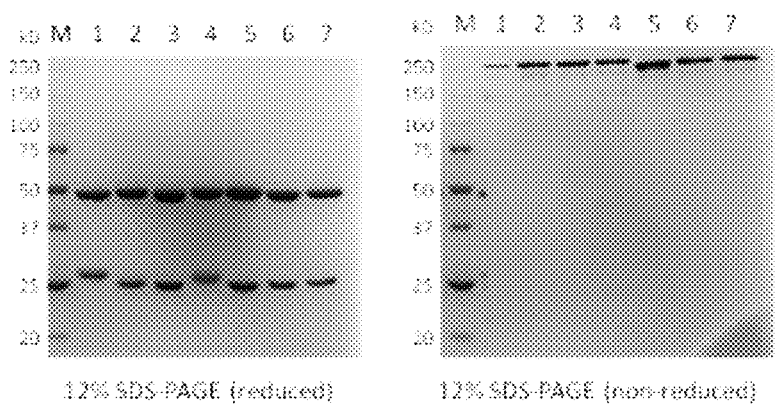
FIGS. 8A and 8B show full-length antibody 4-1E8 characterized by SDS-PAGE (FIG. 8A) and size exclusion chromatography (FIG. 8B).
Figure 8B:
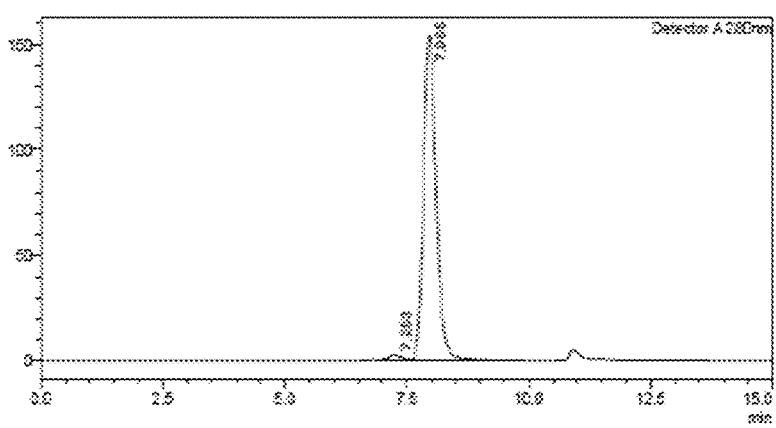
Figure 9A:
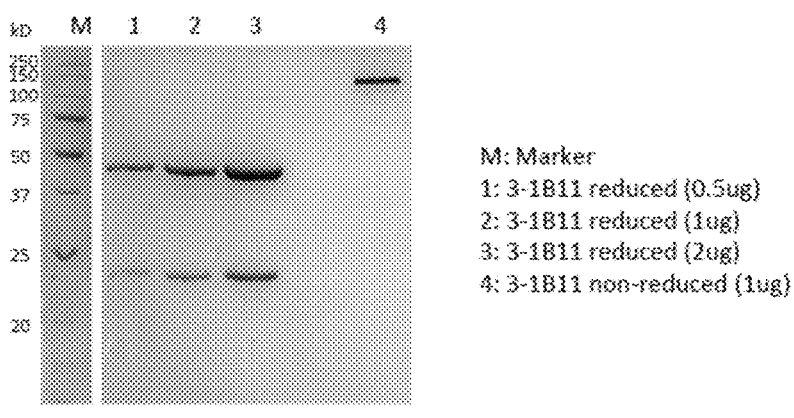
FIGS. 9A and 9B show full-length antibody 3-1B11 characterized by SDS-PAGE (FIG. 9A) and size exclusion chromatography (FIG. 9B).
Figure 9B:
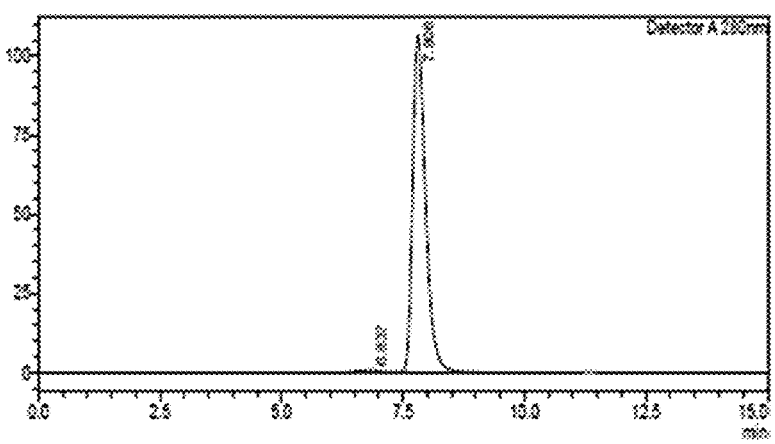
Figure 10A:
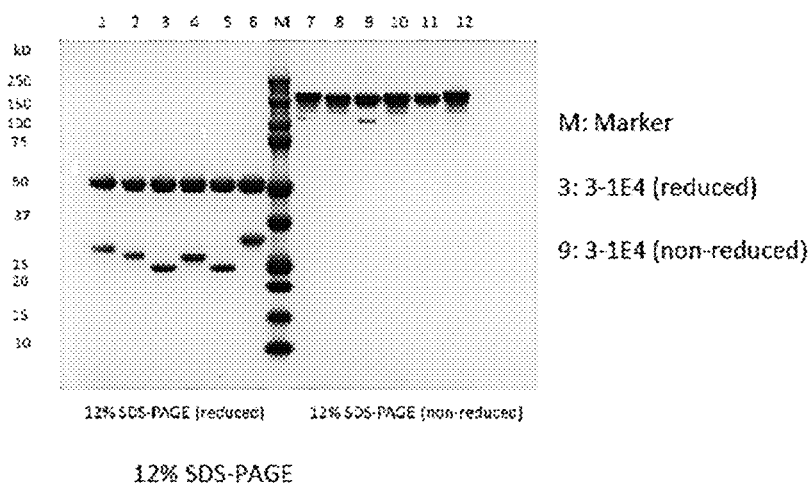
FIGS. 10A and 10B show full-length antibody 3-1E4 characterized by SDS-PAGE (FIG. 10A) and size exclusion chromatography (FIG. 10B).
Figure 10B:
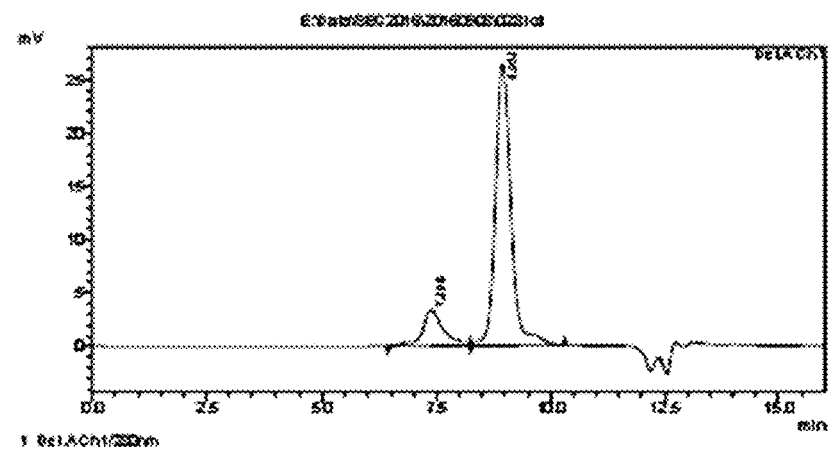

Phage Binding ELISAs:

ELISAs were performed using the same strategy as the panning. For clones from the indirect panning, plates were first coated with anti-human Fc antibody and then the Fc protein. For clones from the direct panning, plates were directly coated with the Fc protein. In indirect ELISA assays, phages were tested for their ability to bind hPDL1-Fc and an irrelevant Fc protein (or hIgG1) in parallel assays. Phages that showed low binding to the irrelevant Fc protein and high binding to the hPDL1 were selected for further sequencing and secondary screening. Data were shown in FIG. 3. Non-specific binding of most clones is low (signal value against Fc protein (1:10 dilution) is less than 0.2). In direct ELISA assays, phages were tested for their ability to bind hPDL1-Fc, mPDL1-Fc (mouse PDL1) and hIgG1 in parallel assays. Phages showed that there was no significant binding to mouse PDL1 by any of the lead molecules in the present invention, namely, none of the lead molecules show significant cross-reactivity with mouse PDLL. Data are shown in FIG. 7.

Sequencing:

Unique clones were identified by initially sequencing the CDR3 region of the heavy chain. This was later confirmed by the complete sequence as well. A small subset of clones shared the same CDR3 but had significant divergence in other parts of their sequences.

Secondary Screening by FACS:

Phages, phage lysates or lysates from bacteria expressing scFvs were tested for their ability to preferentially bind to 293T cells expressing hPDL1 but not parental 293T cells. The ratio of the mean fluorescence intensity (MFI) was used as the basis for identifying positive clones. Data were shown in FIG. 4. Most clones showed high ratio that could be identified as positive clones.

Blocker Identification:

Phages, phage lysates or lysates from bacteria expressing scFvs were tested for their ability to block the interaction between hPD1 and hPDLL The binding assays were set up by either coating the plates with hPD1-Fc or hPDL1-Fc. Binding of the biotinylated ligand (hPDL1 or hPD1) was detected using streptavidin-HRP using standard methods. The loss of binding in the presence of the scFv was used to identify potential blockers. Results are shown in FIGS. 5 and 6.

Generation and Characterization of Fc Fusion Proteins:

Since scFvs are relatively unstable, some scFvs were converted to Fc fusions and expressed in mammalian cells. These were purified using Protein A columns and tested for their ability to block PD1-PDL1 interaction as well as their ability to bind PDL1-expressing 293T cells.

Generation of Full-Length Antibodies:

Full-length antibody genes were constructed by PCR-amplifying the VH and VL regions from individual scFv clones and cloned into appropriate expression vectors using standard methods familiar to one skilled in the art. Full-length antibody proteins were generated by transiently transfecting suspension-grown 293T cells and purified using a Protein A column by standard methods familiar to one skilled in the art.

Figure 11A:
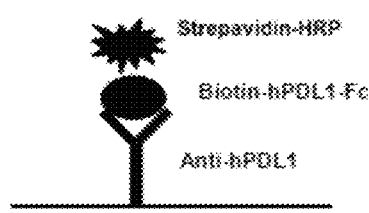
FIGS. 11B and 11C show results of quantitative binding analysis of some of the full-length antibody embodiments according to the present invention in to hPDL1 in an ELISA format according to FIG. 11A.
Figure 11B:
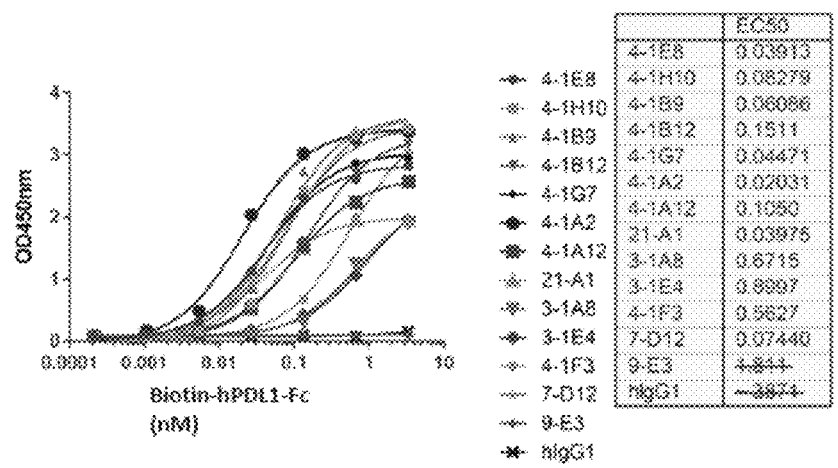
Figure 11C:
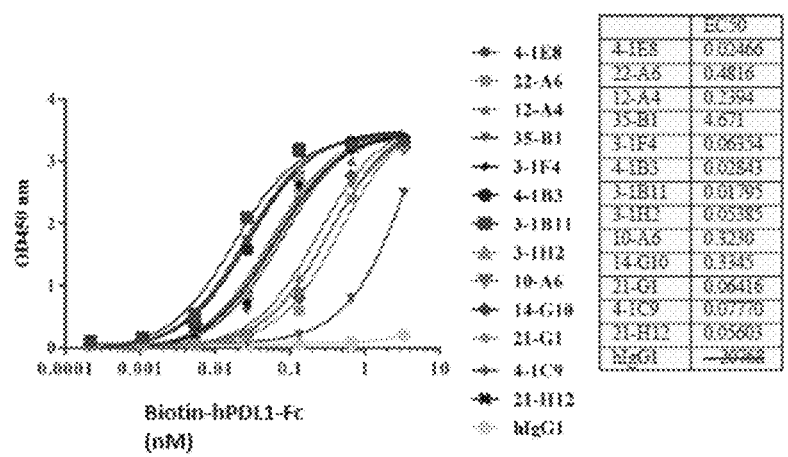
Figure 12A:
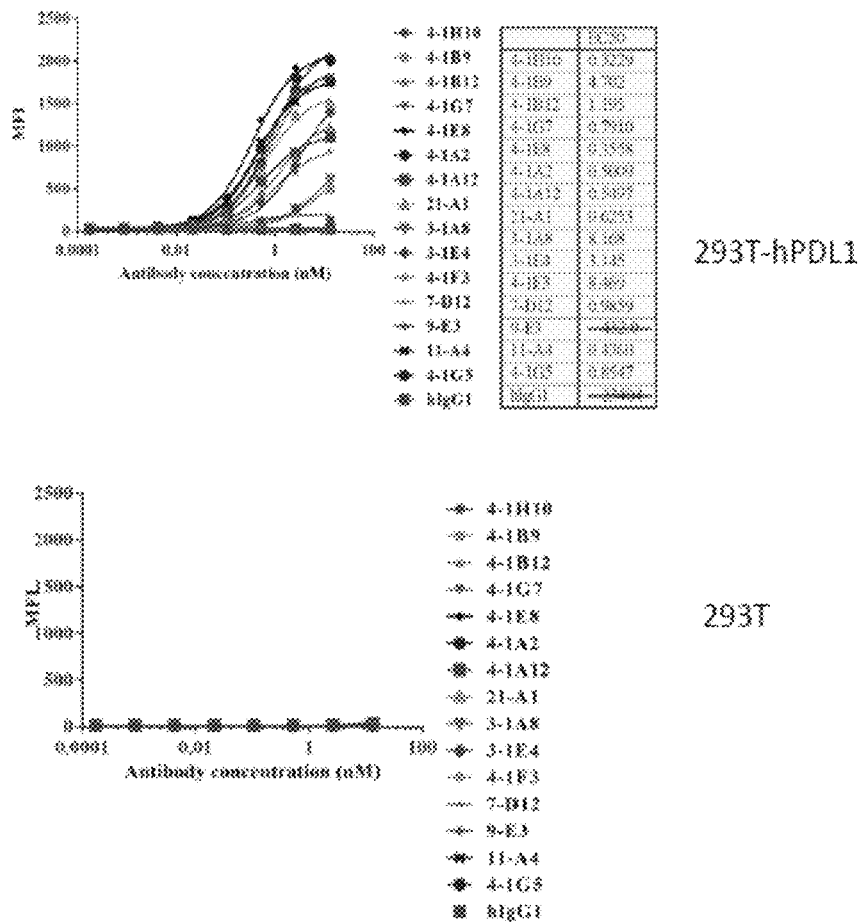
FIG. 12A and 12B show results of quantitative FACS for some of the full-length antibody embodiments according to the present invention where binding to hPDL1-expressing 293T cells (top graph), and hPDL1-negative 293T cells (bottom graph).
Figure 12B:
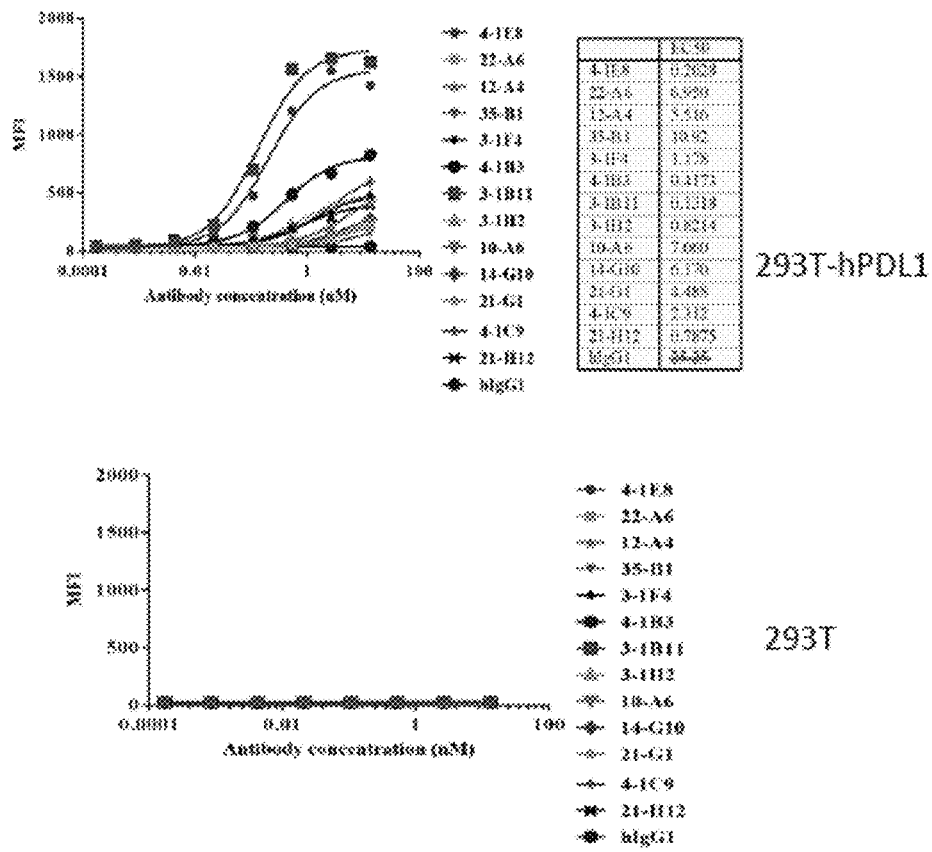
Figure 13A:
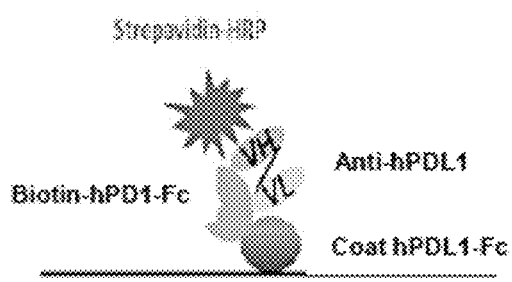
FIG. 13B shows results in receptor blocking assay of the lead antibody candidates in the present invention in RBA Format 1 (FIG. 13A): coated with hPDL1-Fc and added with Biotin-hPD1-Fc.
Figure 13B:
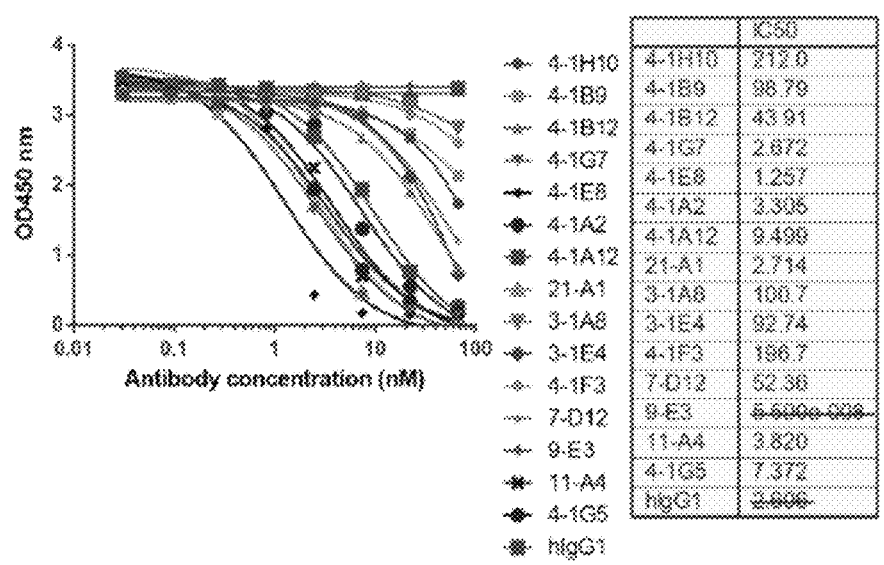
Figure 14A:
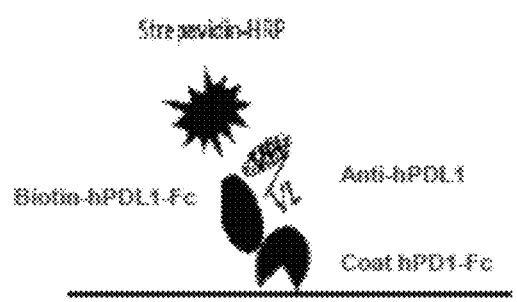
FIG. 14B shows results in receptor blocking assay of the lead antibody candidates in the present invention in RBA Format 2 (FIG. 14A): coated with hPD1-Fc and added with Biotin-hPDL1-Fc.
Figure 14B:
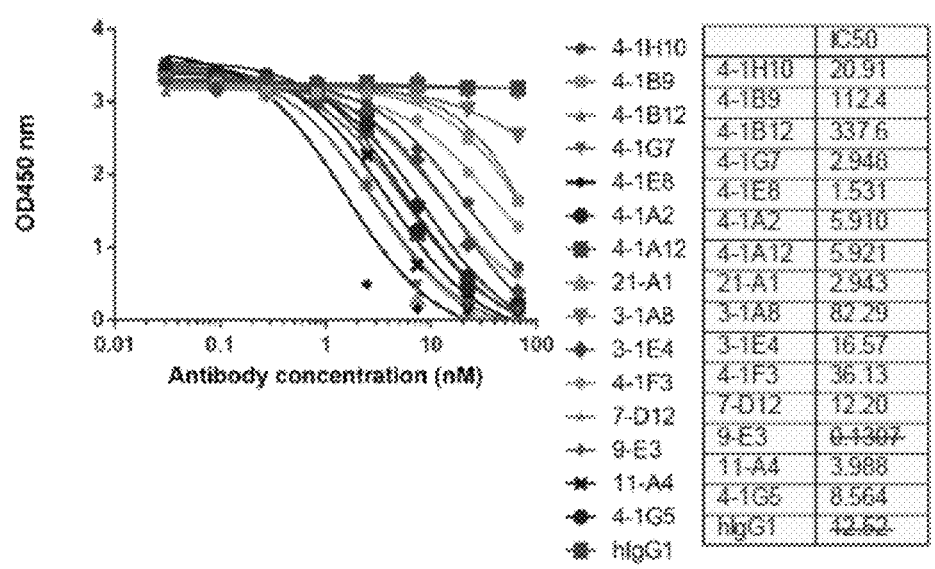

Characterization of Full-Length Antibodies:

Exemplary full length antibodies were characterized by SDS-PAGE and size exclusion chromatography (result was shown in FIGS. 8A, 8B, 9A, 9B, 10A, and 10B), as well as quantification of their potency in (a) specifically binding hPDL1 by ELISA (result was shown in FIGS. 11B and 11C); (b) specifically binding hPDL1-expressing 293T cells and unstrained 293T cells (results were shown in FIGS. 12A and 12B); and (c) blocking PD1-PDL1 interaction in both versions of the blocking assay. Resulting data for exemplary lead antibody candidates in Format 1 and Format 2 are shown in FIGS. 13B and 14B. Resulting data for 27 antibody embodiments in the present invention are shown in FIG. 15.

Figures 16A, 16B:
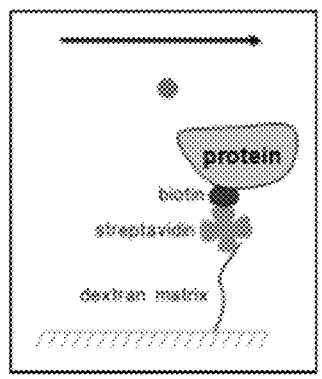
FIGS. 16A-16D depict affinities to PD-L1 of lead antibody candidates using BIAcore.
Figure 16C:
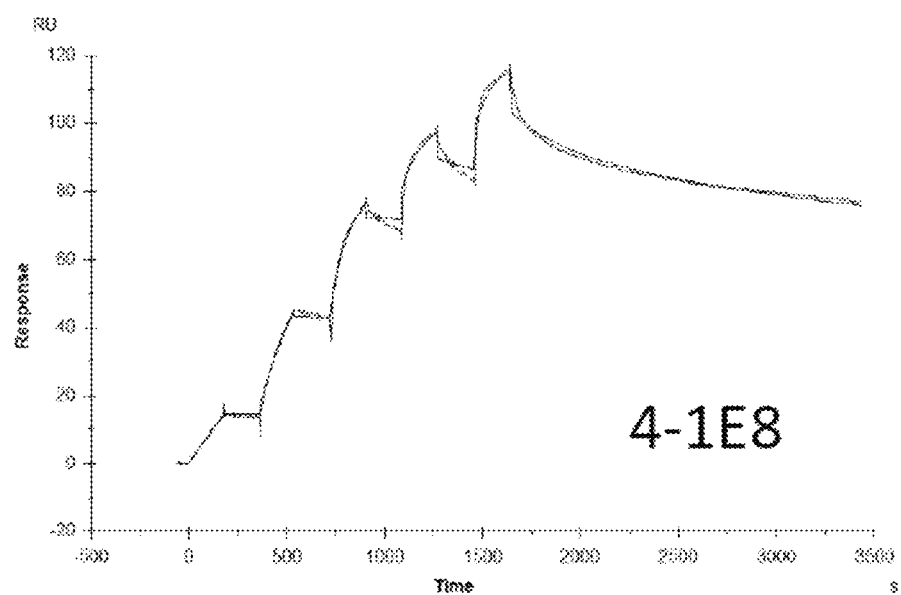
Figure 16D:
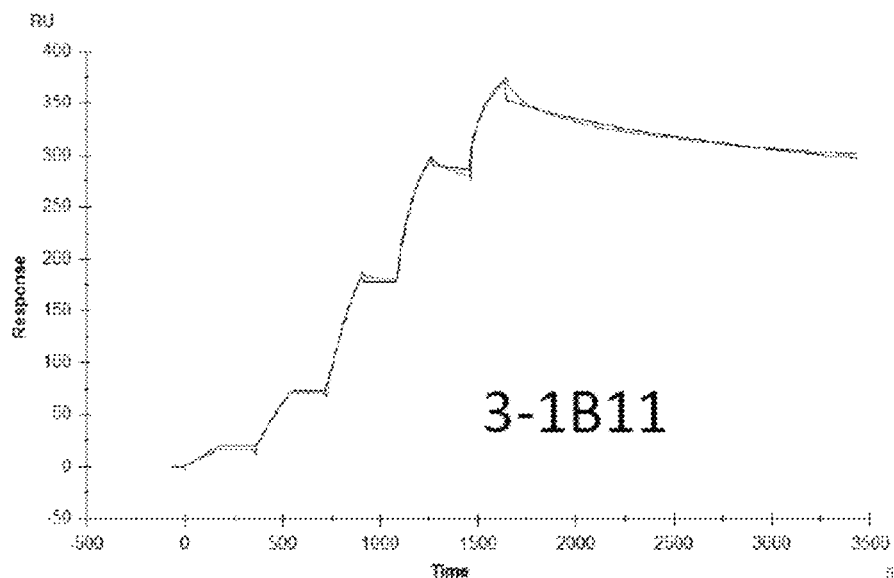
Figure 17A:
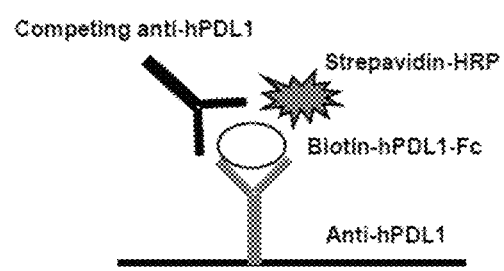
FIG. 17A schematically depicts an epitope-binning format utilized according to an example of the present invention.
Figure 17B:
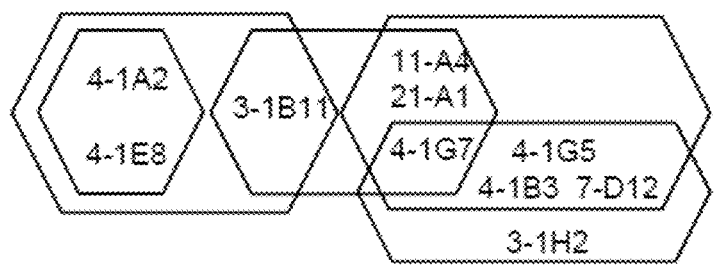
FIG. 17B schematically depicts an epitope bins for lead antibody candidates according to an embodiment of the present invention.
Figure 17C:
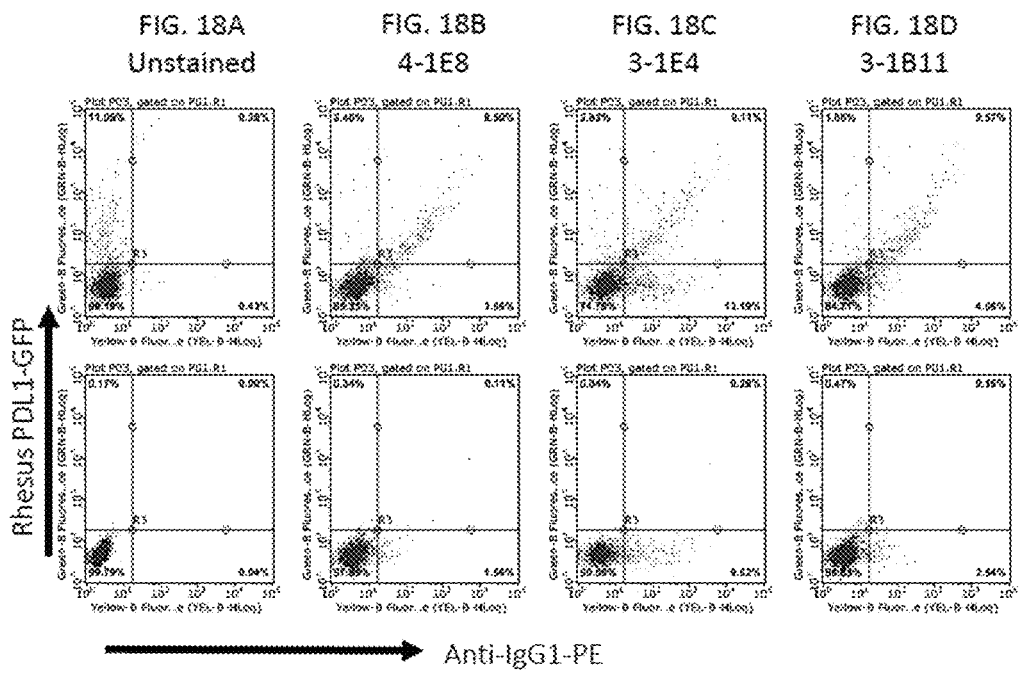
FIG. 17C lists epitope-binning matrix for lead antibody candidates using the format represented in FIG. 17A.

Affinity of PD-L1 Interaction by BIAcore:

The lead antibody candidates were tested for their affinities to PD-L1 using BIAcore (FIGS. 16B-16D). Briefly, biotinylated hPDL1 was captured through streptavidin onto the sensor chip surface. Antibody was made to flow over the chip and the reaction parameters were calculated using a single cycle kinetics method based on the stability of the interaction. KD values were evaluated using BIAcore X100 evaluation software 2.0 with bivalent analyte binding model.

Rhesus PD-L1 Binding by FACS (A) 293T cells were transiently transfected with Rhesus PDL1-GFP expression construct. Embodiments 4-1E8, 3-1E4 and 3-1B11 were tested and compared to control. Results are shown in FIGS. 18A-18D: all three antibodies bound rhesus PDL1

(B) 293T cells were transiently transfected with Rhesus PDL1 expression construct. Embodiments 4-1E8, 3-1E4 and 3-1B11 were tested and compared to control. Results are shown in FIGS. 19A-19D: all three antibody embodiments bound rhesus PDL1.

IL2 Induction and EC50 Determination

Peripheral Blood Mononuclear Cells (PBMCs) were isolated from human blood with a Ficoll gradient, followed by red blood cell lysis, using standard protocols. For the assay, RPMI+ medium was prepared as follows: 10% FBS, 1% anti-anti (Gibco) and 1% non-essential amino acids (Gibco) were added to RPMI medium with ATCC modification (Gibco). After isolation from blood, PBMCs were resuspended in 10-20 ml RPMI and were cultured overnight at 37° C. with 5% $CO_2$. Next, PBMCs were seeded into 96 well tissue culture plates (Corning) at a concentration of 100 000 PBMCs/96 well; the final volume per well was 200 ul. Staphylococcal Enterotoxin B (SEB) was added at a concentration of 1 ng/ml, and lead antibodies were added at 20 ug/ml (for screening) or at a range of concentrations from 50 ug/ml to 0.003 ug/ml. As controls, cells without SEB (e.g. no stimulation); with SEB alone or with SEB and isotype control (e.g., baseline).

Figure 20:
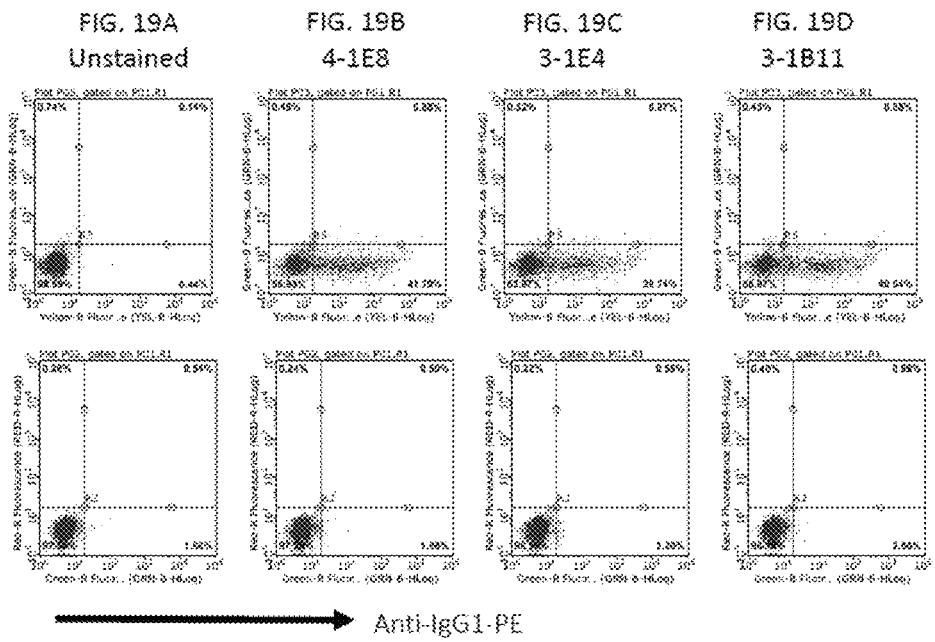
FIG. 20 shows representative EC50 results of IL-2 production experiment according to embodiments of the invention.
Figure 23A:
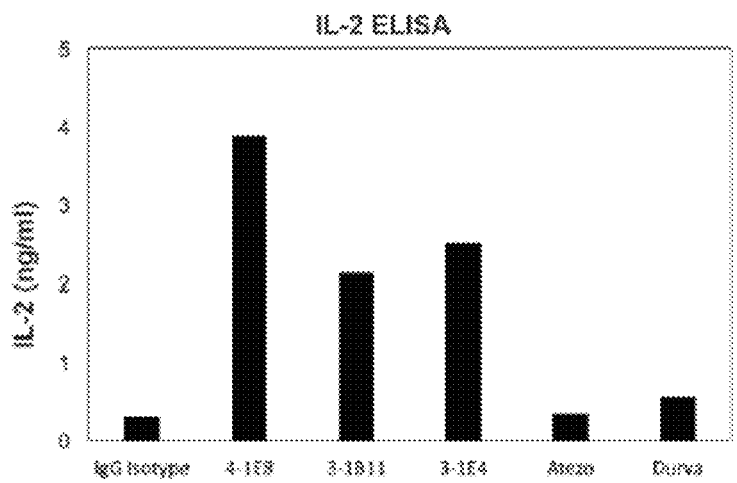
FIGS. 23A, 23B and 23C provide three sets of experimental data of IL-2 production ability of PBMCs co-cultured with PDL1+ MDA-MB-231 tumor cells in the presence of lead antibodies according to the invention in comparison to commercially available anti-PDL1 antibodies.
Figure 23B:
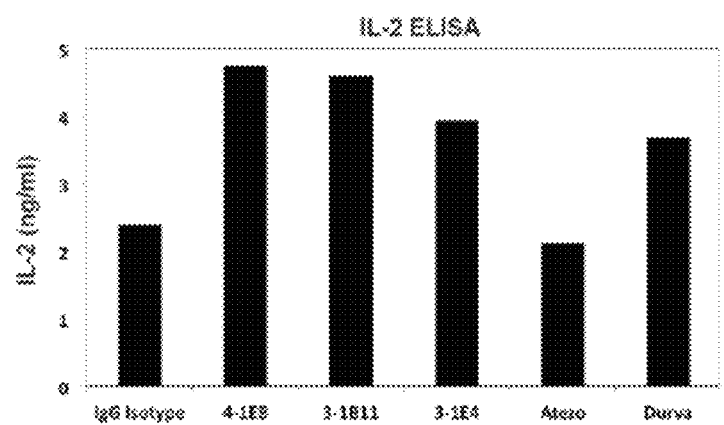
Figure 23C:
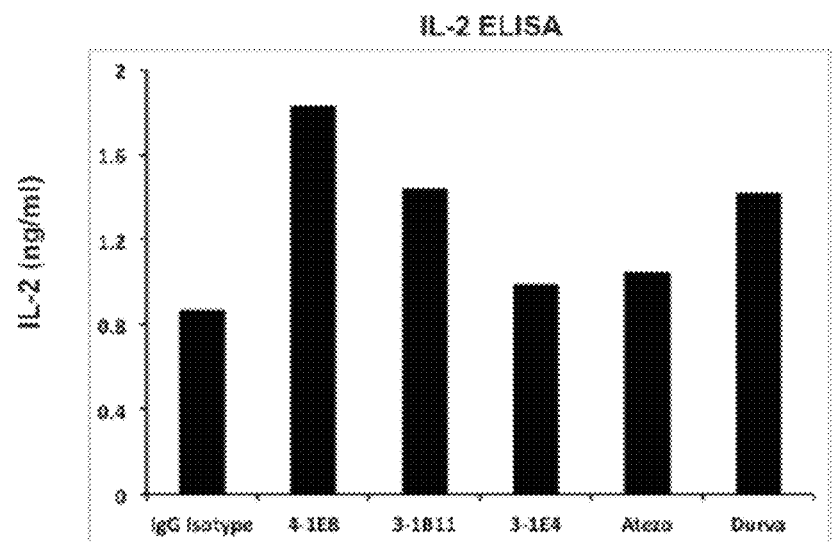
Figure 24:
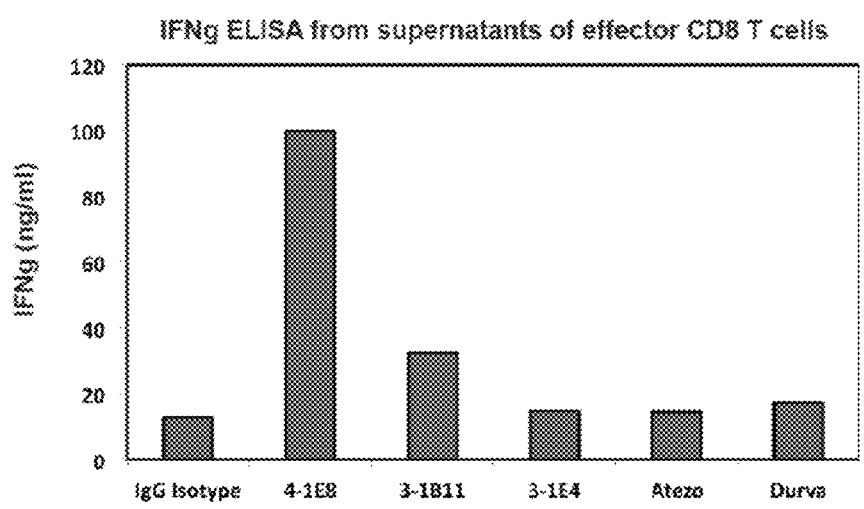
FIG. 24 provides results of IFNγ production ability of CD8 T cells co-cultured with PDL1+ MDA-MB-231 tumor cells in the presence of lead antibodies according to the invention in comparison to commercially available anti-PDL1 antibodies.

After a 76-hour incubation at 37° C. with 5% $CO_2$, PBMCs were spun down at 1200 rpm for 15 minutes at room temperature, and supernatants were collected and stored at −20° C. IL2 ELISA was performed using a commercially available IL2-ELISA kit (Biolegend or Thermofisher), following instructions from the manufacturer. Supernatants were diluted 1/20-1/80 for the ELISA. The absorbance was measured using a Spectramax3 M3 microplate reader (Molecular Devices), and data were analyzed using Graphpad software. The lead antibody candidates were compared to commercially available anti-PD1 antibodies. Results are shown in FIG. 20. In the tumor co-culture experiments with MDA-MB-231 cells (see FIGS. 23A-23C), the 4-1E8 was consistently better than 3-1B11 and 3-1E4 in de-repressing IL2 (see FIGS. 23A-23C) and IFNγ (see FIG. 24). However, all three antibodies were as good or better than commercial PDL1 antibodies such as atezolizumab (Atezo) and durvalumab (Durva) production in similar co-culture experiments with T cells and MDA-MB-231 cells.

ADCC Activity

As shown in FIGS. 21 and 22, all three lead antibodies showed robust ADCC activity while atezolizumab (which is engineered to be ADCC-negative) showed no activity. Among the three embodiments of the invention, 4-1E8 showed the most amount of ADCC activity.

Mixed Lymphocyte Reaction

Peripheral Blood Mononuclear Cells (PBMCs) were isolated from human blood with a Ficoll gradient, followed by red blood cell lysis, using standard protocols. Cells were cultured in serum-free RPMI 1640 for 1 hour at 37° C. Non-adherent cells were removed, and remaining monocytes were cultured in RPMI 1640 supplemented with 5% human AB serum, 2 ng/mL GM-CSF, and 10 ng/mL IL4 (BD Biosciences). Fresh media with cytokine supplements were added every 2 to 3 days. Mature dendritic cells were induced by addition of 20 ng/mL TNFa (BD Biosciences) on day 6 and cultured for 24 hours.

Figure 25A:
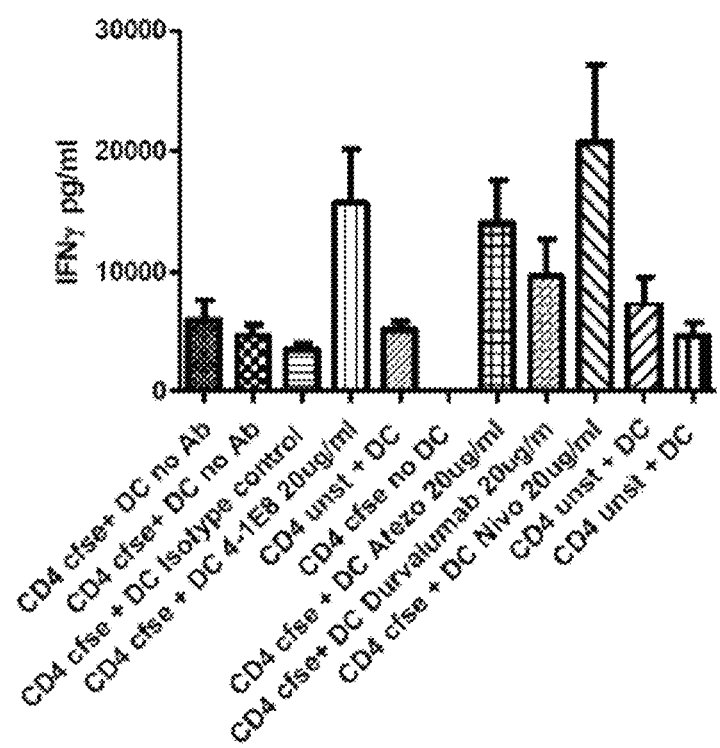
FIGS. 25A and 25B show mixed lymphocyte reaction results of lead antibodies according to embodiments of the invention.
Figure 25B:
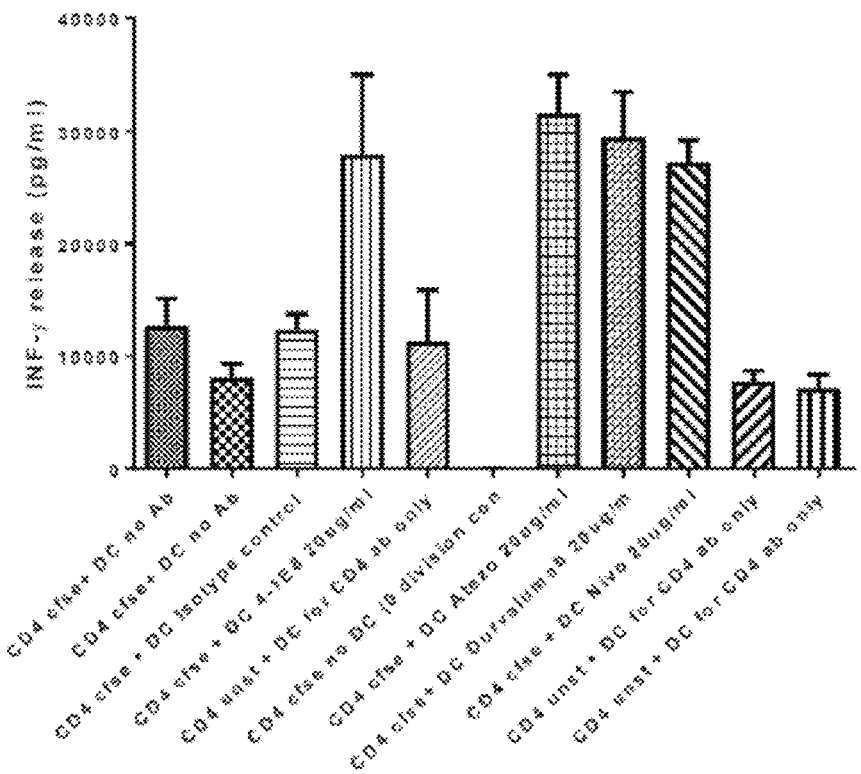

Dendritic cells were harvested, phenotyped, and frozen for later use. CD4 T cells were isolated from PBMCs using magnetic beads (Dynal) as per manufacturer's instructions. CD4 T cells were cultured in 96 well-flat bottom plates (Costar) together with allogeneic dendritic cells at a ratio of 1:2.5, using RPMI 1640 supplemented with 10% human AB serum. Dendritic cells were treated with 100 mg/mL of mitomycin C (Sigma) before addition. Proliferation was measured by CFSE (or similar dye) dilution in T cells. IFNg release was measured using a commercially available IFNg-ELISA kit, following instructions of the manufacturer. The absorbance was measured using a Spectramax3 M3 microplate reader (Molecular Devices), and data were analyzed using graphpad software. In these studies, the lead antibody candidates according to embodiments of the present invention performed comparably to other commercially available anti-PD1 and anti-PDL1 antibodies. Exemplary results are shown in FIGS. 25A and 25B.

Binding Specificity

Figure 26A:
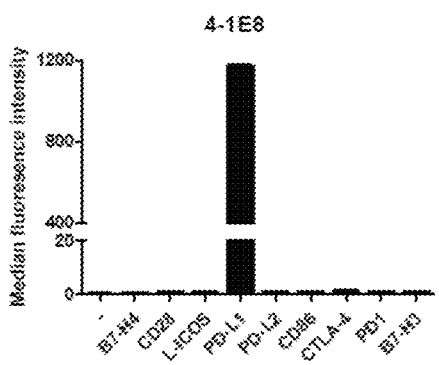
FIGS. 26A and 26B show the specificity of binding by antibodies of the invention coded "4-1E8" (FIG. 26A) and "3-1B11" (FIG. 26B).
Figure 26B:
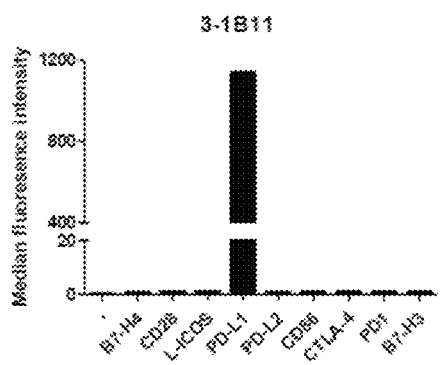

Lines of Expi293 cells were generated that stably expressed a variety of B7 family members and their receptors. The ability of anti-PDL1 antibodies was tested by FACS using fluorescent anti-human IgG. Resulting data for exemplary lead antibody candidates are shown in FIGS. 26A and 26B.

Blocking CD80-PDL1 Binding

Figures 27A, 27B:
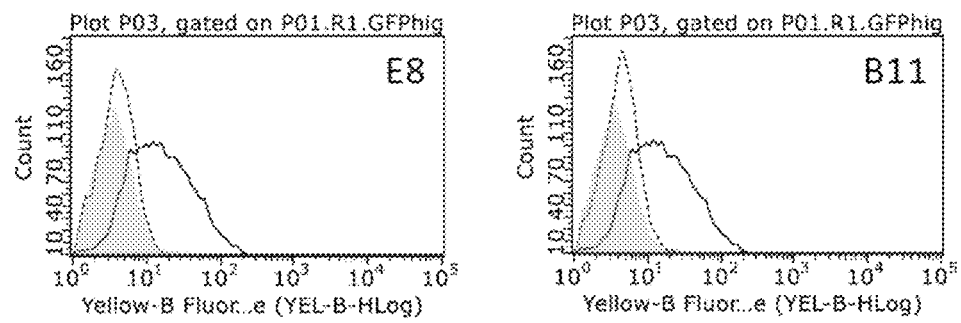
FIGS. 27A and 27B show ability of the antibodies of the invention E8 (FIG. 27A) and B11 (FIG. 27B) to block CD80 from binding PD-L1-expressing cells (grey silled curves) compared to CD80 alone (solid line) and secondary alone (dashed line).

DLD1 cells engineered to express PDL1 bind were used to detect binding of biotinylated CD80-Fc in the presence or absence of anti-PDL1 Abs, followed by fluorescent streptavidin. Resulting data for exemplary lead antibody candidates of the present invention are shown in FIGS. 27A and 27B.

Half-Life Measurement

Figure 28:
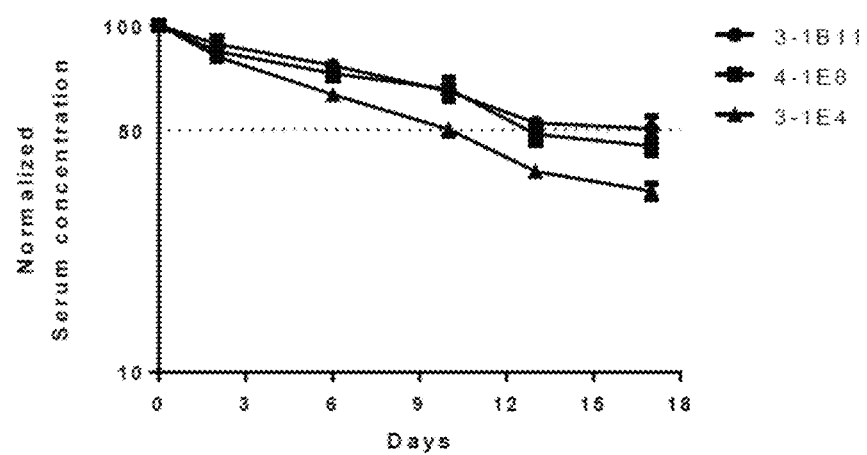
FIG. 28 shows half-life measurement of the antibody embodiments of the invention using Tg32 mice.

Serum half-life was measured using male homozygous Tg32 mice (B6.Cg-Fcgrttm1Dcr Tg(FCGRT)32Dcr/DcrJ, Jackson labs). 2 mg/kg of antibody was injected IV on Day 0 and blood was drawn on Day 1 and various later time points. Plasma was prepared and antibody titers were measured using a sandwich ELISA. Titers were normalized to Day 1 titers. Anti-antibody response was also measured and samples with high titers were removed from the analysis because they often showed sudden changes in the ELISA. Resulting data for exemplary lead antibody candidates of the present invention are shown in FIG. 28. Half-life for different antibodies ranged from 6.9 days (3-1E4, see Example 9 below for sequence details) to 10.5 days (3-1B11, see Example 11 below for sequence details) and 12.3 days (4-1E8, see Example 5 below for sequence details).

Polypeptide Sequences

Examples of PD-L1 binding polypeptide sequences according to the present inventions are listed as follows:

Example 1

Antibody Code: 4-1A2

VH
DNA
(SEQ ID NO: 1)
```
CAGGTTCAGCTGGTGCAGTCTGGGACTGAGGTGAAGAAGCCTGGGGCCT

CAGTGAAGGTCTCCTGCAAGGCTTCTGGATACACCTTCACCAGTTATGA

TATCAACTGGGTGCGACAGGCCACTGGACAAGGGCTTGAGTGGATGGGA

TGGATCAACCCTAACAGTGGTGGCACAAACTATGCACAGAAGTTTCAGG

GCAGGGTCACCATGACCACAGACACTTCTACGGGCACAGCCTACATGGA

GCTGAGGAGCCTGAGATCTGACGACACGGCCGTGTATTACTGTGCGAGA

TTTTTATGGGGTTCGGGGAGTTATGACTACTGGGGCCAGGGAACCCTGG

TCACCGTCTCCTCA
```

AMINO ACID
(SEQ ID NO: 2)
```
QVQLVQSGTEVKKPGASVKVSCKASGYTFTSYDINWVRQATGQGLEWMG

WINPNSGGTNYAQKFQGRVTMTTDTSTGTAYMELRSLRSDDTAVYYCAR

FLWGSGSYDYWGQGTLVTVSS
```

VL
DNA
(SEQ ID NO: 3)
```
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTCGCAACTTACTACTGTCAACAGACTTACACATTCCCGCACACTTTT

GCCCAGGGGACCAACCTGGAGATCAAA
```

AMINO ACID
(SEQ ID NO: 4)
```
DIQMTQSPSSLSASVGDRVTITCRASQSISSYLNWYQQKPGKAPKLLIY

AASSLQSGVPSRFSGSGSGTDFTLTISSLQPEDFATYYCQQTYTFPHTF

AQGTNLEIK
```

Example 2

Antibody Code: 4-1A12

VH
DNA
(SEQ ID NO: 5)
```
CAAGTCCAGCTGGTACAATCTGGAGCTGAGGTGAAGAAGCCTGGGGCCT

CAGTGAAGGTCTCCTGCAAGGCTTCTGGTTACACCTTTACCAGCTATGG

TATCAGCTGGGTGCGACAGGCCCCTGGACAAGGGCTTGAGTGGATGGGA

TGGATCAGCGCTTACAATGGTAACACAAACTATGCACAGAAGCTCCAGG

GCAGAGTCACCATGACCACAGACACATCCACGAGCACAGCCTACATGGA

GCTGAGGAGCCTGAGATCTGACGACACGGCCGTGTATTACTGTGCGAGA

GATTGGATACAGCTATGGTTACCCCTTGACTACTGGGGCCAGGGAACCC

TGGTCACCGTCTCCTCA
```

AMINO ACID
(SEQ ID NO: 6)
```
QVQLVQSGAEVKKPGASVKVSCKASGYTFTSYGISWVRQAPGQGLEWMG

WISAYNGNTNYAQKLQGRVTMTTDTSTSTAYMELRSLRSDDTAVYYCAR

DWIQLWLPLDYWGQGTLVTVSS
```

VL
DNA
(SEQ ID NO: 7)
```
GACATCCAGTTGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAACAGAAACCAGGGAAAGCCCCTAAGCTCCTGATCTAT

GGTGCATCCAGTTTGGAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAACAGAGTCACAGTTCCCCCCTCACTTTC

GGCGGAGGGACCAAGGTGGACATCAAA
```

AMINO ACID
(SEQ ID NO: 8)
```
DIQLTQSPSSLSASVGDRVTITCRASQSISSYLNWYQQKPGKAPKLLIY

GASSLESGVPSRFSGSGSGTDFTLTISSLQPEDFATYYCQQSHSSPLTF

GGGTKVDIK
```

Example 3

Antibody Code: 4-1B9

VH
DNA
(SEQ ID NO: 9)
GAAGTGCAGCTGGTGCAGTCTGGGGGAGGCTTGGTCCAGCCTGGGAGGT
CCCTGAGACTCTCCTGTGCAGCCTCTGGATTCACCTTCAGTAGCTATGG
CATGCACTGGGTCCGCCAGGCTCCAGGCAAGGGGCTGGAGTGGGTGGCA
GTTATATCATATGATGGAAGTAATAAATACTATGCAGACTCCGTGAAGG
GCCGATTCACCATCTCCAGAGACAATTCCAAGAACACGCTGTATCTGCA
AATGAACAGCCTGAGAGCTGAGGACACGGCTGTGTATTACTGTGCGAAA
GATTTGATCCCGTTGCGAGATAGTAGGGGGGGGTACTACTACGGTATGG
ACGTCTGGGGCCAAGGGACCACGGTCACCGTCTCCTCAGGGAGT

AMINO ACID
(SEQ ID NO: 10)
EVQLVQSGGGLVQPGRSLRLSCAASGFTFSSYGMHWVRQAPGKGLEWVA
VISYDGSNKYYADSVKGRFTISRDNSKNTLYLQMNSLRAEDTAVYYCAK
DLIPLRDSRGGYYYGMDVWGQGTTVTVSS

VL
DNA
(SEQ ID NO: 11)
TCTTCTGAGCTGACTCAGGACCCTGCTGTGTCTGTGGCCTTGGGACAGA
CAGTCAGGATCACATGCCAAGGAGACAGCCTCAGAGACTATTATGCAAG
CTGGTACCAGCAGAAGCCAGGACAGGCCCCTGTACTTGTCATCTATGGT
AAAAACAACCGGCCCTCAGGAATCCCAGACCGATTCTCTGGCTCCAGCT
CAGGAAACACAGCTTCCTTGACCATCACTGGGACTCAGGCGGAAGATGA
GGCTGACTATTACTGTAACTCCCGTGACAGCGGTGCTTACCATTATGTC
TTCGGAACTGGGACCAAGGTCACCGTCCTA

AMINO ACID
(SEQ ID NO: 12)
SSELTQDPAVSVALGQTVRITCQGDSLRDYYASWYQQKPGQAPVLVIYG
KNNRPSGIPDRFSGSSSGNTASLTITGTQAEDEADYYCNSRDSGAYHYV
FGTGTKVTVL

Example 4

Antibody Code: 4-1B12

VH
DNA
(SEQ ID NO: 13)
CAAATCCAGCTGGTGCAGTCTGGGGGAGGCGTGGTCCAGCCTGGGAGGT
CCCTGAGACTCTCCTGTGCAGCCTCTGGATTCACCTTCAGTAGCTATGG
CATGCACTGGGTCCGCCAGGCTCCAGGCAAGGGGCTGGAGTGGGTGGCA
GTTATATCATATGATGGAAGTAATAAATACTATGCAGACTCCGTGAAGG
GCCGATTCACCATCTCCAGAGACAATTCCAAGAACACGCTGTATCTGCA
AATGAACAGCCTGAGAGCTGAGGACACGGCTGTGTATTACTGTGCGAAA
GGAAGTATTATAGGGGATGGTGCTTTTGATATCTGGGGCCAAGGGACAA
TGGTCACCGTCTCTTCA

AMINO ACID
(SEQ ID NO: 14)
QIQLVQSGGGVVQPGRSLRLSCAASGFTFSSYGMHWVRQAPGKGLEWVA
VISYDGSNKYYADSVKGRFTISRDNSKNTLYLQMNSLRAEDTAVYYCAK
GSIIGDGAFDIWGQGTMVTVSS

VL
DNA
(SEQ ID NO: 15)
GATATTGTGATGACCCAGTCTCCACTCTCCCTGCCCGTCACCCTTGGAG
AGCCGGCCTCCATCTCCTGCAGGTCTAGTCAGACCCTCCTGCATAATGG
ATTCAACTTTTTGGATTGGTACCTGCAGAAGCCAGGGCAGTCTCCACAA
CTCCTGATGTATTTGGCCTCTAGCCGGGCCTCCGGGGTCCCTGACAGGT
TCAGTGGCAGTGGATCGGGCACAGATTTCACACTGAAAATCAGCAGAGT
GGAGGCTGAGGATGTTGGGGTTTATTACTGCATGCAAGGTACACACTGG
CCGTACACTTTTGGCCAGGGGACCAAGCTGGATATCAAA

AMINO ACID
(SEQ ID NO: 16)
DIVMTQSPLSLPVTLGEPASISCRSSQTLLHNGFNFLDWYLQKPGQSPQ
LLMYLASSRASGVPDRFSGSGSGTDFTLKISRVEAEDVGVYYCMQGTHW
PYTFGQGTKLDIK

Example 5

Antibody Code: 4-1E8

VH
DNA
(SEQ ID NO: 17)
CAAATCCAGCTGGTACAATCTGGGGCTGAGGTGAAGATGCCTGGGGCCT
CAGTGACGATTTCCTGCGAGGCGTCTGGATACAACTTCATCAGCTACTA
TATACACTGGGTGCGACAGGCCCCTGGACAAGGCCTTGAGTGGATGGGA
TTCGTCGTCCCTAGTGGTGGTGCCGCAGGCTACACACAGAAGTTCCAGG
GCAGACTCACCGTGACCAGGGACACGTCCACGAGCACAGTCTACATGGA
CCTGAACAGCCTGACATCTGACGACACGGCCGTGTATTACTGTGTGCGA
GAAATGAGTGGTGGCTGGTTTGATTTCTGGGGCCAGGGAACCCTGGTCA
CCGTCTCCTCG

AMINO ACID
(SEQ ID NO: 18)
QIQLVQSGAEVKMPGASVTISCEASGYNFISYYIHWVRQAPGQGLEWMG
FVVPSGGAAGYTQKFQGRLTVTRDTSTSTVYMDLNSLTSDDTAVYYCVR
EMSGGWFDFWGQGTLVTVSS

VL
DNA
(SEQ ID NO: 19)
GACATCGTGATGACCCAGTCTCCATCCTCCCTGTCTGCATCTGTAGGAG
ACAGAGTCACCATCACTTGCCGGGCAAGTCAGGGCATTAGAAATGATTT
AGGCTGGTATCAGCAAAAACCAGGGAAAGCCCCTAAGCTCCTGATCTAT

GCTGCATCCACTTTGCAAAGTGGGGTCCCATCAAGGTTCAGCGGCAGTG

GATCTGGGACAGATTTCACTCTCACCATCAGCAGCCTGCAGGCTGAAGA

TGTGGCAGTTTATTACTGTCAGCAATATTATAGTACTCCTCTCACTTTC

GGCCCTGGGACCAAAGTGGATATCAAA

AMINO ACID (SEQ ID NO: 20)

DIVMTQSPSSLSASVGDRVTITCRASQGIRNDLGWYQQKPGKAPKLLIY

AASTLQSGVPSRFSGSGSGTDFTLTISSLQAEDVAVYYCQQYYSTPLTF

GPGTKVDIK

Example 6

Antibody Code: 4-1G7

VH
DNA (SEQ ID NO: 21)

GAGGTGCAGCTGGTGCAGTCTGGGGCTGAGGTGAAGAAGCCTGGGTCCT

CGGTGAAGGTCTCCTGCAAGGCTTCTGGTTACACCTTTACCAGCTATGG

TATCAGCTGGGTGCGACAGGCCCCTGGACAAGGGCTTGAGTGGATGGGA

TGGATCAGCGCTTACAATGGTAACACAAACTATGCACAGAAGCTCCAGG

GCAGAGTCACCATGACCACAGACACATCCACGAGCACAGCCTACATGGA

GCTGAGGAGCCTGAGATCTGACGACACGGCCGTGTATTACTGTGCGAGA

GCCTCACCGGTACAGCAGCCCATATGGTGGGCGGAGTACTGGGGCCAGG

GAACCCTGGTCACCGTCTCCTCA

AMINO ACID (SEQ ID NO: 22)

EVQLVQSGAEVKKPGSSVKVSCKASGYTFTSYGISWVRQAPGQGLEWMG

WISAYNGNTNYAQKLQGRVTMTTDTSTSTAYMELRSLRSDDTAVYYCAR

ASPVQQPIWWAEYWGQGTLVTVSS

VL
DNA (SEQ ID NO: 23)

CAGTCTGCCCTGACTCAGCCTGCCTCCGTGTCTGGGTCTCCTGGACAGT

CGATCACCATCTCCTGCACTGGAACCAGCAGTGACGTTGGTGGTTATAA

CTATGTCTCCTGGTACCAACAGCACCCAGGCAAAGCCCCCAAACTCATG

ATTTCTGATGTCAGTAAGCGGCCCTCAGGGGTTTCTAATCGCTTCTCTG

GCTCCAAGTCTGGCAACACGGCCTCCCTGACCATCTCTGGGCTCCAGGC

TGAGGACGAGGCTGATTATTACTGCAGCTCATATACAAGCAACTACACT

TTGGTATTCGGCGGAGGGACCAAGCTGACCGTCCTA

AMINO ACID (SEQ ID NO: 24)

QSALTQPASVSGSPGQSITISCTGTSSDVGGYNYVSWYQQHPGKAPKLM

ISDVSKRPSGVSNRFSGSKSGNTASLTISGLQAEDEADYYCSSYTSNYT

LVFGGGTKLTVL

Example 7

Antibody Code: 4-1H10

VH
DNA (SEQ ID NO: 25)

CAGCTGCAGCTACAGCAGTCCGGAGCTGAGGTGAAGAAGCCTGGGTCCT

CGGTGAAGGTCTCCTGCAAGGCTCCTGGAGGCACCTTCAGCAGCTATGC

TATCAGCTGGGTGCGACAGGCCCCTGGACAAGGGCTTGAGTGGATGGGA

AGGATCATCCCTATCCTTGGTATAGCAAACTACGCACAGAAGTTCCAGG

GCAGAGTCACGATTACCGCGGACAAATCCACGAGCACAGCCTACATGGA

GCTGAGCAGCCTGAGATCTGAAGACACGGCCGTGTATTACTGTGCGAGT

CATGGTCGGGCAGCAGCTGGTAGGTACGCTATGGACGTCTGGGGCCAAG

GGACCACGGTCACCGTCTCCTCA

AMINO ACID (SEQ ID NO: 26)

QLQLQQSGAEVKKPGSSVKVSCKAPGGTFSSYAISWVRQAPGQGLEWMG

RIIPILGIANYAQKFQGRVTITADKSTSTAYMELSSLRSEDTAVYYCAS

HGRAAAGRYAMDVWGQGTTVTVSS

VL
DNA (SEQ ID NO: 27)

AATTTTATGCTGACTCAGCCCCACTCTGTGTCGGATTCTCCGGGGAAGA

CGGTAACCATCTCCTGCACCCGCAGCAGTGGCAGCATTGCCAGCAACTA

TGTGCAGTGGTACCAGCAGCGCCCGGGCAGTGCCCCCACCACTGTGATC

TATGACGATAAGCAAAGACCCTCTGGGGTCCCTGATCGGTTCTCGGGCT

CCATCGACAGCTCCTCCAACTCTGCCTCCCTCACCATCTCTGGACTGAC

GACTGAGGACGAGGCTGACTACTACTGTCAGTCCTTTGATGGCAGCAGT

GTCATCTTCGGCGGAGGGACCAAGCTGACCGTCCTG

AMINO ACID (SEQ ID NO: 28)

NFMLTQPHSVSDSPGKTVTISCTRSSGSIASNYVQWYQQRPGSAPTTVI

YDDKQRPSGVPDRFSGSIDSSSNSASLTISGLTTEDEADYYCQSFDGSS

VIFGGGTKLTVL

Example 8

Antibody Code: 3-1H2

VH
DNA (SEQ ID NO: 29)

CAGGTTCAGCTGGTGCAGTCTGGGGCTGAGGTGAAGAAGCCTGGGTCCT

CGGTGAAGGTCTCCTGCAAGGCTTCTGGAGGCACCTTCAGCAGCTATGC

TATCAGCTGGGTGCGACAGGCCCCTGGACAAGGGCTTGAGTGGATGGGA

GGGATCATCCCTATCTTTGGTACAGCAAACTACGCACAGAAGTTCCAGG

GCAGAGTCACGATTACCGCGGACGAATCCACGAGCACAGCCTACATGGA

GCTGAGCAGCCTGAGATCTGAGGACACGGCCGTGTATTACTGTGCGAGA

AAGGAGCGTTTCTATGATAGTAGTGGTTATTACGATGCTTTTGATATCT

GGGGCCAAGGGACAATGGTCACCGTCTCTTCA

AMINO ACID (SEQ ID NO: 30)

QVQLVQSGAEVKKPGSSVKVSCKASGGTFSSYAISWVRQAPGQGLEWMG

GIIPIFGTANYAQKFQGRVTITADESTSTAYMELSSLRSEDTAVYYCAR

KERFYDSSGYYDAFDIWGQGTMVTVSS

VL
DNA (SEQ ID NO: 31)

CAGTCTGCCCTGACTCAGCCTCGCTCAGTGTCCGGGTCTCCTGGGCAGT

CAGTCACCATCTCCTGCACTGGAACCAGCAATGATGTTGGTGGTTATAA

CTATGTCTCCTGGTACCAACAGCACCCAGGCAAAGCCCCCAAACTCATG

ATTTATGATGTCACTAAGCGGCCCTCAGGGGTCCCTGATCGCTTCTCTG

GCTCCAAGTCTGGCAACACGGCCTCCCTGACCGTCTCTGGCCTCCAGCC

TGAGGATGAGGCTGACTATTATTGCGCCTCTTATGGAGGCAGGAACAAT

TTGCTTTTTGGCGGAGGGACTCAACTGACCGTCTTA

AMINO ACID (SEQ ID NO: 32)

QSALTQPRSVSGSPGQSVTISCTGTSNDVGGYNYVSWYQQHPGKAPKLM

IYDVTKRPSGVPDRFSGSKSGNTASLTVSGLQPEDEADYYCASYGGRNN

LLFGGGTQLTVL

Example 9

Antibody Code: 3-1E4

VH
DNA (SEQ ID NO: 33)

CAAATCCAGCTGGTACAATCTGGGGCTGAGGTGAAGAAGCCTGGGTCCT

CGGTGAAGGTCTCCTGCAAGGCTTCTGGAGGCACCTTCAGCAGCTATGC

TATCAGCTGGGTGCGACAGGCCCCTGGACAAGGGCTTGAGTGGATGGGA

GGGATCATCCCTATCTTTGGTACAGCAAACTACGCACAGAAGTTCCAGG

GCAGAGTCACGATTACCGCGGACAAATCCACGAGCACAGCCTACATGGA

GCTGAGCAGCCTGAGATCTGAGGACACGGCCGTGTATTACTGTGCCGGA

GGGGGAGCAGTGGCGGACAATAGTTACTGGGGCCAGGGAACCCTGGTCA

CCGTCTCCTCA

AMINO ACID (SEQ ID NO: 34)

QIQLVQSGAEVKKPGSSVKVSCKASGGTFSSYAISWVRQAPGQGLEWMG

GIIPIFGTANYAQKFQGRVTITADKSTSTAYMELSSLRSEDTAVYYCAG

GGAVADNSYWGQGTLVTVSS

VL
DNA (SEQ ID NO: 35)

GACATCCGGATGACCCAGTCTCCATCCTCCCTGTCTGCATCTGTAGGAG

ACAGAGTCACCATCACTTGCCGGGCAAGTCAGGGCATTAGAAATGATTT

AGGCTGGTATCAGCAGAAACCAGGGAAAGCCCCTAAGCTCCTGATCTAT

GCTGCATCCAGTTTACAAAGTGGGGTCCCATCAAGGTTCAGCGGCAGTG

GATCTGGCACAGATTTCACTCTCACCATCAGCAGCCTGCAGCCTGAAGA

TTTTGCAACTTATTACTGTCTACAAGATTACAATTACCCTCGAACGTTC

GGCCAAGGGACCAAGGTGGAAATCAAA

AMINO ACID (SEQ ID NO: 36)

DIRMTQSPSSLSASVGDRVTITCRASQGIRNDLGWYQQKPGKAPKLLIY

AASSLQSGVPSRFSGSGSGTDFTLTISSLQPEDFATYYCLQDYNYPRTF

GQGTKVEIK

Example 10

Antibody Code: 3-1A8

VH
DNA (SEQ ID NO: 37)

CAAATCCAGCTGGTACAATCTGGGGCTGAGGTGAAGAAGCCTGGGTCCT

CGGTGAAGGTCTCCTGCAAGGCTTCTGGAGGCACCTTCAGCAGCTATGC

TATCAGCTGGGTGCGACAGGCCCCTGGACAAGGGCTTGAGTGGATGGGA

GGGATCATCCCTATCTTTGGTACAGCAAACTACGCACAGAAGTTCCAGG

GCAGAGTCACGATTACCGCGGACGAATCCACGAGCACGGCCTACATGGA

GCTGAGCAGCCTGAGATCTGAGGACACGGCCGTGTATTACTGTGCGAGA

GACGGTTCGTATAGCAGCAGCTGGTACTCGTTTGACTACTGGGGCCAGG

GAACCCTGGTCACCGTCTCCTCA

AMINO ACID (SEQ ID NO: 38)

QIQLVQSGAEVKKPGSSVKVSCKASGGTFSSYAISWVRQAPGQGLEWMG

GIIPIFGTANYAQKFQGRVTITADESTSTAYMELSSLRSEDTAVYYCAR

DGSYSSSWYSFDYWGQGTLVTVSS

VL
DNA (SEQ ID NO: 39)

CAGTCTGCCCTGACTCAGCCTGCCTCCGTGTCTGGGTCTCCTGGACAGT

CGATCACCATCTCCTGCACTGGAACCAGCAGTGACGTCGGTGGTTATAA

CTATGTCTCCTGGTACCAACAGCACCCAGGCAAAGCCCCCAAACTCATG

ATTTATGATGTCAGTAATCGGCCCTCAGGGGTTTCTAATCGCTTCTCTG

GCTCCAAGTCTGGCAACACGGCCTCCCTGACCATCTCTGGGCTCCAGGC

TGAGGACGAGGCTGATTATTACTGCTCCTCATATGCAGGTGATATTAGT

TATGTACTGTTCGGCGGCGGGACCAAGCTGACCGTCCTA

AMINO ACID (SEQ ID NO: 40)

QSALTQPASVSGSPGQSITISCTGTSSDVGGYNYVSWYQQHPGKAPKLM

IYDVSNRPSGVSNRFSGSKSGNTASLTISGLQAEDEADYYCSSYAGDIS

YVLFGGGTKLTVL

Example 11

Antibody Code: 3-1B11

VH
DNA
(SEQ ID NO: 41)
GAAGTGCAGCTGGTGGAGTCTGGGGGAGGCTTGGTACAGCCTGGAGGGT
CCCTGAGACTCTCCTGTGCAGCCTCTGGATTCACTTTTAGTGACTATGA
CATGATCTGGGTCCGCCAGGCTCCAGGCAAGGGGCTGGAGTGGGTGGCA
GTTATATCATATGATGGAAGTAATAAATACTATGCAGACTCCGTGAAGG
GCCGATTCACCATCTCCAGAGACAATTCCAAGAACACGCTGTATCTGCA
AATGAACAGCCTGAGAGCTGAGGACACGGCTGTGTATTACTGTGCGAAA
GAGTTCTTTGGTGCTTTTGATATCTGGGGCCAAGGGACAATGGTCACCG
TCTCTTCA

AMINO ACID
(SEQ ID NO: 42)
EVQLVESGGGLVQPGGSLRLSCAASGFTFSDYDMIWVRQAPGKGLEWVA
VISYDGSNKYYADSVKGRFTISRDNSKNTLYLQMNSLRAEDTAVYYCAK
EFFGAFDIWGQGTMVTVSS

VL
DNA
(SEQ ID NO: 43)
TCTTCTGAGCTGACTCAGGACCCTGCTGTGTCGGTGGCCTTGGGACAGA
CAGTCACGATCACATGCCAAGGAGACAGCCTCAATTACTATTATGCAAA
CTGGTTCCAGCTGAAGCCAGGGCAGGCCCCTGTACTTGTCCTCTTTGGT
AAAAACAACCGGCCCTCAGGGATCCCAGACCGATTCTCTGGCTCCTACT
CGGGAAGCACAGCTTCCTTGACCATCACTGGGGCTCAGGCGGAAGATGA
CGCTGACTATTACTGTAATTCGCGGGACAGCGGTGGTAATCCTTGGGTG
TTCGGCGGAGGGACCAAGCTGACCGTCCTA

AMINO ACID
(SEQ ID NO: 44)
SSELTQDPAVSVALGQTVTITCQGDSLNYYYANWFQLKPGQAPVLVLFG
KNNRPSGIPDRFSGSYSGSTASLTITGAQAEDDADYYCNSRDSGGNPWV
FGGGTKLTVL

Example 12

Antibody Code: 4-1F3

VH
DNA
(SEQ ID NO: 45)
CAAATCCAGCTGGTACAATCTGGGGCTGAGGTGAAGAAGCCTGGGTCCT
CGGTGAAGGTCTCCTGCAAGGCTTCTGGAGGCACCTTCAGCAGCTATGC
TATCAGCTGGGTGCGACAGGCCCCTGGACAAGGGCTTGAGTGGATGGGA
AGGATCATCCCTATCCTTGGTATAGCAGACTACGCACAGAAGTTCCAGG
GCAGAGTCACGATTACCGCGGACAAATCCACGAGCACAGCCTACATGGA
ACTGAGTAGCCTGGGATCTGAGGACACGGCCGTGTATTTTTGTGCGAGA
GAGGGGGGATCCTTTAGGCACTTTGACTTCTGGGGCCAGGGAACCCTGG
TCACCGTCTCCTCA

AMINO ACID
(SEQ ID NO: 46)
QIQLVQSGAEVKKPGSSVKVSCKASGGTFSSYAISWVRQAPGQGLEWMG
RIIPILGIADYAQKFQGRVTITADKSTSTAYMELSSLGSEDTAVYFCAR
EGGSFRHFDFWGQGTLVTVSS

VL
DNA
(SEQ ID NO: 47)
CAGCCTGTGCTGACTCAGCCACCCTCAGTCTCTGGGGCCCCAGGGCAGA
GGGTCACCATCTCCTGCGCTGGGAGCGACCCCAACATCGGGACAGGTCA
TGATGTGCACTGGTACCAGCAACTTCCAGGAACAGCCCCCAAACTCGTC
ATCTATGGTAACACCAATCGGCCCTCAGGGGTCCCTGAGCGATTCACTG
CCTCCAAGTCTGGCACCTCAGCCTCCCTGGCCATCACTGGGCTCCAGGC
TGAGGATGAGGCTGATTATTACTGCCAGGCCTACGACAGGAGCCTGCGT
GGTTATGTCTTCGGGACTGGGACCAAGGTCACCGTCCTG

AMINO ACID
(SEQ ID NO: 48)
QPVLTQPPSVSGAPGQRVTISCAGSDPNIGTGHDVHWYQQLPGTAPKLV
IYGNTNRPSGVPERFTASKSGTSASLAITGLQAEDEADYYCQAYDRSLR
GYVFGTGTKVTVL

Example 13

Antibody Code: 4-1G5

DNA
(SEQ ID NO: 49)
CAAATCCAGCTGGTACAGTCTGGTGCTGAAGTGAAGAAGCCTGGGGCCTC
AGTGAAGGTCTCCTGCAAGACTTCTGGTTACACCTTTACCAGCTATGGTA
TCAGCTGGGTGCGACAGGCCCCTGGACAAGGGCTTGAGTGGATGGGATGG
ATCAGCGCTTACAATGGTAACACAAACTATGCACAGAAGCTCCAGGGCAG
AGTCACCATGACCACAGACACATCCACGAGCACAGCCTACATGGAGCTGA
GGAGCCTGAGATCTGACGACACGGCCGTGTATTACTGTGCGAGAACTACA
GGTGACGAGTGGCTACGATTGGCTATAAATGACTACTGGGGCCAGGGAAC
CCTGGTCACCGTCTCCTCA

AMINO ACID
(SEQ ID NO: 50)
QIQLVQSGAEVKKPGASVKVSCKTSGYTFTSYGISWVRQAPGQGLEWMGW
ISAYNGNTNYAQKLQGRVTMTTDTSTSTAYMELRSLSDDTAVYYCARTT
GDEWLRLAINDYWGQGTLVTVSS

VL
DNA
(SEQ ID NO: 51)
GATATTGTGATGACACAGTCTCCCCTCTCCCTGCCCGTCACCCCTGGAGA
GCCGGCCTCCATCTCCTGCAGGTCTAGTCTGCGCCTCATGCATCCTAATG
GACTCAACTATTTGGATTGGTACCTGCAGAAGCCAGGGCAGTCTCCACAG
CTCCTAATCTTTTTGGGTTCTCAGCGGGCCTCCGGGGTCCCTGACAGGTT

CAGTGGCAGTGGATCAGGCACAGATTTTACACTGAAAATCAGCAGAGTGG

AGGCTGAGGATGTTGGCATTTATTACTGCATGCAAGCTCTAGAACCTCCG

TACACTTTTGGCCAGGGGACCAAGCTGGAGATCAAA

AMINO ACID
(SEQ ID NO: 52)
DIVMTQSPLSLPVTPGEPASISCRSSLRLMHPNGLNYLDWYLQKPGQSPQ

LLIFLGSQRASGVPDRFSGSGSGTDFTLKISRVEAEDVGIYYCMQALEPP

YTFGQGTKLEIK

Example 14

Antibody Code: 4-1C9

VH
DNA
(SEQ ID NO: 53)
CAGGTCCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACGAATCCACGAGCACAGCCTACATGGAGCTGA

GCAGCCTGAGATCTGAGGACACGGCCGTGTATTACTGTGCGAGAGATCCC

GGGTATAGCAGTGGCTGGAAAGATGATGCTTTTGATATCTGGGGCCAAGG

GACAATGGTCACCGTCTCTTCA

AMINO ACID
(SEQ ID NO: 54)
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARDP

GYSSGWKDDAFDIWGQGTMVTVSS

VL
DNA
(SEQ ID NO: 55)
GAAATTGTGATGACACAGTCTCCAGGCACCCTGTCTTTGTCTCCAGGGGA

TACAGCCTCCCTCTCCTGCAGGGCCAGTCAGACTGTTAGCAGCAACTACT

TAGCCTGGTACCAACAGAAACCTGGCCAGGCTCCCAGGCTCCTCATCTAT

GATACATCCAACAGGGCCGCTGGCATCCCGGCCAGGTTCAGTGGCAGTGG

GTCTGGGACAGACTTCACTCTCACCATCAGTAGCCTAGAGCCTGAAGATT

TTGCAGTGTATTACTGTCAGCAGTACGGTAGCTCACTCTGGACGTTCGGC

CAAGGGACCAAGGTGGAAATCAAA

AMINO ACID
(SEQ ID NO: 56)
EIVMTQSPGTLSLSPGDTASLSCRASQTVSSNYLAWYQQKPGQAPRLLIY

DTSNRAAGIPARFSGSGSGTDFTLTISSLEPEDFAVYYCQQYGSSLWTFG

QGTKVEIK

Example 15

Antibody Code: 11-A4

VH
DNA
(SEQ ID NO: 57)
CAGGTGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACGAATCCACGAGCACAGCCTACATGGAGCTGA

GCAGCCTGAGATCTGAGGACACGGCCGTGTATTACTGTGCGAGAGCGGGG

CAGCAGCTGGTAGCCCTTGGTACTACTGGGGCCAGGGAACCCTGGTCAC

CGTCTCCTCA

AMINO ACID
(SEQ ID NO: 58)
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARAG

QQLVALWYYWGQGTLVTVSS

VL
DNA
(SEQ ID NO: 59)
CAGTCTGCCCTGACTCAGCCTCCCTCCGCGTCCGGGTCTCGTGGACAGTC

AGTCTCCATCTCCTGCAGTGGAAGTCGCAGTGACATTGGATATTATAACT

ATGTCTCCTGGTATCAACAACACCCAGGCAAAGCCCCCAAACTCATCATT

TTTGACGTCAATAAGCGGCCCTCAGGGGTCCCTGATCGCTTCTCTGGCTC

CAAGTCTGGCAACACGGCCTCCCTGACCGTCTCTGGCCTCCAGCCTGAGG

ATGAGGCTGACTATTATTGCGCCTCTTATGGAGGCAGGAACAATTTGCTT

TTTGGCGGAGGGACTCAACTGACCGTCTTA

AMINO ACID
(SEQ ID NO: 60)
QSALTQPPSASGSRGQSVSISCSGSRSDIGYYNYVSWYQQHPGKAPKLII

FDVNKRPSGVPDRFSGSKSGNTASLTVSGLQPEDEADYYCASYGGRNNLL

FGGGTQLTVL

Example 16

Antibody Code: 21-A1

VH
DNA
(SEQ ID NO: 61)
CAGGTGCAACTGCAGGAGTCGGGCCCAGGACTGGTGGAGCCTTCGGAGAC

CCTGTCCCTCACCTGCACTGTCTCTGGTGGCTCCATCAGTAGTTTCTACT

GGAGCTGGATCCGGCAGCCCCCAGGGAAGGGACTGGAGTGGATTGGCTAT

ATCAATTACAGTGGGAGCACCAACTACAACCCCTCCCTCAAGAGTCGAGT

CACCATATCAGTAGACACGTCCAAGAACCAGTTCTCCCTGAAGCTGAGCT

CTGTGACCGCCGCAGACACGGCTGTGTATTACTGTGCGAGACAGATATTA

-continued
TGGTTCGGGGAGTTAAGGTGGTTCGACCCCTGGGGCCAGGGAACCCTGGT
CACCGTCTCCTCA

AMINO ACID
(SEQ ID NO: 62)
QVQLQESGPGLVEPSETLSLTCTVSGGSISSFYWSWIRQPPGKGLEWIGY
INYSGSTNYNPSLKSRVTISVDTSKNQFSLKLSSVTAADTAVYYCARQIL
WFGELRWFDPWGQGTLVTVSS

VL
DNA
(SEQ ID NO: 63)
CAGTCTGCCCTGACTCAGCCTCCCTCCGCGTCCGGGTCTCCTGGACAGTC
AGTCACCATCTCCTGCACTGGAACCAGCAGTGACATTGGTGGTTATAACT
ATGTCTCCTGGTACCAACTGCGCCCAGGCAAAGCCCCCAAACTCATGATT
TATGACGTCACCAAGCGGCCCTCAGGGGTCCCTGATCGCTTCTCTGGCTC
CAAGTCTGGCAACACGGCCTCCCTGACCGTCTCTGGGCTCCAGGCTGAGG
ATGAGGCTGATTATTACTGCAGCTCATATGCAGGCAGCAACAATGTGGTA
TTCGGCGGAGGGACCAAGCTGACCGTCCTA

AMINO ACID
(SEQ ID NO: 64)
QSALTQPPSASGSPGQSVTISCTGTSSDIGGYNYVSWYQLRPGKAPKLMI
YDVTKRPSGVPDRFSGSKSGNTASLTVSGLQAEDEADYYCSSYAGSNNVV
FGGGTKLTVL

Example 17

Antibody Code: 21-H12

VH
DNA
(SEQ ID NO: 65)
CAAGTCCAGCTGGTACAGTCTGGGGCTGAGGTGAAGAAGCCTGGGGCCTC
GGTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAG
AGTCACGATTACCGCGGACGAATCCACGAGCACAGCCTACATGGAGCTGA
GCAGCCTGAGATCTGAGGACACGGCCGTGTATTACTGTGCGAGAAATCCC
TACGGTTTCAACTGGTTCGACCCCTGGGGCCAGGGAACCCTGGTCACCGT
CTCCTCA

AMINO ACID
(SEQ ID NO: 66)
QVQLVQSGAEVKKPGASVKVSCKASGGTFSSYAISWVRQAPGQGLEWMGG
IIPIFGTANYAQKFQGRVTITADESTSTAYMELSSLRSEDTAVYYCARNP
YGFNWFDPWGQGTLVTVSS

VL
DNA
(SEQ ID NO: 67)
AATTTTATGCTGACTCAGCCCCACTCTGTGTCGGAGTCTCCGGGGAAGAC
GGTAACCATCTCCTGCACCCGCAGCAGTGGCAGCATTGCCAGCAACTATG
TGCAGTGGTACCAGCAGCGCCCGGGCAGTGCCCCCACCACTGTGATCTAT

-continued
GAGGATAACCAAAGACCCTCTGGGGTCCCTGATCGGTTCTCTGGCTCCAT
CGACAGCTCCTCCAACTCTGCCTCCCTCACCATCTCCGGACTGAAGACTG
AGGACGAGGCTGACTACTACTGTCAGTCTTATGATGGCTTCAATCAGGTG
TTCGGCGGAGGGACCAAGCTGACCGTCCTA AMINO ACID
(SEQ ID NO: 68)
NFMLTQPHSVSESPGKTVTISCTRSSGSIASNYVQWYQQRPGSAPTTVIY
EDNQRPSGVPDRFSGSIDSSSNSASLTISGLKTEDEADYYCQSYDGFNQV
FGGGTKLTVL

Example 18

Antibody Code: 7-D12

VH
DNA
(SEQ ID NO: 69)
CAAATGCAGCTGGTACAGTCTGGGGCTGAGGTGAAGAAGCCTGGGTCCTC
GGTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAG
AGTCACGATTACCGCGGACAAATCCACGAGCACAGCCTACATGGAGCTGA
GCAGCCTGAGATCTGAGGACACGGCCGTGTATTACTGTGCGAGAACCGGT
AGTAGTGGTTATGTACGTTGGAGCAACTGGTTCGACCCCTGGGGCCAGGG
AACCCTGGTCACCGTCTCCTCA

AMINO ACID
(SEQ ID NO: 70)
QMQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARTG
SSGYVRWSNWFDPWGQGTLVTVSS

VL
DNA
(SEQ ID NO: 71)
GACATCCAGATGACCCAGTCTCCCTCCACCCTGTCTGCATTTGTAGGAGA
CAGAGTCACCATCACTTGCCGGGCCAGTGAGAGTATTAGTAGGTGGTTGG
CCTGGTATCAGCAGAAACCAGGGAAAGCCCCTAAACTCCTAATCTCTAAG
ACGTCTAATTTAGAAAGCGGGGTCCCGTCAAGGTTCAGTGGCGCTGGATC
TGGGACAGATTTCACTCTCACCATTAGCAGTCTGCAACCTGAGGATTTTG
CAACTTACTTCTGTCAACAGGGTTCCAAAATGCCTCCGACTTTCGGCGGA
GGGACCAAGGTGGAGATCAAG

AMINO ACID
(SEQ ID NO: 72)
DIQMTQSPSTLSAFVGDRVTITCRASESISRWLAWYQQKPGKAPKLLISK
TSNLESGVPSRFSGAGSGTDFTLTISSLQPEDFATYFCQQGSKMPPTFGG
GTKVEIK

Example 19

Antibody Code: 9-E3

VH
DNA
(SEQ ID NO: 73)
CAGGTGCAGCTGGTGCAGTCTGGGGCTGAGGTGAAGAAGCCTGGGTCCTC
GGTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAG
AGTCACGATTACCGCGGACGAATCCACGAGCACAGCCTACATGGAGCTGA
GCAGCCTGAGATCTGAGGACACGGCCGTGTATTACTGTGCGAGAGGGGCC
TACGGTGGTAACTCCGCTTTTGACTACTGGGGCCAGGGAACCCTGGTCAC
CGTCTCCTCA

AMINO ACID
(SEQ ID NO: 74)
QVQLVQSGAEVKKPGSSVKVSCKASGGTFSSYAISWVRQAPGQGLEWMGG
IIPIFGTANYAQKFQGRVTITADESTSTAYMELSSLRSEDTAVYYCARGA
YGGNSAFDYWGQGTLVTVSS

VL
DNA
(SEQ ID NO: 75)
CAGTCTGTGCTGACGCAGCCGCCCTCAGTGTCTGGGGCCCCAGGGCAGAG
GGTCACCATCTCCTGCACTGGGAGCAGCTCCAACATCGGGGCAGGTTATG
ATGTACACTGGTACCAGCAGCTTCCAGGAACAGCCCCCAAACTCCTCATG
TACAGTAATGATCAGCGGCCCTCAGGGGTCACTGAGCGATTCTCTGGCTC
CAAGTCTGGCACCTCAGCCTCCCTGGCCATCAGTGGGCTCCAGTCTGAAG
ATGAGGGTGATTACTACTGCCAGTCCTATGACAGAAGCCTGAGAGGTTCG
GTCTTCGGCGGAGGGACCAAGCTGACCGTCCTC

AMINO ACID
(SEQ ID NO: 76)
QSVLTQPPSVSGAPGQRVTISCTGSSSNIGAGYDVHWYQQLPGTAPKLLM
YSNDQRPSGVTERFSGSKSGTSASLAISGLQSEDEGDYYCQSYDRSLRGS
VFGGGTKLTVL

Example 20

Antibody Code: 10-A6

VH
DNA
(SEQ ID NO: 77)
GAGGTGCAGCTGGTGCAGTCTGGGGCTGAGGTGAAGAAGCCTGGGGCCTC
AGTGAAGGTTTCCTGCAAGGCTTCTGGTTACACCTTTACCAGCTATGGTA
TCAGCTGGGTGCGACAGGCCCCTGGACAAGGGCTTGAGTGGATGGGATGG
ATCAGCGCTTACAATGGTAACACAAACTATGCACAGAAGCTCCAGGGCAG
AGTCACCATGACCACAGACACATCCACGAGCACAGCCTACATGGAGCTGA
GGAGCCTGAGATCTGACGACACGGCCGTGTATTACTGTGCGAGAGATTCC
ATAGCAGCAGCTGGTACTCCGTTCGACTACTGGGGCCAGGGAACCCTGGT
CACCGTCTCCTCA

AMINO ACID
(SEQ ID NO: 78)
EVQLVQSGAEVKKPGASVKVSCKASGYTFTSYGISWVRQAPGQGLEWMGW
ISAYNGNTNYAQKLQGRVTMTTDTSTSTAYMELRSLRSDDTAVYYCARDS
IAAAGTPFDYWGQGTLVTVSS

VL
DNA
(SEQ ID NO: 79)
AATTTTATGCTGACTCAGCCCCACTCTGTGTCGGAGTCTCCGGGGAAGAC
GGTCACCATCTCCTGCACCCGCAGCAGTGGCATCATTGCCAGCAAATATG
TGCACTGGTACCAGCAGCGCCCGGGCAGTGCCCCCACCACTGTGATCTAT
GAGGATAACCAAAGACCGTCTGGGGTCCCTGATCGATTCTCTGGCTCCAT
CGACAACTCCTCCAACTCTGCCTCCCTCACCATCTCTGGACTGCAGACTG
AGGACGAGGCTGACTACTACTGTCAGTCTCATGACGGCATCAATCAGGTT
TTCGGCGGAGGGACCAAGGTCACCGTCCTA

AMINO ACID
(SEQ ID NO: 80)
NFMLTQPHSVSESPGKTVTISCTRSSGIIASKYVHWYQQRPGSAPTTVIY
EDNQRPSGVPDRFSGSIDNSSNSASLTISGLQTEDEADYYCQSHDGINQV
FGGGTKVTVL

Example 21

Antibody Code: 12-A4

VH
DNA
(SEQ ID NO: 81)
GAGGTGCAGCTGGTGGAGTCCCGGGGAGGCTTGGTACAGCCGGGGGGGTC
CCTGAGACTCTCCTGTGTAACTTCTGGATTCAGCTTTAACAACTATGCCA
TGAACTGGGTCCGCCAGGCTCCGGGGAAGGGGCTGGAGTGGGTCTCAGCT
GTTAGTGGTAGTGGTGGTACCACATACTACGCAGACTCCGTGAAGGGCCG
GTTCACCATCTCCAGAGACAATTCCAAGAACACGCTGTTTGTGCAGATGG
ACAGCCTGAGAGCTGAGGACACGGCTGTGTATTACTGTGCGAAAGGACTT
TTCCCTACGATTTTTGGAGTAGGAGCAATGTTTGACTACTGGGGCCAGGG
AACCCTGGTCACCGTCTCCTCA

AMINO ACID
(SEQ ID NO: 82)
EVQLVESRGGLVQPGGSLRLSCVTSGFSFNNYAMNWVRQAPGKGLEWVSA
VSGSGGTTYYADSVKGRFTISRDNSKNTLFVQMDSLRAEDTAVYYCAKGL
FPTIFGVGAMFDYWGQGTLVTVSS

VL
DNA
(SEQ ID NO: 83)
TCTTCTGAGCTGACTCAGCCACCCTCAGCGTCTGGGACCCCCGGGCAGAG
GGTCACCATCTCTTGTTCTGGAAGCAGCTCCAACATCGGAAGTAATGCTG
TTAACTGGTATCAGCAGCTCCCAGGAACGGCCCCCAAACTCCTCATCTAT

-continued

GATAATAATCACCGGCCCTCAGGGGTCCCTGACCGATTCTCTGGCTCCAA

GTCTGGCACCTCAGCCTCCCTGGCCATCAGTGGGCTCCAGTCTGAGGATG

AGGCTGATTATTATTGTGCAGCATGGGATGACACCATTCCTGGTGTGCTA

TTCGCCGGAGGGACCAAGCTGACCGTCCTA

AMINO ACID (SEQ ID NO: 84)
SSELTQPPSASGTPGQRVTISCSGSSSNIGSNAVNWYQQLPGTAPKLLIY

DNNHRPSGVPDRFSGSKSGTSASLAISGLQSEDEADYYCAAWDDTIPGVL

FAGGTKLTVL

Example 22

Antibody Code: 14-G10

VH
DNA (SEQ ID NO: 85)
GAAGTGCAGCTGGTGGAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACGAATCCACGAGCACAGCCTACATGGAGCTGA

GCAGCCTGAGATCTGAGGACACGGCCGTGTATTACTGTGCGAGAGGTGTT

TCTTACTACTACGGTATGGACGTCTGGGGCCAAGGGACCACGGTCACCGT

CTCCTCA

AMINO ACID (SEQ ID NO: 86)
EVQLVESGAEVKKPGSSVKVSCKASGGTFSSYAISWVRQAPGQGLEWMGG

IIPIFGTANYAQKFQGRVTITADESTSTAYMELSSLRSEDTAVYYCARGV

SYYYGMDVWGQGTTVTVSS

VL
DNA (SEQ ID NO: 87)
CAGGCTGTGCTGACTCAGCCACCCTCGGTGTCCGTGTCCCCAGGACAGAC

AGCCATCATCTCCTGTTCTGGACATAAATTGGGTGATAAGTATGTTTCCT

GGTATCAACAGCAGCCAGGCCAGTCCCCTGTGCTGGTCCTCTTTCAGGAT

ACCAAGCGGCCCTCAGGGATCCCTGAGCGATTCTCTGGCTCCAACTCTGG

GAACACAGCCACTCTGACCATCAGCGCGACCCAGGCTGCGGATGAGGCTG

ACTATTACTGTCAGGCGGGGACACCAAGTCTGTGATCTTCGGCGGCGGG

ACCAAGCTGACCGTCCTA

AMINO ACID (SEQ ID NO: 88)
QAVLTQPPSVSVSPGQTAIISCSGHKLGDKYVSWYQQQPGQSPVLVLFQD

TKRPSGIPERFSGSNSGNTATLTISATQAADEADYYCQAGDTKSVIFGGG

TKLTVL

Example 23

Antibody Code: 22-A6

VH
DNA (SEQ ID NO: 89)
CAGGTTCAGGTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGGCAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACGAATCCACGAGCACAGCCTACATGGAGCTGA

GCAGCCTGAGATCTGAGGACACGGCCGTGTATTACTGTGCGAGAGGATAC

AGCTATGGTTCAGGACACCTTGACTACTGGGGCCAGGGAACCCTGGTCAC

CGTCTCCTCA

AMINO ACID (SEQ ID NO: 90)
QVQVVQSGAEVKKPGSSVKVSCKASGGTFSSYAISWVRQAPGQGLEWMGG

IIPIFGTANYAQKFQGRVTITADESTSTAYMELSSLRSEDTAVYYCARGY

SYGSGHLDYWGQGTLVTVSS

VL
DNA (SEQ ID NO: 91)
GACATCCAGATGACCCAGTCTCCATCCTCCCTGTCTGCATCTGTAGGAGA

CAGAGTCACCATCACTTGCCAGGCGAGTCAGGACATTAGCAACTATTTAA

ATTGGTATCAGCAGAAACCAGGGAAAGCCCCTAAGCTCCTGATCTACGAT

GCATCCAATTTGGAAACAGGGGTCCCATCAAGGTTCAGTGGCAGTGGATC

TGGGACAGATTTCGCTCTCACCATCAGCAGTCTCCAACCTGAAGATTTTG

CAACTTATTACTGTCTACAGCATAATAGTTACCCTCGGACTTTTGGCCAG

GGGACCAAGCTGGAGATCAAA

AMINO ACID (SEQ ID NO: 92)
DIQMTQSPSSLSASVGDRVTITCQASQDISNYLNWYQQKPGKAPKWYDAS

NLETGVPSRFSGSGSGTDFALTISSLQPEDFATYYCLQHNSYPRTFGQGT

KLEIK

Example 24

Antibody Code: 35-B1

VH
DNA (SEQ ID NO: 93)
GAGGTGCAGCTGGTGCAGTCTGGGGCTGAGGTGAAGAAGCCTGGGGCCTC

AGTGAAGGTCTCCTGCAAGGCTTCTGGATACACCTTCACCGGCTACTATA

TGCACTGGGTGCGACAGGCCCCTGGACAAGGGCTTGAGTGGATGGGATGG

ATGAACCCTAACAGTGGTGACACAGCCTATACACAGAACTTCCAGGGCAG

AGTCACCATGACCAGGAACCCCTCCATAAGCACAGCCTACATGGAGCTGA

GCAACCTGAGATCTGAGGACACGGCCGTGTATTACTGTGCGAGAGGCCGG

```
-continued
GGGTTCGCGGAGAAGCCCCTTGGGTACTGGGGCCAGGGAACCCTGGTCAC

CGTCTCCTCA

AMINO ACID
                                              (SEQ ID NO: 94)
EVQLVQSGAEVKKPGASVKVSCKASGYTFTGYYMHWVRQAPGQGLEWMGW

MNPNSGDTAYTQNFQGRVTMTRNPSISTAYMELSNLRSEDTAVYYCARGR

GFAEKPLGYWGQGTLVTVSS

VL
DNA
                                              (SEQ ID NO: 95)
GATATTGTGATGACTCAGTCTCCAGACTCCCTGGCTGTGTCTCTGGGCGG

GAGGGCCACCATCAACTGCAAGTCCAGCCAGAGTATTTTATCCAGCTCCA

ATAATAAGAACTATTTAGCTTGGTACCAGCAGAAACCAGGTCAGCCTCCT

AAGCTGCTCATTTACTGGGCATCTACCCGGGAATCCGGGGTCCCTGACCG

GTTCAGCGGCAGCGGGTCTGGGACAGATTTCACTCTCACCATCAGCAGCC

TGCAGGCTGAAGATGTGGCAGTTTATTACTGTCAGCAATATTATAGTACT

CCTCCGACATTCGGCCAAGGGACCAAGGTGGAAATCAAA

AMINO ACID
                                              (SEQ ID NO: 96)
DIVMTQSPDSLAVSLGGRATINCKSSQSILSSSNNKNYLAWYQQKPGQPP

KLLIYWASTRESGVPDRFSGSGSGTDFTLTISSLQAEDVAVYYCQQYYST

PPTFGQGTKVEIK
```

Example 25

Antibody Code: 3-1F4

```
DNA
                                              (SEQ ID NO: 97)
GAGGTGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACGAATCCACGAGCACAGCCTACATGGAGCTGA

GCAGCCTGAGATCTGAGGACACGGCCGTGTATTACTGTGCGAGGGCCCCT

CGAGGGCAGTGGCTGGTTCACTACTTTGACTACTGGGGCCAGGGAACCCT

GGTCACCGTCTCCTCA

AMINO ACID
                                              (SEQ ID NO: 98)
EVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARAP

RGQWLVHYFDYWGQGTLVTVSS

VL
DNA
                                              (SEQ ID NO: 99)
GAAATTGTGTTGACGCAGTCTCCAGCCACCCTCTCTCTGTCTCCAGGGGA

AAGAGCCACCCTCTCCTGCTGGGCCAGTCAGGATGTTAGCAACTACTTAG

CCTGGTACCAACAGAAGCCTGGCCAGGCTCCCAGGCTCCTCATCTATGAT

GCATCCAACAGGGCCACTGGCATCCCAGCCAGGTTCAGCGGCAGTGGGTC

TGGGACAGACTTCACTCTCACCATCAGCAGCCTAGAGCCTGAAGATTTTG

CAGTGTATTACTGTCAGCAACGTAGCAACTGGCCTCTCACTTTCGGCGGC

GGGACCAAGGTGGAGCTCAAA

AMINO ACID
                                              (SEQ ID NO: 100)
EIVLTQSPATLSLSPGERATLSCWASQDVSNYLAWYQQKPGQAPRLLIYD

ASNRATGIPARFSGSGSGTDFTLTISSLEPEDFAVYYCQQRSNWPLTFGG

GTKVELK
```

Example 26

Antibody Code: 4-1B3

```
VH
DNA
                                              (SEQ ID NO: 101)
CAGGTTCAGCTGGTGCAGTCTGGAGCTGAGGTGAAGAAGCCTGGGGCCTC

AGTGAAGGTCTCCTGCAAGGCTTCTGGTTACACCTTTACCAGCTATGGTA

TCAGCTGGGTGCGACAGGCCCCTGGACAAGGGCTTGAGTGGATGGGATGG

ATCAGCGCTTACAATGGTAACACAAACTATGCACAGAAGCTCCAGGGCAG

AGTCACCATGACCACAGACACATCCACGAGCACAGCCTACATGGAGCTGA

GGAGCCTGAGATCTGACGACACGGCCGTGTATTACTGTGCGAGAGAGTCC

TACTCGTCCGCAGGTATTGACTACTGGGGCCAGGGAACCCTGGTCACCGT

CTCCTCA

AMINO ACID
                                              (SEQ ID NO: 102)
QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCARES

YSSAGIDYWGQGTLVTVSS

VL
DNA
                                              (SEQ ID NO: 103)
GATATTGTGATGACTCAGTCTCCACTCTCCCTGCCCGTCACCCCTGGAGA

GCCGGCCTCCATCTCCTGCAGGTCTAGTCAGACCCTCCTGCATAGTAATG

GATTCAACTATTTGGATTGGTACCTGCAGAAGCCAGGGCAGTCTCCACAA

CTCCTGATGTATTTGGGCTCTAGCCGGGCCTCCGGGGTCCCTGACAGGTT

CAGTGGCAGTGGATCGGGCACAGATTTCACACTGAAAATCAGCAGAGTGG

AGGCTGAGGATGTTGGGGTTTATTACTGCATGCAAACTCTACAAACTCCT

CCGGCTTTCGGCGGAGGGACCAAGGTGGAGATCAAA

AMINO ACID
                                              (SEQ ID NO: 104)
DIVMTQSPLSLPVTPGEPASISCRSSQTLLHSNGFNYLDWYLQKPGQSPQ

LLMYLGSSRASGVPDRFSGSGSGTDFTLKISRVEAEDVGVYYCMQTLQTP

PAFGGGTKVEIK
```

Example 27

Antibody Code: 21-G1

VH
DNA
(SEQ ID NO: 105)
CAGGTCCAGCTGGTGCAGTCTGGGGCTGAGGTGAAGAAGCCTGGGGCCTC

AGTGACGATTTCCTGCGAGGCGTCTGGATACAACTTCATCAGCTACTATA

TACACTGGGTGCGACAGGCCCCTGGACAAGGCCTTGAGTGGATGGGATTC

GTCGTCCCTAGTGGTGGTGCCGCAGGCTACACACAGAAGTTCCAGGGCAG

ACTCACCGTGACCAGGGACACGTCCACGAGCACAGTCTACATGGACCTGA

ACAGCCTGACATCTGACGACACGGCCGTGTATTACTGTGTGCGAGAAATG

AGTGGTGGCTGGTTTGATTTCTGGGGCCAGGGAACCCTGGTCACCGTCTC

CTCG

AMINO ACID
(SEQ ID NO: 106)
QVQLVQSGAEVKKPGASVTISCEASGYNFISYYIHWVRQAPGQGLEWMGF

VVPSGGAAGYTQKFQGRLTVTRDTSTSTVYMDLNSLTSDDTAVYYCVREM

SGGWFDFWGQGTLVTVSS

VL
DNA
(SEQ ID NO: 107)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAACAGAGTTACAGTACCCCGATCACCTTCGGCCAA

GGGACACGACTGGAGATTAAA

AMINO ACID
(SEQ ID NO: 108)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPITFGQ

GTRLEIK

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

---

The invention claimed is:

1. An antigen-binding polypeptide that binds to a human PD-L1 epitope, comprising a heavy chain variable domain and a light chain variable domain having respective PD-L1-specific sequences, wherein the respective PD-L1-specific sequences consist of a sequence pairing selected from the group consisting of:
(a) SEQ ID NO: 18 and SEQ ID NO: 20;
(b) SEQ ID NO: 42 and SEQ ID NO: 44; and
(c) SEQ ID NO: 34 and SEQ ID NO: 36.

2. An antigen-binding polypeptide that binds to a human PD-L1 epitope, comprising a heavy chain variable domain and a light chain variable domain, wherein:
(a) the heavy chain variable domain comprises a sequence that is SEQ ID NO: 18 and the light chain variable domain comprises a sequence that is SEQ ID NO: 20; or
(b) the heavy chain variable domain comprises a sequence that is SEQ ID NO: 42 and the light chain variable domain comprises a sequence that is SEQ ID NO: 44.

3. The antigen-binding polypeptide of claim 1 wherein the polypeptide is a fully human antibody.

4. The antigen-binding polypeptide of claim 3, wherein the polypeptide further comprises a human constant region, and wherein the human constant region has ADCC and/or CDC activities.

5. An antibody that binds to a human PD-L1 epitope, comprising a pair of the heavy chain variable domain and the light chain variable domain of claim 1.

6. A pharmaceutical composition comprising the antigen-binding polypeptide of claim 1, and a pharmaceutically acceptable excipient, carrier or diluent.

7. An antigen-binding polypeptide that binds to a human PD-L1 epitope, comprising a heavy chain variable domain and a light chain variable domain, wherein the heavy chain variable domain comprises a sequence that is SEQ ID NO: 34 and the light chain variable domain comprises a sequence that is SEQ ID NO: 36.

8. A nucleic acid molecule that encodes the antigen-binding polypeptide of claim 1, wherein the nucleic acid molecule is a DNA molecule or RNA molecule.

9. The nucleic acid molecule of claim 8, wherein the nucleic acid molecule consists essentially of a sequence pairing selected from the group consisting of: (a) SEQ ID NO: 17 and SEQ ID NO: 19; (b) SEQ ID NO: 33 and SEQ ID NO: 35; and (c) SEQ ID NO: 41 and SEQ ID NO: 43.

10. A mammalian expression system that produces the polypeptide of claim 1.

11. A method of treating a human subject in need thereof for a cancer therapeutically, said method comprising administering to said subject a therapeutically effective amount of a pharmaceutical composition comprising a pharmaceutically acceptable excipient, carrier or diluent, and an antigen-binding polypeptide that binds to a human PD-L1 epitope, wherein the polypeptide comprises a heavy chain variable domain and a light chain variable domain, and wherein the respective sequences thereof consist essentially of a sequence pairing selected from the group consisting of:
(a) SEQ ID NO: 18 and SEQ ID NO: 20;
(b) SEQ ID NO: 42 and SEQ ID NO: 44; and
(c) SEQ ID NO: 34 and SEQ ID NO: 36.

12. The method of claim 11, further comprising administering in combination with a therapy selected from the group consisting of: (a) antibodies targeting other immunosuppressive pathways; (b) chemotherapy or radiation therapy; (c) other mechanisms of blocking immunosuppressive pathways; and (d) other immunotherapy agents.

13. The method of claim 11, wherein said cancer is selected from the group consisting of: ovarian cancer, colon cancer, breast cancer, lung cancer, myelomas, neuroblastic-derived CNS tumors, monocytic leukemias, B-cell derived leukemias, T-cell derived leukemias, B-cell derived lymphomas, T-cell derived lymphomas, mast cell derived tumors, melanoma, bladder cancer, gastric cancer, liver cancer, urothelial carcinoma, cutaneum carcinoma, renal cancer, head and neck cancer, pancreatic cancer, and combinations thereof.

14. The method of claim 13, wherein said cancer has at least a fraction of the tumor cells expressing detectable amount of PD-L1.

* * * * *

SEQUENCE LISTING

```
<160> NUMBER OF SEQ ID NOS: 108

<210> SEQ ID NO 1
<211> LENGTH: 357
<212> TYPE: DNA
<213> ORGANISM: Artificial Sequence
<220> FEATURE:
<223> OTHER INFORMATION: 4-1A2 VH

<400> SEQUENCE: 1
caggttcagc tggtgcagtc tggggactgag gtgaagaagc ctggggcctc    60
tcctgcaagg cttctggata caccttcacc agttatgata tcaactgggt gcgacaggcc   120
actggacaag gcttgagtg gatgggatgg atcaacccta acagtggtgg cacaaactat   180
gcacagaagt ttcagggcag ggtcaccatg accacagaca cttctacggg cacagcctac   240
atggagctga ggagcctgag atctgacgac acggccgtgt attactgtgc gagattttta   300
tggggttcgg ggagttatga ctactggggc cagggaaccc tggtcaccgt ctcctca     357

<210> SEQ ID NO 2
<211> LENGTH: 119
<212> TYPE: PRT
<213> ORGANISM: Artificial Sequence
<220> FEATURE:
<223> OTHER INFORMATION: 4-1A2 VH

<400> SEQUENCE: 2

Gln Val Gln Leu Val Gln Ser Gly Thr Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Thr Asp Thr Ser Thr Gly Thr Ala Tyr
65                  70                  75                  80

Met Glu Leu Arg Ser Leu Arg Ser Asp Asp Thr Ala Val Tyr Tyr Cys
                85                  90                  95

Ala Arg Phe Leu Trp Gly Ser Gly Ser Tyr Asp Tyr Trp Gly Gln Gly
            100                 105                 110

Thr Leu Val Thr Val Ser Ser
            115

<210> SEQ ID NO 3
<211> LENGTH: 321
<212> TYPE: DNA
<213> ORGANISM: Artificial Sequence
<220> FEATURE:
<223> OTHER INFORMATION: 4-1A2 VL

<400> SEQUENCE: 3
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagatttcg caacttacta ctgtcaacag acttacacat cccgcacac ttttgcccag      300 gggaccaacc tggagatcaa a                                               321

<210> SEQ ID NO 4
<211> LENGTH: 107
<212> TYPE: PRT
<213> ORGANISM: Artificial Sequence
<220> FEATURE:
<223> OTHER INFORMATION: 4-1A2 VL

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Phe Pro His
                85                  90                  95

Thr Phe Ala Gln Gly Thr Asn Leu Glu Ile Lys
            100                 105

<210> SEQ ID NO 5
<211> LENGTH: 360
<212> TYPE: DNA

<213> ORGANISM: Artificial Sequence
<220> FEATURE:
<223> OTHER INFORMATION: 4-1A12 VH

<400> SEQUENCE: 5

```
caagtccagc tggtacaatc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagattgg   300
atacagctat ggttaccct tgactactgg ggccaggaa ccctggtcac cgtctcctca    360
```

<210> SEQ ID NO 6
<211> LENGTH: 120
<212> TYPE: PRT
<213> ORGANISM: Artificial Sequence
<220> FEATURE:
<223> OTHER INFORMATION: 4-1A12 VH

<400> SEQUENCE: 6

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Trp Ile Gln Leu Trp Leu Pro Leu Asp Tyr Trp Gly Gln
            100                 105                 110
Gly Thr Leu Val Thr Val Ser Ser
        115                 120
```

<210> SEQ ID NO 7
<211> LENGTH: 321
<212> TYPE: DNA
<213> ORGANISM: Artificial Sequence
<220> FEATURE:
<223> OTHER INFORMATION: 4-1A12 VL

<400> SEQUENCE: 7

```
gacatccagt tgacccagtc tccatcctcc ctgtctgcat ctgtaggaga cagagtcacc    60
atcacttgcc gggcaagtca gagcattagc agctatttaa attggtatca acagaaacca   120
gggaaagccc ctaagctcct gatctatggt gcatccagtt tggaaagtgg ggtcccatca   180
aggttcagtg gcagtggatc tgggacagat ttcactctca ccatcagcag tctgcaacct   240
gaagattttg caacttacta ctgtcaacag agtcacagtt ccccccctca cttcggcgga   300
gggaccaagg tggacatcaa a                                              321
```

<210> SEQ ID NO 8
<211> LENGTH: 107
<212> TYPE: PRT
<213> ORGANISM: Artificial Sequence

<220> FEATURE:
<223> OTHER INFORMATION: 4-1A12 VL

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Ser Pro Leu
                85                  90                  95

Thr Phe Gly Gly Gly Thr Lys Val Asp Ile Lys
            100                 105

<210> SEQ ID NO 9
<211> LENGTH: 387
<212> TYPE: DNA
<213> ORGANISM: Artificial Sequence
<220> FEATURE:
<223> OTHER INFORMATION: 4-1B9 VH

<400> SEQUENCE: 9
gaagtgcagc tggtgcagtc tgggggaggc ttggtccagc ctggggaggtc cctgagactc      60 tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatttg     300
atcccgttgc gagatagtag ggggggtac tactacggta tggacgtctg gggccaaggg      360
accacggtca ccgtctcctc agggagt                                          387

<210> SEQ ID NO 10
<211> LENGTH: 127
<212> TYPE: PRT
<213> ORGANISM: Artificial Sequence
<220> FEATURE:
<223> OTHER INFORMATION: 4-1B9 VH

<400> SEQUENCE: 10

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ile Pro Leu Arg Asp Ser Arg Gly Gly Tyr Tyr Tyr

```
            100                 105                 110
Gly Met Asp Val Trp Gly Gln Gly Thr Thr Val Thr Val Ser Ser
            115                 120                 125

<210> SEQ ID NO 11
<211> LENGTH: 324
<212> TYPE: DNA
<213> ORGANISM: Artificial Sequence
<220> FEATURE:
<223> OTHER INFORMATION: 4-1B9 VL

<400> SEQUENCE: 11
tcttctgagc tgactcagga ccctgctgtg tctgtggcct tgggacagac agtcaggatc    60
acatgccaag agacagcct cagagactat tatgcaagct ggtaccagca gaagccagga    120
caggcccctg tacttgtcat ctatggtaaa acaaccggc cctcaggaat cccagaccga    180
ttctctggct ccagctcagg aaacacagct tccttgacca tcactgggac tcaggcggaa    240
gatgaggctg actattactg taactcccgt gacagcggtg cttaccatta tgtcttcgga    300
actgggacca aggtcaccgt ccta                                          324

<210> SEQ ID NO 12
<211> LENGTH: 108
<212> TYPE: PRT
<213> ORGANISM: Artificial Sequence
<220> FEATURE:
<223> OTHER INFORMATION: 4-1B9 VL

<400> SEQUENCE: 12

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asp Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Thr Gln Ala Glu
65                  70                  75                  80

Asp Glu Ala Asp Tyr Tyr Cys Asn Ser Arg Asp Ser Gly Ala Tyr His
                85                  90                  95

Tyr Val Phe Gly Thr Gly Thr Lys Val Thr Val Leu
            100                 105

<210> SEQ ID NO 13
<211> LENGTH: 360
<212> TYPE: DNA
<213> ORGANISM: Artificial Sequence
<220> FEATURE:
<223> OTHER INFORMATION: 4-1B12 VH

<400> SEQUENCE: 13
caaatccagc tggtgcagtc tggggggaggc gtggtccagc ctgggaggtc cctgagactc    60
tcctgtgcag cctctggatt caccttcagt agctatggca tgcactgggt ccgccaggct    120
ccaggcaagg ggctggagtg ggtggcagtt atatcatatg atggaagtaa taatactat    180 gcagactccg tgaagggccg attcaccatc tccagagaca attccaagaa cacgctgtat    240
ctgcaaatga acagcctgag agctgaggac acggctgtgt attactgtgc gaaaggaagt    300
attatagggg atggtgcttt tgatatctgg ggccaaggga caatggtcac cgtctcttca    360
```

<210> SEQ ID NO 14
<211> LENGTH: 120
<212> TYPE: PRT
<213> ORGANISM: Artificial Sequence
<220> FEATURE:
<223> OTHER INFORMATION: 4-1B12 VH

<400> SEQUENCE: 14

```
Gln Ile Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ile Ile Gly Asp Gly Ala Phe Asp Ile Trp Gly Gln
            100                 105                 110

Gly Thr Met Val Thr Val Ser Ser
        115                 120
```

<210> SEQ ID NO 15
<211> LENGTH: 333
<212> TYPE: DNA
<213> ORGANISM: Artificial Sequence
<220> FEATURE:
<223> OTHER INFORMATION: 4-1B12 VL

<400> SEQUENCE: 15

```
gatattgtga tgacccagtc tccactctcc ctgcccgtca cccttggaga gccggcctcc    60
atctcctgca ggtctagtca gaccctcctg cataatggat caactttttt ggattggtac   120
ctgcagaagc cagggcagtc tccacaactc ctgatgtatt tggcctctag ccgggcctcc   180
ggggtccctg acaggttcag tggcagtgga tcgggcacag atttcacact gaaaatcagc   240
agagtggagg ctgaggatgt tggggtttat tactgcatgc aaggtacaca ctggccgtac   300
acttttggcc aggggaccaa gctggatatc aaa                                 333
```

<210> SEQ ID NO 16
<211> LENGTH: 111
<212> TYPE: PRT
<213> ORGANISM: Artificial Sequence
<220> FEATURE:
<223> OTHER INFORMATION: 4-1B12 VL

<400> SEQUENCE: 16

```
Asp Ile Val Met Thr Gln Ser Pro Leu Ser Leu Pro Val Thr Leu Gly
1               5                   10                  15

Glu Pro Ala Ser Ile Ser Cys Arg Ser Ser Gln Thr Leu Leu His Asn
                20                  25                  30

Gly Phe Asn Phe Leu Asp Trp Tyr Leu Gln Lys Pro Gly Gln Ser Pro
            35                  40                  45

Gln Leu Leu Met Tyr Leu Ala Ser Ser Arg Ala Ser Gly Val Pro Asp
        50                  55                  60
```

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Met Gln Gly Thr
                85                  90                  95

His Trp Pro Tyr Thr Phe Gly Gln Gly Thr Lys Leu Asp Ile Lys
            100                 105                 110

<210> SEQ ID NO 17
<211> LENGTH: 354
<212> TYPE: DNA
<213> ORGANISM: Artificial Sequence
<220> FEATURE:
<223> OTHER INFORMATION: 4-1E8 VH

<400> SEQUENCE: 17
caaatccagc tggtacaatc tggggctgag gtgaagatgc ctggggcctc agtgacgatt    60
tcctgcgagg cgtctggata caacttcatc agctactata tacactgggt gcgacaggcc   120
cctggacaag gccttgagtg gatgggattc gtcgtcccta gtggtggtgc cgcaggctac   180
acacagaagt tccagggcag actcaccgtg accagggaca cgtccacgag cacagtctac   240
atggacctga acagcctgac atctgacgac acggccgtgt attactgtgt gcgagaaatg   300
agtggtggct ggtttgattt ctggggccag ggaaccctgg tcaccgtctc ctcg         354

<210> SEQ ID NO 18
<211> LENGTH: 118
<212> TYPE: PRT
<213> ORGANISM: Artificial Sequence
<220> FEATURE:
<223> OTHER INFORMATION: 4-1E8 VH

<400> SEQUENCE: 18

Gln Ile Gln Leu Val Gln Ser Gly Ala Glu Val Lys Met Pro Gly Ala
1               5                   10                  15

Ser Val Thr Ile Ser Cys Glu Ala Ser Gly Tyr Asn Phe Ile Ser Tyr
            20                  25                  30

Tyr Ile His Trp Val Arg Gln Ala Pro Gly Gln Gly Leu Glu Trp Met
        35                  40                  45

Gly Phe Val Val Pro Ser Gly Gly Ala Ala Gly Tyr Thr Gln Lys Phe
    50                  55                  60

Gln Gly Arg Leu Thr Val Thr Arg Asp Thr Ser Thr Ser Thr Val Tyr
65                  70                  75                  80

Met Asp Leu Asn Ser Leu Thr Ser Asp Asp Thr Ala Val Tyr Tyr Cys
                85                  90                  95

Val Arg Glu Met Ser Gly Gly Trp Phe Asp Phe Trp Gly Gln Gly Thr
            100                 105                 110

Leu Val Thr Val Ser Ser
        115

<210> SEQ ID NO 19
<211> LENGTH: 321
<212> TYPE: DNA
<213> ORGANISM: Artificial Sequence
<220> FEATURE:
<223> OTHER INFORMATION: 4-1E8 VL

<400> SEQUENCE: 19
gacatcgtga tgacccagtc tccatcctcc ctgtctgcat ctgtaggaga cagagtcacc    60
atcacttgcc gggcaagtca gggcattaga aatgatttag gctggtatca gcaaaaacca   120

| | |
|---|---|
| gggaaagccc ctaagctcct gatctatgct gcatccactt tgcaaagtgg ggtcccatca | 180 |
| aggttcagcg gcagtggatc tgggacagat tcactctcca ccatcagcag cctgcaggct | 240 |
| gaagatgtgg cagtttatta ctgtcagcaa tattatagta ctcctctcac tttcggccct | 300 |
| gggaccaaag tggatatcaa a | 321 |

<210> SEQ ID NO 20
<211> LENGTH: 107
<212> TYPE: PRT
<213> ORGANISM: Artificial Sequence
<220> FEATURE:
<223> OTHER INFORMATION: 4-1E8 VL

<400> SEQUENCE: 20

Asp Ile Val Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Thr Pro Leu
                85                  90                  95

Thr Phe Gly Pro Gly Thr Lys Val Asp Ile Lys
            100                 105

<210> SEQ ID NO 21
<211> LENGTH: 366
<212> TYPE: DNA
<213> ORGANISM: Artificial Sequence
<220> FEATURE:
<223> OTHER INFORMATION: 4-1G7 VH

<400> SEQUENCE: 21

| | |
|---|---|
| gaggtgcagc tggtgcagtc tggggctgag gtgaagaagc ctgggtcctc ggtgaaggtc | 60 |
| tcctgcaagg cttctggtta cacctttacc agctatggta tcagctgggt gcgacaggcc | 120 |
| cctggacaag gcttgagtg gatgggatgg atcagcgctt acaatggtaa cacaaactat | 180 |
| gcacagaagc tccagggcag agtcaccatg accacagaca catccacgag cacagcctac | 240 |
| atggagctga ggagcctgag atctgacgac acggccgtgt attactgtgc gagagcctca | 300 |
| ccggtacagc agcccatatg gtgggcggag tactggggcc agggaaccct ggtcaccgtc | 360 |
| tcctca | 366 |

<210> SEQ ID NO 22
<211> LENGTH: 122
<212> TYPE: PRT
<213> ORGANISM: Artificial Sequence
<220> FEATURE:
<223> OTHER INFORMATION: 4-1G7 VH

<400> SEQUENCE: 22

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala Ser Pro Val Gln Gln Pro Ile Trp Trp Ala Glu Tyr Trp
                100                 105                 110

Gly Gln Gly Thr Leu Val Thr Val Ser Ser
        115                 120

<210> SEQ ID NO 23
<211> LENGTH: 330
<212> TYPE: DNA
<213> ORGANISM: Artificial Sequence
<220> FEATURE:
<223> OTHER INFORMATION: 4-1G7 VL

<400> SEQUENCE: 23
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca aagcccccaa actcatgatt tctgatgtca gtaagcggcc ctcagggggtt    180 tctaatcgct tctctggctc caagtctggc aacacggcct ccctgaccat ctctgggctc     240
caggctgagg acgaggctga ttattactgc agctcatata caagcaacta cactttggta     300
ttcggcggag ggaccaagct gaccgtccta                                      330

<210> SEQ ID NO 24
<211> LENGTH: 110
<212> TYPE: PRT
<213> ORGANISM: Artificial Sequence
<220> FEATURE:
<223> OTHER INFORMATION: 4-1G7 VL

<400> SEQUENCE: 24

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
         35                  40                  45

Met Ile Ser Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Asn
                 85                  90                  95

Tyr Thr Leu Val Phe Gly Gly Gly Thr Lys Leu Thr Val Leu
                100                 105                 110

<210> SEQ ID NO 25
<211> LENGTH: 366
<212> TYPE: DNA
<213> ORGANISM: Artificial Sequence
<220> FEATURE:
<223> OTHER INFORMATION: 4-1H10 VH

<400> SEQUENCE: 25

```
cagctgcagc tacagcagtc cggagctgag gtgaagaagc ctgggtcctc ggtgaaggtc      60
tcctgcaagg ctcctggagg caccttcagc agctatgcta tcagctgggt gcgacaggcc     120
cctggacaag gcttgagtg gatgggaagg atcatcccta tccttggtat agcaaactac      180
gcacagaagt tccagggcag agtcacgatt accgcggaca atccacgag cacagcctac      240
atggagctga gcagcctgag atctgaagac acggccgtgt attactgtgc gagtcatggt     300
cgggcagcag ctggtaggta cgctatggac gtctggggcc aagggaccac ggtcaccgtc     360
tcctca                                                                366
```

<210> SEQ ID NO 26
<211> LENGTH: 122
<212> TYPE: PRT
<213> ORGANISM: Artificial Sequence
<220> FEATURE:
<223> OTHER INFORMATION: 4-1H10 VH

<400> SEQUENCE: 26

```
Gln Leu Gln Leu Gln Gln Ser Gly Ala Glu Val Lys Lys Pro Gly Ser
1               5                   10                  15
Ser Val Lys Val Ser Cys Lys Ala Pro Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ser His Gly Arg Ala Ala Ala Gly Arg Tyr Ala Met Asp Val Trp
            100                 105                 110
Gly Gln Gly Thr Thr Val Thr Val Ser Ser
        115                 120
```

<210> SEQ ID NO 27
<211> LENGTH: 330
<212> TYPE: DNA
<213> ORGANISM: Artificial Sequence
<220> FEATURE:
<223> OTHER INFORMATION: 4-1H10 VL

<400> SEQUENCE: 27

```
aattttatgc tgactcagcc ccactctgtg tcggattctc cggggaagac ggtaaccatc      60
tcctgcaccc gcagcagtgg cagcattgcc agcaactatg tgcagtggta ccagcagcgc     120
ccgggcagtg cccccaccac tgtgatctat gacgataagc aaagaccctc tggggtccct     180
gatcggttct cgggctccat cgacagctcc tccaactctg cctccctcac catctctgga     240
ctgacgactg aggacgaggc tgactactac tgtcagtcct tgatggcag cagtgtcatc      300
ttcggcggag ggaccaagct gaccgtcctg                                      330
```

<210> SEQ ID NO 28
<211> LENGTH: 110
<212> TYPE: PRT
<213> ORGANISM: Artificial Sequence
<220> FEATURE:
<223> OTHER INFORMATION: 4-1H10 VL

<400> SEQUENCE: 28

Asn Phe Met Leu Thr Gln Pro His Ser Val Ser Asp Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Asp Asp Lys Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Thr Thr Glu Asp Glu Ala Asp Tyr Tyr Cys Gln Ser Phe Asp Gly
                85                  90                  95

Ser Ser Val Ile Phe Gly Gly Gly Thr Lys Leu Thr Val Leu
            100                 105                 110

<210> SEQ ID NO 29
<211> LENGTH: 375
<212> TYPE: DNA
<213> ORGANISM: Artificial Sequence
<220> FEATURE:
<223> OTHER INFORMATION: 3-1H2 VH

<400> SEQUENCE: 29
caggttcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatccta tctttggtac agcaaactac      180
gcacagaagt tccagggcag agtcacgatt accgcggacg aatccacgag cacagcctac     240
atggagctga gcagcctgag atctgaggac acggccgtgt attactgtgc gagaaaggag     300
cgtttctatg atagtagtgg ttattacgat gcttttgata tctggggcca agggacaatg     360
gtcaccgtct cttca                                                      375

<210> SEQ ID NO 30
<211> LENGTH: 125
<212> TYPE: PRT
<213> ORGANISM: Artificial Sequence
<220> FEATURE:
<223> OTHER INFORMATION: 3-1H2 VH

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Glu Arg Phe Tyr Asp Ser Ser Gly Tyr Tyr Asp Ala Phe
            100                 105                 110

Asp Ile Trp Gly Gln Gly Thr Met Val Thr Val Ser Ser
            115                 120                 125

<210> SEQ ID NO 31
<211> LENGTH: 330
<212> TYPE: DNA
<213> ORGANISM: Artificial Sequence
<220> FEATURE:
<223> OTHER INFORMATION: 3-1H2 VL

<400> SEQUENCE: 31

| | |
|---|---|
| cagtctgccc tgactcagcc tcgctcagtg tccgggtctc ctgggcagtc agtcaccatc | 60 |
| tcctgcactg gaaccagcaa tgatgttggt ggttataact atgtctcctg gtaccaacag | 120 |
| cacccaggca agcccccaa actcatgatt tatgatgtca ctaagcggcc ctcaggggtc | 180 |
| cctgatcgct tctctggctc caagtctggc aacacggcct ccctgaccgt ctctggcctc | 240 |
| cagcctgagg atgaggctga ctattattgc gcctcttatg gaggcaggaa caatttgctt | 300 |
| tttggcggag ggactcaact gaccgtctta | 330 |

<210> SEQ ID NO 32
<211> LENGTH: 110
<212> TYPE: PRT
<213> ORGANISM: Artificial Sequence
<220> FEATURE:
<223> OTHER INFORMATION: 3-1H2 VL

<400> SEQUENCE: 32

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Pro Glu Asp Glu Ala Asp Tyr Tyr Cys Ala Ser Tyr Gly Gly Arg
                85                  90                  95

Asn Asn Leu Leu Phe Gly Gly Gly Thr Gln Leu Thr Val Leu
            100                 105                 110

<210> SEQ ID NO 33
<211> LENGTH: 354
<212> TYPE: DNA
<213> ORGANISM: Artificial Sequence
<220> FEATURE:
<223> OTHER INFORMATION: 3-1E4 VH

<400> SEQUENCE: 33

| | |
|---|---|
| caaatccagc tggtacaatc tggggctgag gtgaagaagc ctgggtcctc ggtgaaggtc | 60 |
| tcctgcaagg cttctggagg cacctttcagc agctatgcta tcagctgggt gcgacaggcc | 120 |
| cctggacaag gcttgagtg gatgggaggg atcatcccta tctttggtac agcaaactac | 180 |
| gcacagaagt tccagggcag agtcacgatt accgcggaca atccacgag cacagcctac | 240 |
| atggagctga gcagcctgag atctgaggac acggccgtgt attactgtgc cggagggga | 300 |
| gcagtggcgg acaatagtta ctggggccag ggaaccctgg tcaccgtctc ctca | 354 |

```
<210> SEQ ID NO 34
<211> LENGTH: 118
<212> TYPE: PRT
<213> ORGANISM: Artificial Sequence
<220> FEATURE:
<223> OTHER INFORMATION: 3-1E4 VH

<400> SEQUENCE: 34

Gln Ile Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Ala Val Ala Asp Asn Ser Tyr Trp Gly Gln Gly Thr
            100                 105                 110

Leu Val Thr Val Ser Ser
        115

<210> SEQ ID NO 35
<211> LENGTH: 321
<212> TYPE: DNA
<213> ORGANISM: Artificial Sequence
<220> FEATURE:
<223> OTHER INFORMATION: 3-1E4 VL

<400> SEQUENCE: 35
gacatccgga tgacccagtc tccatcctcc ctgtctgcat ctgtaggaga cagagtcacc      60
atcacttgcc gggcaagtca gggcattaga aatgatttag gctggtatca gcagaaacca    120
gggaaagccc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt accctcgaac gttcggccaa    300
gggaccaagg tggaaatcaa a                                              321

<210> SEQ ID NO 36
<211> LENGTH: 107
<212> TYPE: PRT
<213> ORGANISM: Artificial Sequence
<220> FEATURE:
<223> OTHER INFORMATION: 3-1E4 VL

<400> SEQUENCE: 36

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Asp Tyr Asn Tyr Pro Arg
            85                  90                  95

Thr Phe Gly Gln Gly Thr Lys Val Glu Ile Lys
            100                 105

<210> SEQ ID NO 37
<211> LENGTH: 366
<212> TYPE: DNA
<213> ORGANISM: Artificial Sequence
<220> FEATURE:
<223> OTHER INFORMATION: 3-1A8 VH

<400> SEQUENCE: 37
caaatccagc tggtacaatc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg atgggaggg atcatcccta tctttggtac agcaaactac    180
gcacagaagt tccagggcag agtcacgatt accgcggacg aatccacgag cacggcctac   240
atggagctga gcagcctgag atctgaggac acggccgtgt attactgtgc gagagacggt   300
tcgtatagca gcagctggta ctcgtttgac tactggggcc agggaaccct ggtcaccgtc   360
tcctca                                                              366

<210> SEQ ID NO 38
<211> LENGTH: 122
<212> TYPE: PRT
<213> ORGANISM: Artificial Sequence
<220> FEATURE:
<223> OTHER INFORMATION: 3-1A8 VH

<400> SEQUENCE: 38

Gln Ile Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Gly Ser Tyr Ser Ser Ser Trp Tyr Ser Phe Asp Tyr Trp
            100                 105                 110

Gly Gln Gly Thr Leu Val Thr Val Ser Ser
        115                 120

<210> SEQ ID NO 39
<211> LENGTH: 333
<212> TYPE: DNA
<213> ORGANISM: Artificial Sequence
<220> FEATURE:
<223> OTHER INFORMATION: 3-1A8 VL

<400> SEQUENCE: 39
cagtctgccc tgactcagcc tgcctccgtg tctgggtctc ctggacagtc gatcaccatc    60
tcctgcactg gaaccagcag tgacgtcggt ggttataact atgtctcctg gtaccaacag   120
```

```
cacccaggca aagcccccaa actcatgatt tatgatgtca gtaatcggcc ctcaggggtt      180
tctaatcgct tctctggctc caagtctggc aacacggcct ccctgaccat ctctgggctc      240
caggctgagg acgaggctga ttattactgc tcctcatatg caggtgatat tagttatgta      300
ctgttcggcg gcgggaccaa gctgaccgtc cta                                   333
```

<210> SEQ ID NO 40
<211> LENGTH: 111
<212> TYPE: PRT
<213> ORGANISM: Artificial Sequence
<220> FEATURE:
<223> OTHER INFORMATION: 3-1A8 VL

<400> SEQUENCE: 40

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Asp
                85                  90                  95

Ile Ser Tyr Val Leu Phe Gly Gly Gly Thr Lys Leu Thr Val Leu
            100                 105                 110
```

<210> SEQ ID NO 41
<211> LENGTH: 351
<212> TYPE: DNA
<213> ORGANISM: Artificial Sequence
<220> FEATURE:
<223> OTHER INFORMATION: 3-1B11 VH

<400> SEQUENCE: 41

```
gaagtgcagc tggtggagtc tgggggaggc ttggtacagc ctggagggtc cctgagactc       60
tcctgtgcag cctctggatt cacttttagt gactatgaca tgatctgggt ccgccaggct      120
ccaggcaagg ggctggagtg ggtggcagtt atatcatatg atggaagtaa taatactat       180 gcagactccg tgaagggccg attcaccatc tccagagaca attccaagaa cacgctgtat      240
ctgcaaatga acagcctgag agctgaggac acggctgtgt attactgtgc gaaagagttc      300
tttggtgctt ttgatatctg gggccaaggg acaatggtca ccgtctcttc a               351
```

<210> SEQ ID NO 42
<211> LENGTH: 117
<212> TYPE: PRT
<213> ORGANISM: Artificial Sequence
<220> FEATURE:
<223> OTHER INFORMATION: 3-1B11 VH

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ile Trp Val Arg Gln Ala Pro Gly Lys Gly Leu Glu Trp Val
        35                  40                  45
```

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Phe Phe Gly Ala Phe Asp Ile Trp Gly Gln Gly Thr Met
            100                 105                 110

Val Thr Val Ser Ser
        115

<210> SEQ ID NO 43
<211> LENGTH: 324
<212> TYPE: DNA
<213> ORGANISM: Artificial Sequence
<220> FEATURE:
<223> OTHER INFORMATION: 3-1B11 VL

<400> SEQUENCE: 43
tcttctgagc tgactcagga ccctgctgtg tcggtggcct tgggacagac agtcacgatc     60
acatgccaag agacagcct caattactat tatgcaaact ggttccagct gaagccaggg    120
caggcccctg tacttgtcct ctttggtaaa aacaaccggc cctcaggat cccagaccga    180 ttctctggct cctactcggg aagcacagct tccttgacca tcactgggc tcaggcggaa    240 gatgacgctg actattactg taattcgcgg gacagcggtg gtaatccttg ggtgttcggc    300
ggagggacca agctgaccgt ccta                                          324

<210> SEQ ID NO 44
<211> LENGTH: 108
<212> TYPE: PRT
<213> ORGANISM: Artificial Sequence
<220> FEATURE:
<223> OTHER INFORMATION: 3-1B11 VL

<400> SEQUENCE: 44

Ser Ser Glu Leu Thr Gln Asp Pro Ala Val Ser Val Ala Leu Gly Gln
 1               5                  10                  15

Thr Val Thr Ile Thr Cys Gln Gly Asp Ser Leu Asn Tyr Tyr Tyr Ala
             20                  25                  30

Asn Trp Phe Gln Leu Lys Pro Gly Gln Ala Pro Val Leu Val Leu Phe
             35                  40                  45

Gly Lys Asn Asn Arg Pro Ser Gly Ile Pro Asp Arg Phe Ser Gly Ser
 50                  55                  60

Tyr Ser Gly Ser Thr Ala Ser Leu Thr Ile Thr Gly Ala Gln Ala Glu
 65                  70                  75                  80

Asp Asp Ala Asp Tyr Tyr Cys Asn Ser Arg Asp Ser Gly Gly Asn Pro
                 85                  90                  95

Trp Val Phe Gly Gly Gly Thr Lys Leu Thr Val Leu
             100                 105

<210> SEQ ID NO 45
<211> LENGTH: 357
<212> TYPE: DNA
<213> ORGANISM: Artificial Sequence
<220> FEATURE:
<223> OTHER INFORMATION: 4-1F3 VH

<400> SEQUENCE: 45

```
caaatccagc tggtacaatc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaagg atcatcccta tccttggtat agcagactac     180
gcacagaagt tccagggcag agtcacgatt accgcggaca atccacgag cacagcctac      240 atggaactga gtagcctggg atctgaggac acggccgtgt attttgtgc gagagagggg      300 ggatccttta ggcactttga cttctggggc cagggaaccc tggtcaccgt ctcctca        357
```

<210> SEQ ID NO 46
<211> LENGTH: 119
<212> TYPE: PRT
<213> ORGANISM: Artificial Sequence
<220> FEATURE:
<223> OTHER INFORMATION: 4-1F3 VH

<400> SEQUENCE: 46

```
Gln Ile Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asp Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Gly Ser Glu Asp Thr Ala Val Tyr Phe Cys
                85                  90                  95

Ala Arg Glu Gly Gly Ser Phe Arg His Phe Asp Phe Trp Gly Gln Gly
            100                 105                 110

Thr Leu Val Thr Val Ser Ser
        115
```

<210> SEQ ID NO 47
<211> LENGTH: 333
<212> TYPE: DNA
<213> ORGANISM: Artificial Sequence
<220> FEATURE:
<223> OTHER INFORMATION: 4-1F3 VL

<400> SEQUENCE: 47

```
cagcctgtgc tgactcagcc accctcagtc tctggggccc cagggcagag ggtcaccatc      60
tcctgcgctg ggagcgaccc caacatcggg acaggtcatg atgtgcactg gtaccagcaa     120
cttccaggaa cagcccccaa actcgtcatc tatggtaaca ccaatcggcc ctcagggggtc    180 cctgagcgat tcactgcctc caagtctggc acctcagcct ccctggccat cactgggctc     240
caggctgagg atgaggctga ttattactgc caggcctacg acaggagcct gcgtggttat     300
gtcttcggga ctgggaccaa ggtcaccgtc ctg                                  333
```

<210> SEQ ID NO 48
<211> LENGTH: 111
<212> TYPE: PRT
<213> ORGANISM: Artificial Sequence
<220> FEATURE:
<223> OTHER INFORMATION: 4-1F3 VL

<400> SEQUENCE: 48

```
Gln Pro Val Leu Thr Gln Pro Pro Ser Val Ser Gly Ala Pro Gly Gln
```

```
            1               5                  10                 15
Arg Val Thr Ile Ser Cys Ala Gly Ser Asp Pro Asn Ile Gly Thr Gly
                    20                 25                 30

His Asp Val His Trp Tyr Gln Gln Leu Pro Gly Thr Ala Pro Lys Leu
            35                 40                 45

Val Ile Tyr Gly Asn Thr Asn Arg Pro Ser Gly Val Pro Glu Arg Phe
    50                 55                 60

Thr Ala Ser Lys Ser Gly Thr Ser Ala Ser Leu Ala Ile Thr Gly Leu
65                 70                 75                 80

Gln Ala Glu Asp Glu Ala Asp Tyr Tyr Cys Gln Ala Tyr Asp Arg Ser
                85                 90                 95

Leu Arg Gly Tyr Val Phe Gly Thr Gly Thr Lys Val Thr Val Leu
            100                105                110

<210> SEQ ID NO 49
<211> LENGTH: 369
<212> TYPE: DNA
<213> ORGANISM: Artificial Sequence
<220> FEATURE:
<223> OTHER INFORMATION: 4-1G5 VH

<400> SEQUENCE: 49
caaatccagc tggtacagtc tggtgctgaa gtgaagaagc ctggggcctc agtgaaggtc    60
tcctgcaaga cttctggtta cacctttacc agctatggta tcagctgggt gcgacaggcc   120
cctggacaag gcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagaactaca   300
ggtgacgagt ggctacgatt ggctataaat gactactggg gccagggaac cctggtcacc   360
gtctcctca                                                          369

<210> SEQ ID NO 50
<211> LENGTH: 123
<212> TYPE: PRT
<213> ORGANISM: Artificial Sequence
<220> FEATURE:
<223> OTHER INFORMATION: 4-1G5 VH

<400> SEQUENCE: 50

Gln Ile Gln Leu Val Gln Ser Gly Ala Glu Val Lys Lys Pro Gly Ala
1               5                  10                 15

Ser Val Lys Val Ser Cys Lys Thr Ser Gly Tyr Thr Phe Thr Ser Tyr
                20                 25                 30

Gly Ile Ser Trp Val Arg Gln Ala Pro Gly Gln Gly Leu Glu Trp Met
            35                 40                 45

Gly Trp Ile Ser Ala Tyr Asn Gly Asn Thr Asn Tyr Ala Gln Lys Leu
    50                 55                 60

Gln Gly Arg Val Thr Met Thr Thr Asp Thr Ser Thr Ser Thr Ala Tyr
65                 70                 75                 80

Met Glu Leu Arg Ser Leu Arg Ser Asp Asp Thr Ala Val Tyr Tyr Cys
                85                 90                 95

Ala Arg Thr Thr Gly Asp Glu Trp Leu Arg Leu Ala Ile Asn Asp Tyr
            100                105                110

Trp Gly Gln Gly Thr Leu Val Thr Val Ser Ser
    115                120
```

<210> SEQ ID NO 51
<211> LENGTH: 336
<212> TYPE: DNA
<213> ORGANISM: Artificial Sequence
<220> FEATURE:
<223> OTHER INFORMATION: 4-1G5 VL

<400> SEQUENCE: 51

```
gatattgtga tgacacagtc tcccctctcc ctgcccgtca cccctggaga gccggcctcc    60
atctcctgca ggtctagtct gcgcctcatg catcctaatg gactcaacta tttggattgg   120
tacctgcaga agccagggca gtctccacag ctcctaatct ttttgggttc tcagcgggcc   180
tccggggtcc ctgacaggtt cagtggcagt ggatcaggca cagattttac actgaaaatc   240
agcagagtgg aggctgagga tgttggcatt tattactgca tgcaagctct agaacctccg   300
tacacttttg gccaggggac caagctggag atcaaa                             336
```

<210> SEQ ID NO 52
<211> LENGTH: 112
<212> TYPE: PRT
<213> ORGANISM: Artificial Sequence
<220> FEATURE:
<223> OTHER INFORMATION: 4-1G5 VL

<400> SEQUENCE: 52

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Leu Arg Leu Met His Pro
            20                  25                  30

Asn Gly Leu Asn Tyr Leu Asp Trp Tyr Leu Gln Lys Pro Gly Gln Ser
        35                  40                  45

Pro Gln Leu Leu Ile Phe Leu Gly Ser Gln Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Glu Pro Pro Tyr Thr Phe Gly Gln Gly Thr Lys Leu Glu Ile Lys
            100                 105                 110
```

<210> SEQ ID NO 53
<211> LENGTH: 372
<212> TYPE: DNA
<213> ORGANISM: Artificial Sequence
<220> FEATURE:
<223> OTHER INFORMATION: 4-1C9 VH

<400> SEQUENCE: 53

```
caggtccagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagagatccc   300
gggtatagca gtggctggaa agatgatgct tttgatatct ggggccaagg gacaatggtc   360
accgtctctt ca                                                       372
```

<210> SEQ ID NO 54
<211> LENGTH: 124

<212> TYPE: PRT
<213> ORGANISM: Artificial Sequence
<220> FEATURE:
<223> OTHER INFORMATION: 4-1C9 VH

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Tyr Ser Ser Gly Trp Lys Asp Asp Ala Phe Asp
            100                 105                 110

Ile Trp Gly Gln Gly Thr Met Val Thr Val Ser Ser
        115                 120

<210> SEQ ID NO 55
<211> LENGTH: 324
<212> TYPE: DNA
<213> ORGANISM: Artificial Sequence
<220> FEATURE:
<223> OTHER INFORMATION: 4-1C9 VL

<400> SEQUENCE: 55
gaaattgtga tgacacagtc tccaggcacc ctgtctttgt ctccagggga tacagcctcc      60
ctctcctgca gggccagtca gactgttagc agcaactact tagcctggta ccaacagaaa     120
cctggccagg ctcccaggct cctcatctat gatacatcca acagggccgc tggcatcccg     180
gccaggttca gtggcagtgg gtctgggaca gacttcactc tcaccatcag tagcctagag     240
cctgaagatt ttgcagtgta ttactgtcag cagtacggta gctcactctg gacgttcggc     300
caagggacca aggtggaaat caaa                                              324

<210> SEQ ID NO 56
<211> LENGTH: 108
<212> TYPE: PRT
<213> ORGANISM: Artificial Sequence
<220> FEATURE:
<223> OTHER INFORMATION: 4-1C9 VL

<400> SEQUENCE: 56

Glu Ile Val Met Thr Gln Ser Pro Gly Thr Leu Ser Leu Ser Pro Gly
1               5                   10                  15

Asp Thr Ala Ser Leu Ser Cys Arg Ala Ser Gln Thr Val Ser Ser Asn
            20                  25                  30

Tyr Leu Ala Trp Tyr Gln Gln Lys Pro Gly Gln Ala Pro Arg Leu Leu
        35                  40                  45

Ile Tyr Asp Thr Ser Asn Arg Ala Ala Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Leu

```
              85                  90                  95
Trp Thr Phe Gly Gln Gly Thr Lys Val Glu Ile Lys
        100                 105

<210> SEQ ID NO 57
<211> LENGTH: 360
<212> TYPE: DNA
<213> ORGANISM: Artificial Sequence
<220> FEATURE:
<223> OTHER INFORMATION: 11-A4 VH

<400> SEQUENCE: 57
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac      180
gcacagaagt tccagggcag agtcacgatt accgcggacg aatccacgag cacagcctac     240
atggagctga gcagcctgag atctgaggac acggccgtgt attactgtgc gagagcgggg     300
cagcagctgg tagcccttg gtactactgg ggccaggaa ccctggtcac cgtctcctca      360

<210> SEQ ID NO 58
<211> LENGTH: 120
<212> TYPE: PRT
<213> ORGANISM: Artificial Sequence
<220> FEATURE:
<223> OTHER INFORMATION: 11-A4 VH

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Gln Gln Leu Val Ala Leu Trp Tyr Tyr Trp Gly Gln
            100                 105                 110

Gly Thr Leu Val Thr Val Ser Ser
        115                 120

<210> SEQ ID NO 59
<211> LENGTH: 330
<212> TYPE: DNA
<213> ORGANISM: Artificial Sequence
<220> FEATURE:
<223> OTHER INFORMATION: 11-A4 VL

<400> SEQUENCE: 59
cagtctgccc tgactcagcc tccctccgcg tccgggtctc gtggacagtc agtctccatc      60
tcctgcagtg gaagtcgcag tgacattgga tattataact atgtctcctg gtatcaacaa     120
cacccaggca agcccccaa actcatcatt tttgacgtca ataagcggcc ctcagggtc      180 cctgatcgct tctctggctc caagtctggc aacacggcct ccctgaccgt ctctggcctc     240
```
cagcctgagg atgaggctga ctattattgc gcctcttatg gaggcaggaa caatttgctt    300
tttggcggag ggactcaact gaccgtctta                                     330

<210> SEQ ID NO 60
<211> LENGTH: 110
<212> TYPE: PRT
<213> ORGANISM: Artificial Sequence
<220> FEATURE:
<223> OTHER INFORMATION: 11-A4 VL

<400> SEQUENCE: 60

Gln Ser Ala Leu Thr Gln Pro Pro Ser Ala Ser Gly Ser Arg Gly Gln
1               5                   10                  15

Ser Val Ser Ile Ser Cys Ser Gly Ser Arg Ser Asp Ile Gly Tyr Tyr
            20                  25                  30

Asn Tyr Val Ser Trp Tyr Gln Gln His Pro Gly Lys Ala Pro Lys Leu
        35                  40                  45

Ile Ile Phe Asp Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Pro Glu Asp Glu Ala Asp Tyr Tyr Cys Ala Ser Tyr Gly Gly Arg
                85                  90                  95

Asn Asn Leu Leu Phe Gly Gly Gly Thr Gln Leu Thr Val Leu
            100                 105                 110

<210> SEQ ID NO 61
<211> LENGTH: 363
<212> TYPE: DNA
<213> ORGANISM: Artificial Sequence
<220> FEATURE:
<223> OTHER INFORMATION: 21-A1 VH

<400> SEQUENCE: 61
caggtgcaac tgcaggagtc gggcccagga ctggtggagc cttcggagac cctgtccctc     60
acctgcactg tctctggtgg ctccatcagt agtttctact ggagctggat ccggcagccc    120
ccagggaagg gactggagtg gattggctat atcaattaca gtgggagcac caactacaac    180
ccctccctca gagtcgagt caccatatca gtagacacgt ccaagaacca gttctccctg    240
aagctgagct ctgtgaccgc cgcagacacg gctgtgtatt actgtgcgag acagatatta    300
tggttcgggg agttaaggtg gttcgacccc tggggccagg gaaccctggt caccgtctcc    360
tca                                                                  363

<210> SEQ ID NO 62
<211> LENGTH: 121
<212> TYPE: PRT
<213> ORGANISM: Artificial Sequence
<220> FEATURE:
<223> OTHER INFORMATION: 21-A1 VH

<400> SEQUENCE: 62

Gln Val Gln Leu Gln Glu Ser Gly Pro Gly Leu Val Glu Pro Ser Glu
1               5                   10                  15

Thr Leu Ser Leu Thr Cys Thr Val Ser Gly Gly Ser Ile Ser Ser Phe
            20                  25                  30

Tyr Trp Ser Trp Ile Arg Gln Pro Pro Gly Lys Gly Leu Glu Trp Ile
        35                  40                  45

Gly Tyr Ile Asn Tyr Ser Gly Ser Thr Asn Tyr Asn Pro Ser Leu Lys

```
                       50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gln Ile Leu Trp Phe Gly Glu Leu Arg Trp Phe Asp Pro Trp Gly
            100                 105                 110

Gln Gly Thr Leu Val Thr Val Ser Ser
        115                 120
```

<210> SEQ ID NO 63
<211> LENGTH: 330
<212> TYPE: DNA
<213> ORGANISM: Artificial Sequence
<220> FEATURE:
<223> OTHER INFORMATION: 21-A1 VL

<400> SEQUENCE: 63

```
cagtctgccc tgactcagcc tccctccgcg tccgggtctc ctggacagtc agtcaccatc    60
tcctgcactg gaaccagcag tgacattggt ggttataact atgtctcctg gtaccaactg   120
cgcccaggca aagcccccaa actcatgatt tatgacgtca ccaagcggcc ctcaggggtc   180
cctgatcgct tctctggctc caagtctggc aacacggcct ccctgaccgt ctctgggctc   240
caggctgagg atgaggctga ttattactgc agctcatatg caggcagcaa caatgtggta   300
ttcggcggag ggaccaagct gaccgtccta                                     330
```

<210> SEQ ID NO 64
<211> LENGTH: 110
<212> TYPE: PRT
<213> ORGANISM: Artificial Sequence
<220> FEATURE:
<223> OTHER INFORMATION: 21-A1 VL

<400> SEQUENCE: 64

```
Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Ile Gly Gly Tyr
                20                  25                  30

Asn Tyr Val Ser Trp Tyr Gln Leu Arg Pro Gly Lys Ala Pro Lys Leu
            35                  40                  45

Met Ile Tyr Asp Val Thr Lys Arg Pro Ser Gly Val Pro Asp Arg Phe
        50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Val Val Phe Gly Gly Gly Thr Lys Leu Thr Val Leu
            100                 105                 110
```

<210> SEQ ID NO 65
<211> LENGTH: 357
<212> TYPE: DNA
<213> ORGANISM: Artificial Sequence
<220> FEATURE:
<223> OTHER INFORMATION: 21-H12 VH

<400> SEQUENCE: 65

```
caagtccagc tggtacagtc tggggctgag gtgaagaagc ctggggcctc ggtgaaggtc    60
```

```
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaaatccc    300
tacggtttca actggttcga ccctggggc cagggaaccc tggtcaccgt ctcctca       357
```

<210> SEQ ID NO 66
<211> LENGTH: 119
<212> TYPE: PRT
<213> ORGANISM: Artificial Sequence
<220> FEATURE:
<223> OTHER INFORMATION: 21-H12 VH

<400> SEQUENCE: 66

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Pro Tyr Gly Phe Asn Trp Phe Asp Pro Trp Gly Gln Gly
            100                 105                 110

Thr Leu Val Thr Val Ser Ser
        115
```

<210> SEQ ID NO 67
<211> LENGTH: 330
<212> TYPE: DNA
<213> ORGANISM: Artificial Sequence
<220> FEATURE:
<223> OTHER INFORMATION: 21-H12 VL

<400> SEQUENCE: 67

```
aattttatgc tgactcagcc ccactctgtg tcggagtctc cggggaagac ggtaaccatc    60
tcctgcaccc gcagcagtgg cagcattgcc agcaactatg tgcagtggta ccagcagcgc    120
ccgggcagtg cccccaccac tgtgatctat gaggataacc aaagaccctc tggggtccct    180
gatcggttct ctggctccat cgacagctcc tccaactctg cctccctcac catctccgga    240
ctgaagactg aggacgaggc tgactactac tgtcagtctt atgatggctt caatcaggtg    300
ttcggcggag ggaccaagct gaccgtccta                                     330
```

<210> SEQ ID NO 68
<211> LENGTH: 110
<212> TYPE: PRT
<213> ORGANISM: Artificial Sequence
<220> FEATURE:
<223> OTHER INFORMATION: 21-H12 VL

<400> SEQUENCE: 68

```
Asn Phe Met Leu Thr Gln Pro His Ser Val Ser Glu Ser Pro Gly Lys
1               5                   10                  15
```

```
Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Gly
                85                  90                  95

Phe Asn Gln Val Phe Gly Gly Gly Thr Lys Leu Thr Val Leu
            100                 105                 110

<210> SEQ ID NO 69
<211> LENGTH: 372
<212> TYPE: DNA
<213> ORGANISM: Artificial Sequence
<220> FEATURE:
<223> OTHER INFORMATION: 7-D12 VH

<400> SEQUENCE: 69
caaatgcagc tggtacagtc tggggctgag gtgaagaagc ctgggtcctc ggtgaaggtc      60
tcctgcaagg cttctggagg caccttcagc agctatgcta tcagctgggt gcgacaggcc    120
cctggacaag gcttgagtg gatgggaggg atcatcccta tctttggtac agcaaactac     180
gcacagaagt tccagggcag agtcacgatt accgcggaca aatccacgag cacagcctac    240
atggagctga gcagcctgag atctgaggac acggccgtgt attactgtgc gagaaccggt    300
agtagtggtt atgtacgttg gagcaactgg ttcgacccct ggggccaggg aaccctggtc    360
accgtctcct ca                                                         372

<210> SEQ ID NO 70
<211> LENGTH: 124
<212> TYPE: PRT
<213> ORGANISM: Artificial Sequence
<220> FEATURE:
<223> OTHER INFORMATION: 7-D12 VH

<400> SEQUENCE: 70

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Ser Ser Gly Tyr Val Arg Trp Ser Asn Trp Phe Asp
            100                 105                 110

Pro Trp Gly Gln Gly Thr Leu Val Thr Val Ser Ser
        115                 120

<210> SEQ ID NO 71
<211> LENGTH: 321
```

-continued

```
<212> TYPE: DNA
<213> ORGANISM: Artificial Sequence
<220> FEATURE:
<223> OTHER INFORMATION: 7-D12 VL

<400> SEQUENCE: 71
gacatccaga tgacccagtc tccctccacc ctgtctgcat tgtaggaga cagagtcacc    60 atcacttgcc gggccagtga gagtattagt aggtggttgg cctggtatca gcagaaacca   120
gggaaagccc ctaaactcct aatctctaag acgtctaatt tagaaagcgg ggtcccgtca   180
aggttcagtg gcgctggatc tgggacagat ttcactctca ccattagcag tctgcaacct   240
gaggattttg caacttactt ctgtcaacag ggttccaaaa tgcctccgac tttcggcgga   300
gggaccaagg tggagatcaa g                                              321

<210> SEQ ID NO 72
<211> LENGTH: 107
<212> TYPE: PRT
<213> ORGANISM: Artificial Sequence
<220> FEATURE:
<223> OTHER INFORMATION: 7-D12 VL

<400> SEQUENCE: 72

Asp Ile Gln Met Thr Gln Ser Pro Ser Thr Leu Ser Ala Phe Val Gly
1               5                   10                  15

Asp Arg Val Thr Ile Thr Cys Arg Ala Ser Glu Ser Ile Ser Arg Trp
            20                  25                  30

Leu Ala Trp Tyr Gln Gln Lys Pro Gly Lys Ala Pro Lys Leu Leu Ile
        35                  40                  45

Ser Lys Thr Ser Asn Leu Glu Ser Gly Val Pro Ser Arg Phe Ser Gly
    50                  55                  60

Ala Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ser Lys Met Pro Pro
                85                  90                  95

Thr Phe Gly Gly Gly Thr Lys Val Glu Ile Lys
            100                 105

<210> SEQ ID NO 73
<211> LENGTH: 360
<212> TYPE: DNA
<213> ORGANISM: Artificial Sequence
<220> FEATURE:
<223> OTHER INFORMATION: 9-E3 VH

<400> SEQUENCE: 73
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcacgatt accgcgacg aatccacgag cacagcctac   240
atggagctga gcagcctgag atctgaggac acggccgtgt attactgtgc gagggggcc   300 tacggtggta actccgcttt tgactactgg ggccaggaa ccctggtcac cgtctcctca   360

<210> SEQ ID NO 74
<211> LENGTH: 120
<212> TYPE: PRT
<213> ORGANISM: Artificial Sequence
<220> FEATURE:
<223> OTHER INFORMATION: 9-E3 VH
```

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Gly Gly Asn Ser Ala Phe Asp Tyr Trp Gly Gln
            100                 105                 110

Gly Thr Leu Val Thr Val Ser Ser
        115                 120

<210> SEQ ID NO 75
<211> LENGTH: 333
<212> TYPE: DNA
<213> ORGANISM: Artificial Sequence
<220> FEATURE:
<223> OTHER INFORMATION: 9-E3 VL

<400> SEQUENCE: 75
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatg tacagtaatg atcagcggcc ctcagggatc     180
actgagcgat tctctggctc caagtctggc acctcagcct ccctggccat cagtgggctc     240
cagtctgaag atgagggtga ttactactgc cagtcctatg acagaagcct gagaggttcg     300
gtcttcggcg gagggaccaa gctgaccgtc ctc                                  333

<210> SEQ ID NO 76
<211> LENGTH: 111
<212> TYPE: PRT
<213> ORGANISM: Artificial Sequence
<220> FEATURE:
<223> OTHER INFORMATION: 9-E3 VL

<400> SEQUENCE: 76

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Met Tyr Ser Asn Asp Gln Arg Pro Ser Gly Val Thr Glu Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Gly Asp Tyr Tyr Cys Gln Ser Tyr Asp Arg Ser
                85                  90                  95

Leu Arg Gly Ser Val Phe Gly Gly Gly Thr Lys Leu Thr Val Leu
            100                 105                 110

<210> SEQ ID NO 77
<211> LENGTH: 363
<212> TYPE: DNA
<213> ORGANISM: Artificial Sequence
<220> FEATURE:
<223> OTHER INFORMATION: 10-A6 VH

<400> SEQUENCE: 77

```
gaggtgcagc tggtgcagtc tggggctgag gtgaagaagc ctggggcctc agtgaaggtt      60
tcctgcaagg cttctggtta cacctttacc agctatggta tcagctgggt gcgacaggcc     120
cctggacaag gcttgagtg gatgggatgg atcagcgctt acaatggtaa cacaaactat      180
gcacagaagc tccagggcag agtcaccatg accacagaca catccacgag cacagcctac     240
atggagctga ggagcctgag atctgacgac acggccgtgt attactgtgc gagagattcc     300
atagcagcag ctggtactcc gttcgactac tggggccagg gaaccctggt caccgtctcc     360
tca                                                                   363
```

<210> SEQ ID NO 78
<211> LENGTH: 121
<212> TYPE: PRT
<213> ORGANISM: Artificial Sequence
<220> FEATURE:
<223> OTHER INFORMATION: 10-A6 VH

<400> SEQUENCE: 78

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ile Ala Ala Ala Gly Thr Pro Phe Asp Tyr Trp Gly
            100                 105                 110

Gln Gly Thr Leu Val Thr Val Ser Ser
        115                 120
```

<210> SEQ ID NO 79
<211> LENGTH: 330
<212> TYPE: DNA
<213> ORGANISM: Artificial Sequence
<220> FEATURE:
<223> OTHER INFORMATION: 10-A6 VL

<400> SEQUENCE: 79

```
aattttatgc tgactcagcc ccactctgtg tcggagtctc cggggaagac ggtcaccatc      60
tcctgcaccc gcagcagtgg catcattgcc agcaaatatg tgcactggta ccagcagcgc     120
ccgggcagtg cccccaccac tgtgatctat gaggataacc aaagaccgtc tggggtccct     180
gatcgattct ctgcctccat cgacaactcc tccaactctg cctccctcac catctctgga     240
ctgcagactg aggacgaggc tgactactac tgtcagtctc atgacggcat caatcaggtt     300
```
ttcggcggag ggaccaaggt caccgtccta      330

<210> SEQ ID NO 80
<211> LENGTH: 110
<212> TYPE: PRT
<213> ORGANISM: Artificial Sequence
<220> FEATURE:
<223> OTHER INFORMATION: 10-A6 VL

<400> SEQUENCE: 80

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ile Ile Ala Ser Lys
            20                  25                  30

Tyr Val His Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Asn Ser Ser Asn Ser Ala Ser Leu Thr Ile Ser Gly
65                  70                  75                  80

Leu Gln Thr Glu Asp Glu Ala Asp Tyr Tyr Cys Gln Ser His Asp Gly
                85                  90                  95

Ile Asn Gln Val Phe Gly Gly Gly Thr Lys Val Thr Val Leu
            100                 105                 110

<210> SEQ ID NO 81
<211> LENGTH: 372
<212> TYPE: DNA
<213> ORGANISM: Artificial Sequence
<220> FEATURE:
<223> OTHER INFORMATION: 12-A4 VH

<400> SEQUENCE: 81
gaggtgcagc tggtggagtc ccggggaggc ttggtacagc cggggggtc cctgagactc      60 tcctgtgtaa cttctggatt cagctttaac aactatgcca tgaactgggt ccgccaggct     120
ccggggaagg ggctggagtg ggtctcagct gttagtggta gtggtggtac cacatactac     180
gcagactccg tgaagggccg gttcaccatc tccagagaca attccaagaa cacgctgttt     240
gtgcagatgg acagcctgag agctgaggac acggctgtgt attactgtgc gaaaggactt     300
ttccctacga ttttggagt aggagcaatg tttgactact ggggccaggg aaccctggtc      360
accgtctcct ca                                                        372

<210> SEQ ID NO 82
<211> LENGTH: 124
<212> TYPE: PRT
<213> ORGANISM: Artificial Sequence
<220> FEATURE:
<223> OTHER INFORMATION: 12-A4 VH

<400> SEQUENCE: 82

Glu Val Gln Leu Val Glu Ser Arg Gly Gly Leu Val Gln Pro Gly Gly
1               5                   10                  15

Ser Leu Arg Leu Ser Cys Val Thr Ser Gly Phe Ser Phe Asn Asn Tyr
            20                  25                  30

Ala Met Asn Trp Val Arg Gln Ala Pro Gly Lys Gly Leu Glu Trp Val
        35                  40                  45

Ser Ala Val Ser Gly Ser Gly Gly Thr Thr Tyr Tyr Ala Asp Ser Val
    50                  55                  60

```
Lys Gly Arg Phe Thr Ile Ser Arg Asp Asn Ser Lys Asn Thr Leu Phe
 65                  70                  75                  80

Val Gln Met Asp Ser Leu Arg Ala Glu Asp Thr Ala Val Tyr Tyr Cys
                 85                  90                  95

Ala Lys Gly Leu Phe Pro Thr Ile Phe Gly Val Gly Ala Met Phe Asp
            100                 105                 110

Tyr Trp Gly Gln Gly Thr Leu Val Thr Val Ser Ser
            115                 120
```

<210> SEQ ID NO 83
<211> LENGTH: 330
<212> TYPE: DNA
<213> ORGANISM: Artificial Sequence
<220> FEATURE:
<223> OTHER INFORMATION: 12-A4 VL

<400> SEQUENCE: 83

```
tcttctgagc tgactcagcc accctcagcg tctgggaccc ccgggcagag ggtcaccatc      60
tcttgttctg gaagcagctc caacatcgga agtaatgctg ttaactggta tcagcagctc     120
ccaggaacgg cccccaaact cctcatctat gataataatc accggccctc agggstccct    180
gaccgattct ctggctccaa gtctggcacc tcagcctccc tggccatcag tgggctccag     240
tctgaggatg aggctgatta ttattgtgca gcatgggatg acaccattcc tggtgtgcta     300
ttcgccggag ggaccaagct gaccgtccta                                      330
```

<210> SEQ ID NO 84
<211> LENGTH: 110
<212> TYPE: PRT
<213> ORGANISM: Artificial Sequence
<220> FEATURE:
<223> OTHER INFORMATION: 12-A4 VL

<400> SEQUENCE: 84

```
Ser Ser Glu Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Ala Val Asn Trp Tyr Gln Gln Leu Pro Gly Thr Ala Pro Lys Leu Leu
             35                  40                  45

Ile Tyr Asp Asn Asn His Arg Pro Ser Gly Val Pro Asp Arg Phe Ser
         50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Thr Ile
                 85                  90                  95

Pro Gly Val Leu Phe Ala Gly Gly Thr Lys Leu Thr Val Leu
            100                 105                 110
```

<210> SEQ ID NO 85
<211> LENGTH: 357
<212> TYPE: DNA
<213> ORGANISM: Artificial Sequence
<220> FEATURE:
<223> OTHER INFORMATION: 14-G10 VH

<400> SEQUENCE: 85

```
gaagtgcagc tggtggagtc tggggctgag gtgaagaagc ctgggtcctc ggtgaaggtc      60
tcctgcaagg cttctggagg caccttcagc agctatgcta tcagctgggt gcgacaggcc     120
```

```
cctggacaag ggcttgagtg gatgggaggg atcatccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaggtgtt    300
tcttactact acggtatgga cgtctggggc caagggacca cggtcaccgt ctcctca       357
```

<210> SEQ ID NO 86
<211> LENGTH: 119
<212> TYPE: PRT
<213> ORGANISM: Artificial Sequence
<220> FEATURE:
<223> OTHER INFORMATION: 14-G10 VH

<400> SEQUENCE: 86

```
Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Ser Tyr Tyr Tyr Gly Met Asp Val Trp Gly Gln Gly
            100                 105                 110

Thr Thr Val Thr Val Ser Ser
        115
```

<210> SEQ ID NO 87
<211> LENGTH: 318
<212> TYPE: DNA
<213> ORGANISM: Artificial Sequence
<220> FEATURE:
<223> OTHER INFORMATION: 14-G10 VL

<400> SEQUENCE: 87

```
caggctgtgc tgactcagcc accctcggtg tccgtgtccc caggacagac agccatcatc    60
tcctgttctg gacataaatt gggtgataag tatgtttcct ggtatcaaca gcagccaggc   120
cagtcccctg tgctggtcct cttttcaggat accaagcggc cctcagggat ccctgagcga   180
ttctctggct ccaactctgg gaacacagcc actctgacca tcagcgcgac ccaggctgcg   240
gatgaggctg actattactg tcaggcgggg gacaccaagt ctgtgatctt cggcggcggg   300
accaagctga ccgtcccta                                                 318
```

<210> SEQ ID NO 88
<211> LENGTH: 106
<212> TYPE: PRT
<213> ORGANISM: Artificial Sequence
<220> FEATURE:
<223> OTHER INFORMATION: 14-G10 VL

<400> SEQUENCE: 88

```
Gln Ala Val Leu Thr Gln Pro Pro Ser Val Ser Val Ser Pro Gly Gln
1               5                   10                  15

Thr Ala Ile Ile Ser Cys Ser Gly His Lys Leu Gly Asp Lys Tyr Val
            20                  25                  30
```

```
Ser Trp Tyr Gln Gln Gln Pro Gly Gln Ser Pro Val Leu Val Leu Phe
        35                  40                  45

Gln Asp Thr Lys Arg Pro Ser Gly Ile Pro Glu Arg Phe Ser Gly Ser
 50                  55                  60

Asn Ser Gly Asn Thr Ala Thr Leu Thr Ile Ser Ala Thr Gln Ala Ala
 65                  70                  75                  80

Asp Glu Ala Asp Tyr Tyr Cys Gln Ala Gly Asp Thr Lys Ser Val Ile
                 85                  90                  95

Phe Gly Gly Gly Thr Lys Leu Thr Val Leu
            100                 105
```

<210> SEQ ID NO 89
<211> LENGTH: 360
<212> TYPE: DNA
<213> ORGANISM: Artificial Sequence
<220> FEATURE:
<223> OTHER INFORMATION: 22-A6 VH

<400> SEQUENCE: 89

```
caggttcagg tggtgcagtc tggggctgag gtgaagaagc ctgggtcctc ggtgaaggtc      60
tcctgcaagg cttctggagg caccttcagc agctatgcta tcagctgggt gcggcaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaggatac     300
agctatggtt caggacacct tgactactgg ggccagggaa ccctggtcac cgtctcctca     360
```

<210> SEQ ID NO 90
<211> LENGTH: 120
<212> TYPE: PRT
<213> ORGANISM: Artificial Sequence
<220> FEATURE:
<223> OTHER INFORMATION: 22-A6 VH

<400> SEQUENCE: 90

```
Gln Val Gln Val Val Gln Ser Gly Ala Glu Val Lys Lys Pro Gly Ser
 1               5                   10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Ser Tyr Gly Ser Gly His Leu Asp Tyr Trp Gly Gln
            100                 105                 110

Gly Thr Leu Val Thr Val Ser Ser
        115                 120
```

<210> SEQ ID NO 91
<211> LENGTH: 321
<212> TYPE: DNA
<213> ORGANISM: Artificial Sequence
<220> FEATURE:
<223> OTHER INFORMATION: 22-A6 VL

<400> SEQUENCE: 91

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg gtcccatca    180 aggttcagtg gcagtggatc tgggacagat ttcgctctca ccatcagcag tctccaacct   240
gaagattttg caacttatta ctgtctacag cataatagtt accctcggac ttttggccag   300
gggaccaagc tggagatcaa a                                             321
```

<210> SEQ ID NO 92
<211> LENGTH: 107
<212> TYPE: PRT
<213> ORGANISM: Artificial Sequence
<220> FEATURE:
<223> OTHER INFORMATION: 22-A6 VL

<400> SEQUENCE: 92

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Ala Leu Thr Ile Ser Ser Leu Gln Pro
 65                  70                  75                  80

Glu Asp Phe Ala Thr Tyr Tyr Cys Leu Gln His Asn Ser Tyr Pro Arg
                 85                  90                  95

Thr Phe Gly Gln Gly Thr Lys Leu Glu Ile Lys
            100                 105
```

<210> SEQ ID NO 93
<211> LENGTH: 360
<212> TYPE: DNA
<213> ORGANISM: Artificial Sequence
<220> FEATURE:
<223> OTHER INFORMATION: 35-B1 VH

<400> SEQUENCE: 93

```
gaggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atgaaccta acagtggtga cacagcctat    180
acacagaact tccagggcag agtcaccatg accaggaacc cctccataag cacagcctac   240
atggagctga gcaacctgag atctgaggac acggccgtgt attactgtgc gagaggccgg   300
gggttcgcgg agaagcccct tgggtactgg ggccagggaa ccctggtcac cgtctcctca   360
```

<210> SEQ ID NO 94
<211> LENGTH: 120
<212> TYPE: PRT
<213> ORGANISM: Artificial Sequence
<220> FEATURE:
<223> OTHER INFORMATION: 35-B1 VH

<400> SEQUENCE: 94

Glu Val Gln Leu Val Gln Ser Gly Ala Glu Val Lys Lys Pro Gly Ala

```
1               5                   10                  15
Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Met Asn Pro Asn Ser Gly Asp Thr Ala Tyr Thr Gln Asn Phe
        50                  55                  60

Gln Gly Arg Val Thr Met Thr Arg Asn Pro Ser Ile Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Gly Arg Gly Phe Ala Glu Lys Pro Leu Gly Tyr Trp Gly Gln
                100                 105                 110

Gly Thr Leu Val Thr Val Ser Ser
            115                 120
```

<210> SEQ ID NO 95
<211> LENGTH: 339
<212> TYPE: DNA
<213> ORGANISM: Artificial Sequence
<220> FEATURE:
<223> OTHER INFORMATION: 35-B1 VL

<400> SEQUENCE: 95

```
gatattgtga tgactcagtc tccagactcc ctggctgtgt ctctgggcgg agggccacc    60 atcaactgca gtccagcca gagtatttta tccagctcca ataataagaa ctatttagct   120
tggtaccagc agaaaccagg tcagcctcct aagctgctca tttactgggc atctacccgg   180
gaatccgggg tccctgaccg gttcagcggc agcgggtctg ggacagattt cactctcacc   240
atcagcagcc tgcaggctga gatgtggca gtttattact gtcagcaata ttatagtact   300
cctccgacat tcggccaagg gaccaaggtg gaaatcaaa                          339
```

<210> SEQ ID NO 96
<211> LENGTH: 113
<212> TYPE: PRT
<213> ORGANISM: Artificial Sequence
<220> FEATURE:
<223> OTHER INFORMATION: 35-B1 VL

<400> SEQUENCE: 96

```
Asp Ile Val Met Thr Gln Ser Pro Asp Ser Leu Ala Val Ser Leu Gly
1               5                   10                  15

Gly Arg Ala Thr Ile Asn Cys Lys Ser Ser Gln Ser Ile Leu Ser Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
                100                 105                 110

Lys
```

```
<210> SEQ ID NO 97
<211> LENGTH: 366
<212> TYPE: DNA
<213> ORGANISM: Artificial Sequence
<220> FEATURE:
<223> OTHER INFORMATION: 3-1F4 VH

<400> SEQUENCE: 97
gaggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagggcccct     300
cgagggcagt ggctggttca ctactttgac tactggggcc agggaaccct ggtcaccgtc     360
tcctca                                                                366

<210> SEQ ID NO 98
<211> LENGTH: 122
<212> TYPE: PRT
<213> ORGANISM: Artificial Sequence
<220> FEATURE:
<223> OTHER INFORMATION: 3-1F4 VH

<400> SEQUENCE: 98

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Arg Gly Gln Trp Leu Val His Tyr Phe Asp Tyr Trp
            100                 105                 110

Gly Gln Gly Thr Leu Val Thr Val Ser Ser
        115                 120

<210> SEQ ID NO 99
<211> LENGTH: 321
<212> TYPE: DNA
<213> ORGANISM: Artificial Sequence
<220> FEATURE:
<223> OTHER INFORMATION: 3-1F4 VL

<400> SEQUENCE: 99
gaaattgtgt tgacgcagtc tccagccacc ctctctctgt ctccagggga aagagccacc      60
ctctcctgct gggccagtca ggatgttagc aactacttag cctggtacca acagaagcct     120
ggccaggctc ccaggctcct catctatgat gcatccaaca gggccactgg catcccagcc     180
aggttcagcg gcagtgggtc tgggacagac ttcactctca ccatcagcag cctagagcct     240
gaagattttg cagtgtatta ctgtcagcaa cgtagcaact ggcctctcac tttcggcggc     300
gggaccaagg tggagctcaa a                                               321
```

<210> SEQ ID NO 100
<211> LENGTH: 107
<212> TYPE: PRT
<213> ORGANISM: Artificial Sequence
<220> FEATURE:
<223> OTHER INFORMATION: 3-1F4 VL

<400> SEQUENCE: 100

```
Glu Ile Val Leu Thr Gln Ser Pro Ala Thr Leu Ser Leu Ser Pro Gly
1               5                   10                  15

Glu Arg Ala Thr Leu Ser Cys Trp Ala Ser Gln Asp Val Ser Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Leu Lys
            100                 105
```

<210> SEQ ID NO 101
<211> LENGTH: 357
<212> TYPE: DNA
<213> ORGANISM: Artificial Sequence
<220> FEATURE:
<223> OTHER INFORMATION: 4-1B3 VH

<400> SEQUENCE: 101

```
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagagtcc   300
tactcgtccg caggtattga ctactggggc cagggaaccc tggtcaccgt ctcctca      357
```

<210> SEQ ID NO 102
<211> LENGTH: 119
<212> TYPE: PRT
<213> ORGANISM: Artificial Sequence
<220> FEATURE:
<223> OTHER INFORMATION: 4-1B3 VH

<400> SEQUENCE: 102

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

85                  90                  95
Ala Arg Glu Ser Tyr Ser Ser Ala Gly Ile Asp Tyr Trp Gly Gln Gly
                100                 105                 110

Thr Leu Val Thr Val Ser Ser
        115

<210> SEQ ID NO 103
<211> LENGTH: 336
<212> TYPE: DNA
<213> ORGANISM: Artificial Sequence
<220> FEATURE:
<223> OTHER INFORMATION: 4-1B3 VL

<400> SEQUENCE: 103
gatattgtga tgactcagtc tccactctcc ctgcccgtca cccctggaga gccggcctcc      60
atctcctgca ggtctagtca gaccctcctg catagtaatg gattcaacta tttggattgg     120
tacctgcaga agccagggca gtctccacaa ctcctgatgt atttgggctc tagccgggcc     180
tccggggtcc ctgacaggtt cagtggcagt ggatcgggca cagatttcac actgaaaatc     240
agcagagtgg aggctgagga tgttggggtt tattactgca tgcaaactct acaaactcct     300
ccggctttcg gcggagggac caaggtggag atcaaa                               336

<210> SEQ ID NO 104
<211> LENGTH: 112
<212> TYPE: PRT
<213> ORGANISM: Artificial Sequence
<220> FEATURE:
<223> OTHER INFORMATION: 4-1B3 VL

<400> SEQUENCE: 104

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Leu His Ser
            20                  25                  30

Asn Gly Phe Asn Tyr Leu Asp Trp Tyr Leu Gln Lys Pro Gly Gln Ser
        35                  40                  45

Pro Gln Leu Leu Met Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Pro Ala Phe Gly Gly Gly Thr Lys Val Glu Ile Lys
            100                 105                 110

<210> SEQ ID NO 105
<211> LENGTH: 354
<212> TYPE: DNA
<213> ORGANISM: Artificial Sequence
<220> FEATURE:
<223> OTHER INFORMATION: 21-G1 VH

<400> SEQUENCE: 105
caggtccagc tggtgcagtc tggggctgag gtgaagaagc ctggggcctc agtgacgatt      60
tcctgcgagg cgtctggata caacttcatc agctactata cactgggt gcgacaggcc      120 cctggacaag gccttgagtg gatgggattc gtcgtcccta gtggtggtgc cgcaggctac     180
acacagaagt tccagggcag actcaccgtg accagggaca cgtccacgag cacagtctac     240

```
atggacctga  acagcctgac  atctgacgac  acggccgtgt  attactgtgt  gcgagaaatg      300
agtggtggct  ggtttgattt  ctggggccag  ggaaccctgg  tcaccgtctc  ctcg            354
```

<210> SEQ ID NO 106
<211> LENGTH: 118
<212> TYPE: PRT
<213> ORGANISM: Artificial Sequence
<220> FEATURE:
<223> OTHER INFORMATION: 21-G1 VH

<400> SEQUENCE: 106

Gln Val Gln Leu Val Gln Ser Gly Ala Glu Val Lys Lys Pro Gly Ala
1               5                   10                  15

Ser Val Thr Ile Ser Cys Glu Ala Ser Gly Tyr Asn Phe Ile Ser Tyr
            20                  25                  30

Tyr Ile His Trp Val Arg Gln Ala Pro Gly Gln Gly Leu Glu Trp Met
        35                  40                  45

Gly Phe Val Val Pro Ser Gly Gly Ala Ala Gly Tyr Thr Gln Lys Phe
    50                  55                  60

Gln Gly Arg Leu Thr Val Thr Arg Asp Thr Ser Thr Ser Thr Val Tyr
65                  70                  75                  80

Met Asp Leu Asn Ser Leu Thr Ser Asp Thr Ala Val Tyr Tyr Cys
                85                  90                  95

Val Arg Glu Met Ser Gly Gly Trp Phe Asp Phe Trp Gly Gln Gly Thr
            100                 105                 110

Leu Val Thr Val Ser Ser
        115

<210> SEQ ID NO 107
<211> LENGTH: 321
<212> TYPE: DNA
<213> ORGANISM: Artificial Sequence
<220> FEATURE:
<223> OTHER INFORMATION: 21-G1 VL

<400> SEQUENCE: 107

```
gacatccaga  tgacccagtc  tccatcctcc  ctgtctgcat  ctgtaggaga  cagagtcacc      60
atcacttgcc  gggcaagtca  gagcattagc  agctatttaa  attggtatca  gcagaaacca     120
gggaaagccc  ctaagctcct  gatctatgct  gcatccagtt  tgcaaagtgg  ggtcccatca     180
aggttcagtg  gcagtggatc  tgggacagat  ttcactctca  ccatcagcag  tctgcaacct     240
gaagattttg  caacttacta  ctgtcaacag  agttacagta  ccccgatcac  cttcggccaa     300
gggacacgac  tggagattaa  a                                                  321
```

<210> SEQ ID NO 108
<211> LENGTH: 107
<212> TYPE: PRT
<213> ORGANISM: Artificial Sequence
<220> FEATURE:
<223> OTHER INFORMATION: 21-G1 VL

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
                                                        -continued
Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Ile
                85              90              95

Thr Phe Gly Gln Gly Thr Arg Leu Glu Ile Lys
            100             105
```